United States Patent [19]
Sato et al.

[11] Patent Number: 5,079,357
[45] Date of Patent: Jan. 7, 1992

[54] DERIVATIVES OF PENEM

[75] Inventors: Makoto Sato; Makoto Takemura; Kunio Higashi; Tsunehiko Soga; Hiroo Matsumoto; Toshiyuki Nishi, all of Tokyo, Japan

[73] Assignee: Daiichi Pharmaceutical Co., Ltd., Tokyo, Japan

[21] Appl. No.: 449,391

[22] Filed: Dec. 7, 1989

Related U.S. Application Data

[63] Continuation of Ser. No. 38,640, Apr. 15, 1987, abandoned, which is a continuation-in-part of Ser. No. 875,228, Jun. 17, 1986, abandoned.

[30] Foreign Application Priority Data

Jun. 17, 1985 [JP] Japan .................................. 60-131394
Sep. 26, 1985 [JP] Japan .................................. 60-213420

[51] Int. Cl.$^5$ ................. C07D 499/00; A61K 31/425
[52] U.S. Cl. ..................................................... 540/310
[58] Field of Search ................. 540/310; 514/192, 193

[56] References Cited

U.S. PATENT DOCUMENTS

| | | | |
|---|---|---|---|
| 4,650,794 | 3/1987 | Christensen et al. | 540/310 |
| 4,729,990 | 3/1988 | Alpegiani et al. | 540/310 |
| 4,748,162 | 5/1988 | Leanza et al. | 540/310 |
| 4,863,914 | 9/1989 | Perrone et al. | 540/310 |
| 4,962,202 | 10/1990 | Sato et al. | 540/310 |

FOREIGN PATENT DOCUMENTS

| | | |
|---|---|---|
| 180490 | 10/1983 | Japan . |
| 89683 | 5/1984 | Japan . |
| 196895 | 11/1984 | Japan . |
| 63678 | 4/1986 | Japan . |
| 63679 | 4/1986 | Japan . |

OTHER PUBLICATIONS

Derwent Publication 83-760170/37.
Derwent Publication 85-2463531/24.
Derwent Publication 86-009084/02.

Primary Examiner—Nicholas S. Rizzo
Attorney, Agent, or Firm—Kerkam, Stowell, Kondracki & Clarke

[57] ABSTRACT

New derivatives of penem and pharmacutically acceptable salt thereof are herein disclosed; these compounds being useful as an antibacterial agent which has an extremely wide antibacterial spectrum, exhibits a high sensitivity to bacteria resistant to conventional penicillins and cephalosporin antibiotics and is excellent in its physico-chemical stability, solubility to water and biological stability, in particular, stability to decomposition by enzyme such as dehydropeptidase I in kidney, β-lactamase; these derivatives of penem being able to be prepared by reacting 2-substituted sulfinyl derivative of penem with a thiol compound and then optionally removing protective group(s) and further alkylating the reaction product or vice versa.

5 Claims, No Drawings

DERIVATIVES OF PENEM

This is a continuation of application Ser. No. 038,640, filed Apr. 15, 1987, which is a continuation-in-part application of Ser. No. 875,228, filed June 17, 1986, both now abandoned.

BACKGROUND OF THE INVENTION

1. Field of the Invention

The present invention relates to new derivatives of penem and pharmaceutically acceptable salts thereof having an excellent antibiotic activity.

2. Description of the Prior Art

In general, infectious diseases are caused by pathogenic microorganisms which are fixed in a certain portion of a living body and propagate therein and take place local reactions, when the microorganism accidentally penetrates into the living body and so forth. One of effective therapies for infectious diseases is to administrate an antibiotic to patients suffering from such disease. As such effective antibiotics conventionally used widely, there have been known such as penicillin, cephalosporin antibiotics having a wide antibacterial spectrum and these antibiotics have widely been used for treating various kinds of infectious diseases and exhibited an excellent effect.

Thus, in most of cases, the pathogenic microorganisms are eradicated by the action of a chemotherapeutic agent and patients are recovered. However, it is well known that a microorganism causing the corresponding infectious disease sometimes acquires resistance to the medicine, therefore if it is used for a long period of time and this becomes an inevitable problem in chemotherapy.

As a result, the antibiotics such as penicillin and cephalosporin antibiotics have not sufficiently been satisfiable in antibacterial spectrum, antibacterial activity, behavior in the body to which antibiotic is administered or safety, due to the appearance of the resistant bacteria during the long term and wide-spread application thereof.

Under such circumstances, an antibiotic called thienamycin was developed (see J. P. Laid-Open No. 73191/76), which shows sensitivity against bacteria resistant to penicillins and cephalosporin antibiotics and then studies on the synthesis of carbapenem derivatives and other penem derivatives having a skeletal structure similar to that of carbapenem have energetically been effected. However, these conventionally developed or synthesized carbapenem or penem antibiotics are not satisfied because of different drawbacks such that they are all physicochemically unstable and easily suffer from the enzymatic decomposition by emzymes such as dehydropeptidase in the kidney and further they have a rather low and insufficient solubility to water. Thus, there has not yet been developed even one highly valuable or effective medicine.

BRIEF EXPLANATION OF THE INVENTION

As mentioned above, it is quite effective to use antibiotics in the treatment of infectious diseases. However, there is a difficulty such as the appearance of the resistant bacteria which is inevitable problem involved in the chemotherapy utilizing antibiotics. That is, the antibiotics conventionally developed have gradually been insufficient in their antibacterial spectrum accompanied by the appearance of resistance bacteria. This problem is also encountered in the case of penicillins and cephalosporin antibiotics which have been expected to have relatively wide antibacterial spectrum and used widely.

Thus, there is a great demand for the development of a new medicine effective to these bacteria resistant to the antibiotics mentioned above and having a wide antibacterial spectrum and a various kind of materials have been proposed hitherto. However, none of them satisfies above mentioned requirements for these new medicine.

Therefore, the principle purpose of this invention is to provide new derivatives of penem.

Another purpose of the present invention is to provide new derivatives of penem effective to bacteria resistant to penicillins and cephalosporin antibiotics and having excellent physico-chemical properties.

A further purpose of this invention is to provide a method for preparing such new derivatives of penem.

The above mentioned and other purposes of the present invention can be accomplished by providing new derivatives of penem represented by the following general formula (I):

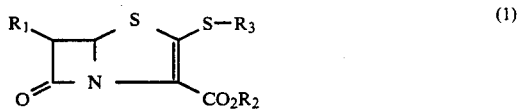

wherein substituent $R_1$ represents a hydrogen, a $C_1$-$C_6$ alkyl or a hydroxyl $C_1$-$C_6$ alkyl group; $COOR_2$ represents a carboxyl group or a carboxylate anion and $R_2$ may be an ester residue which may also act as a protective group simultaneously; and $R_3$ represents a substituted ($R_4$) or unsubstituted bicycloheterocyclic group of the following general formula:

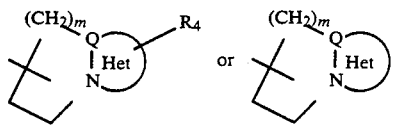

in which m is 1, 2 or 3, Q is —CH<,

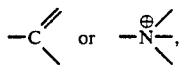

the partial structure of $R_3$ represented by the following general formula:

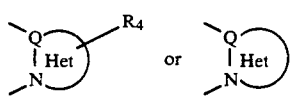

is a 5- or 6-membered nitrogen-containing heterocyclic ring or a quaternary nitrogen-containing heterocyclic ring, the nitrogen-containing hetero-cyclic ring being a saturated or unsaturated hetero-cyclic ring having 1 to 4 hetero atoms selected from the group consisting of oxygen, sulfur and nitrogen; $R_4$ represents a halogen, an amino, a hydroxyl, a cyano, an optionally substituted $C_1$-$C_6$ alkoxyl, an optionally substituted carbamoyl, an optionally substituted $C_1$-$C_6$ alkyl, an optionally substituted $C_2$–$C_6$ alkenyl, an optionally substituted $C_2$–$C_6$ alkynyl, an optionally substituted $C_3$–$C_6$ cycloalkyl, an optionally substituted $C_3$–$C_6$ cycloalkenyl, an optionally substituted $C_3$–$C_6$ cycloalkyl- $C_1$–$C_6$ alkyl, an optionally substituted $C_3$–$C_6$ cycloalkenyl- $C_1$–$C_6$ alkyl, an optionally substituted $C_3$–$C_6$ cycloalkenyl- $C_2$–$C_6$ alkenyl, an optionally substituted heterocyclyl (the heterocyclyl means three to seven membered cyclic group containing 1 to 6 carbon atoms and 1 to 4 hetero atoms selected from the group consisting of oxygen, nitrogen and sulfur, and includes both saturated and unsaturated forms unless otherwise defined), an optionally substituted heterocyclyl-$C_1$–$C_6$ alkyl, an optionally substituted heterocyclyl-$C_2$–$C_6$ alkenyl, an optionally substituted heterocyclyl-$C_2$–$C_6$ alkynyl, an optionally substituted $C_3$–$C_6$ cycloalkylidene- $C_1$–$C_6$ alkyl, an optionally substituted $C_3$–$C_6$ heterocyclylidene-$C_1$–$C_6$ alkyl, an optionally substituted aryl, an optionally substituted aryl- $C_1$–$C_6$ alkyl, an optionally substituted aryl- $C_2$–$C_6$ alkenyl, an optionally substituted aryl- $C_2$–$C_6$ alkynyl, or a group represented by the formula:

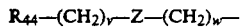
$$R_{44}-(CH_2)_v-Z-(CH_2)_w-$$

wherein Z is oxygen, sulfur, SO, $SO_2$, or NH, v is 0, 1, or 2, w is 0, 1, 2 or 3, and $R_{44}$ represents a halogen or a residue selected from the group consisting of, a $C_1$–$C_6$ alkyl, an aryl, a $C_2$–$C_6$ alkenyl, a heterocyclyl, a $C_2$–$C_6$ alkynyl, a heterocyclyl-$C_1$–$C_6$ alkyl, a $C_3$–$C_6$ cycloalkyl, a heterocyclyl-$C_2$–$C_6$ alkenyl, a $C_3$–$C_6$ cycloalkenyl, a heterocyclyl-$C_2$–$C_6$ alkynyl, and each residue is optionally substituted, the optional substituent on $R_4$ being at least one member independently selected from the group consisting of an amino, a mono-(optionally substituted) $C_1$–$C_6$ alkylamino, a di-(optionally substituted) $C_1$–$C_6$ alkylamino, a tri-(optionally substituted) $C_1$–$C_6$ alkylammonio, a halogeno, a carbonyl, a trifluoromethyl, a nitro, a hydroxyl, a formyl, a cyano, a formylamino, a carboxyl, an azido, a sulfo, an imino, a carbamoyl, a formamido, a mono or di-$_1$–$C_6$ alkylcarbamoyl, a carbamoyloxy, a mono or di-$C_1$–$C_6$ alkylcarbamoyloxy, an optionally substituted $C_1$–$C_6$ alkoxy, an optionally substituted $C_1$–$C_6$ alkoxycarbonyl, an optionally substituted $C_1$–$C_6$ alkylcarbonyloxy, an optionally substituted $C_1$–$C_6$ alkylthio, a sulfinyl, a mono or di-$C_1$–$C_6$ alkylsulfinyl, a sulfonyl, a mono or di-$C_1$–$C_6$ alkylsulfonyl, a sulfamoyl, a mono or di $C_1$–$C_6$ alkylsulfamoyl, a sulfinamoyl, a mono or di $C_1$–$C_6$ alkylsulfinamoyl, an optionally substituted $C_1$–$C_6$ alkylcarbonyl, an optionally substituted $C_1$–$C_6$ alkylcarbonylamino, an optionally substituted $C_1$–$C_6$ alkoxycarbonylamino, an optionally substituted phenylcarbonyl, an optionally substituted heterocyclylcarbonyl, an ureido, a mono or di-$C_1$–$C_6$ alkylureido, an amidino group represented by the formula:

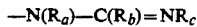
$$-N(R_a)-C(R_b)=NR_c$$

wherein $R_a$, $R_b$ and $R_c$ each represents a hydrogen or an optionally substituted $C_1$–$C_6$ alkyl or the two of them may form a $C_3$–$C_6$ cycloalkyl or heterocyclyl together, a carbamimidoyl group represented by the formula:

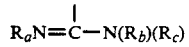
$$R_aN=C-N(R_b)(R_c)$$

wherein $R_a$, $R_b$ and $R_c$ are the same as defined above, a guanidinyl group represented by the formula:

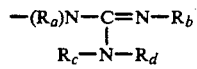
$$-(R_a)N-C=N-R_b$$
$$R_c-N-R_d$$

wherein $R_a$, $R_b$, $R_c$ and $R_d$ each represents a hydrogen or an optionally substituted $C_1$–$C_6$ alkyl or the two of them may form a $C_3$–$C_6$ cycloalkyl or heterocyclyl together, an optionally substituted phenyl, an optionally substituted heterocyclyl, a $C_1$–$C_6$ alkyl, and an optionally substituted $C_1$–$C_6$ alkyl wherein the substituent is selected from the group consisting of: an amino, a carboxyl, a cyano, a sulfo, a halogeno, a carbonyl, a trifluoromethyl, a nitro, a hydroxyl, a formyl, a mono-(optionally substituted) $C_1$–$C_6$ alkylamino, a di-(optionally substituted) $C_1$–$C_6$ alkylamino, a tert-(optionally substituted) $C_1$–$C_6$ alkylammonio, a carbamoyl, a mono or di-$C_1$–$C_6$ alkyl carbamoyl, a carbamoyloxy, a mono or di-$C_1$–$C_6$ alkyl carbamoyloxy, an amidino group represented by the formula:

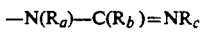
$$-N(R_a)-C(R_b)=NR_c$$

wherein $R_a$, $R_b$ and $R_c$ each represents a hydrogen neighboring two of them may form a $C_3$–$C_6$ cycloalkyl or a heterocyclyl together, a carbamimidoyl group represented by the formula:

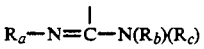
$$R_a-N=C-N(R_b)(R_c)$$

wherein $R_a$, $R_b$ and $R_c$ are the same as defined above: and pharmaceutically acceptable salts thereof.

DETAILED EXPLANATION OF THE INVENTION

The derivatives of penem represented by the general formula (I) according to the present invention show an extremely wide antibacterial spectrum and as a result they have a strong antibacterial activity against gram positive and negative bacteria and aerobic and anaerobic bacteria as well as the bacteria resistant to penicillins and cephalosporin antibiotics. Moreover, the derivatives of penem according to the present invention have a remarkable solubility to water and a good physicochemical stability and further they hardly suffer from decomposition by enzyme such as dehydropeptidase I of kidney or -lactamase. Thus, they can effectively be used as antibacterial medicine since they have a wide antibacterial spectrum and high biochemical stability and safety.

In the general formula (I), preferred penem derivatives or the salts thereof according to the present invention are those having the following substituents $R_1$, $R_2$ and $R_3$. First of all, the preferred examples of $R_1$ are hydrogen, a $C_1$–$C_6$ alkyl group such as methyl, ethyl, n-propyl, isopropyl or n-butyl which may have a hydroxyl group. Preferred $R_2$ may be a member selected from the group consisting of hydrogen, a linear or branched $C_1$–$C_6$ alkyl having 1 to 4 carbon atoms, such as methyl, ethyl, isobutyl, tert-butyl, a lower alkoxy $C_1$-$C_6$ alkyl such as methoxymethyl, methoxyethyl, a lower aliphatic acyloxymethyl such as pivaloyloxymethyl, phthalidyl, 5-$C_1$-$C_6$ alkyl-1, 3-dioxol-2-one-4-yl methyl. The substituent $R_2$ may also act as the group for protecting carboxyl group when preparing the derivatives of the present invention and may be an ester residue, easily removable under a mild condition, for example, aralkyl such as o-nitrobenzyl, p-nitrobenzyl, benzhydril or 2-naphthylmethyl, allyl or a $C_1$-$C_6$ alkyl silyl such as trimethyl silyl.

Moreover, $COOR_2$ may be a carboxylate anion depending on the kind of the substituent $R_3$ of the derivative according to this invention, which corresponds to the case where the carboxyl group situated at 3-position of penem is in the form of carboxylate anion as the counter ion of $R_3$. For instance, if $R_3$ is a quaternary nitrogen containing heterocyclic ring, the carboxyl group at 3-position may be in the form of a carboxylate anion which is a counter ion thereto. In addition, if the derivatives are salts with strong acids, in other words when the counterion of quaternary nitrogen is an anion of strong acid, $R_2$ may be hydrogen, and therefore in this case the derivatives have characteristic properties as if it were a betaine compound (quaternary ammonium compound). Thus, the acid addition salts of the compounds (I) may be represented by the following general formula:

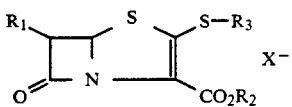

wherein $X^-$ means an anion of an acid.

While if $R_3$ is a basic group, $COOR_2$ may be either carboxyl or carboxylate anion depending on the conditions of environment (in particular pH) surrounding the compounds, or $COOR_2$ may be in a equilibrium state between these two states. This means that the derivative may be in the form of so-called zwitter ion and therefore, it should be understood that the compound of the formula (I) includes such compounds having a zwitter ionic structure.

The preferred examples of substituent $R_4$ include the followings (in the formula, m means 1, 2 or 3, n means 1, 2, 3, 4, 5 or 6, v means 0, 1 or 2, w means 0, 1, 2 or 3, Y means O, S or NH, $Y_1$, $Y_2$, $Y_3$ and $Y_4$ each means N, NH, O or S):

a $C_1$-$C_6$ alkyl such as methyl, ethyl, ispropyl and butyl,
a $C_2$-$C_6$ alkenyl such as vinyl, allyl, isopropenyl, 1-propenyl, 2-butenyl and 1, 3-butadienyl,
a $C_2$-$C_6$ alkynyl such as ethynyl, propargyl and 2-butynyl,
a $C_3$-$C_6$ cycloalkyl such as cyclopropyl, cyclobutyl, cyclopentyl and cyclohexyl,
a $C_3$-$C_6$ cycloalkyl $C_1$-$C_6$ alkyl such as cyclopropylmethyl, cyclopropylethyl, cyclopropylisopropyl, cyclopentylmethyl and a group represented by the formula:

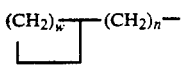

a $C_3$-$C_6$ cycloalkenyl such as the formula:

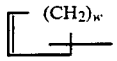

a $C_3$-$C_6$ cycloalkenyl $C_1$-$C_6$ alkyl such as the formula:

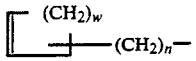

a saturated heterocyclyl such as the formula:

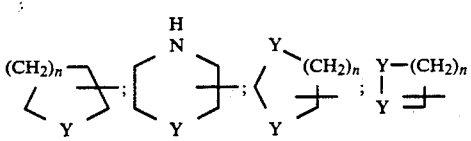

a saturated heterocyclyl $C_1$-$C_6$ alkyl such as the formula:

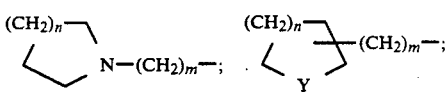

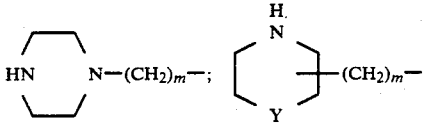

an unsaturated (nonaromatic) heterocyclyl such as the formula:

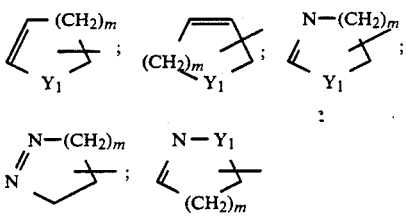

an unsaturated (nonaromatic) heterocyclyl $C_1$-$C_6$ alkyl such as the formula:

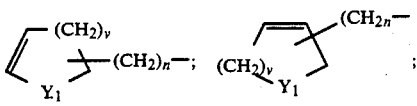

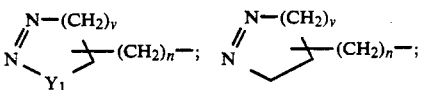

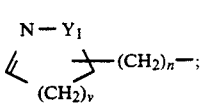

an unsaturated (aromatic) heterocyclyl such as the formula:

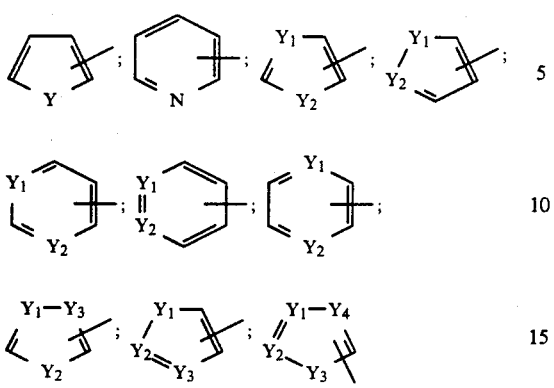

an unsaturated (aromatic) heterocyclyl $C_1$-$C_6$ alkyl such as the formula:

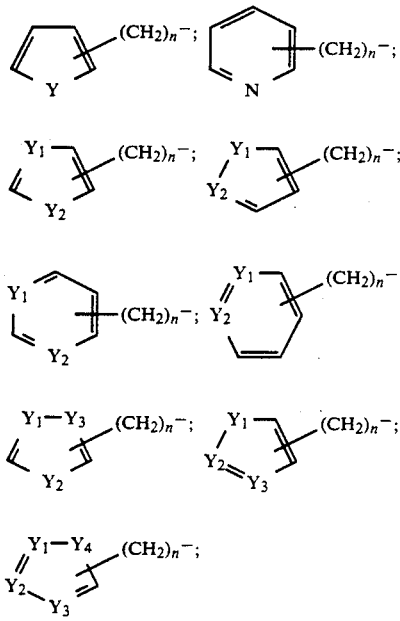

a heterocyclylidene $C_1$-$C_6$ alkyl such as the formula:

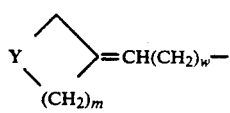

a cycloalkylidene $C_1$-$C_6$ alkyl such as the formula:

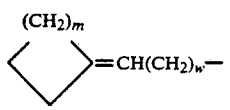

Preferred examples of the penem derivatives according to the present invention are such that the substituents $R_3$ is a member selected from the group consisting of groups represented by the formula:

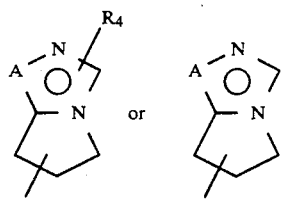

wherein A is nitrogen or carbon and $R_4$ has the same meaning as defined above and more preferably, $R_4$ is selected from the group consisting of —$CH_3$, —$CH_2CH_3$, —$(CH_2)_3CH_3$,

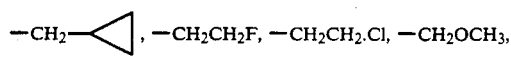

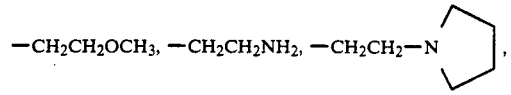

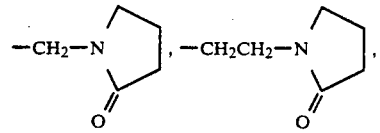

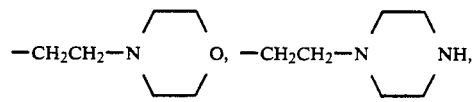

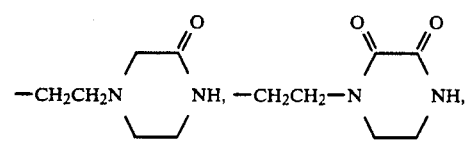

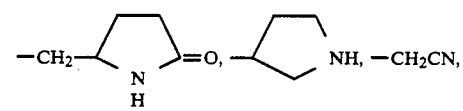

—$CH_2CH_2CN$, —$CH_2$—C≡CH, —$CH_2$C≡C—$CH_3$,

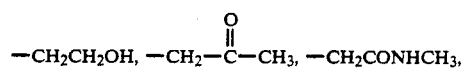

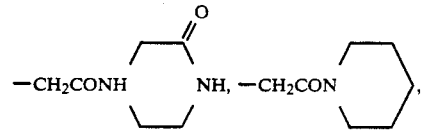

-continued

—CH$_2$CON(piperazine)NH, —CH$_2$CON(imidazolidinone)NH,

—CH$_2$CONHOH, —CH$_2$CONHOCH$_3$, —CH$_2$COCH$_2$COOCH$_3$,

—CH$_2$COCH=CH$_2$, —CH$_2$COCH$_2$OH, —CH$_2$COCH$_2$CN,

—CH$_2$COCH$_2$CONH$_2$, —CH$_2$COCH$_2$NH$_2$, —CH$_2$CHO,

—CH$_2$COOCH$_3$, —CH$_2$COOH, —CH$_2$COCONH$_2$,

—CH$_2$COCOOCH$_3$, —CH$_2$COCOOH, —CH$_2$COCHO,

—CH$_2$SO$_2$NH$_2$, —CH$_2$SCH$_3$, —CH$_2$SOCH$_3$, —CH$_2$SO$_2$CH$_3$,

—CH$_2$CONHSO$_2$CH$_3$, —CH$_2$CONHSO$_2$NH$_2$,

—CH$_2$SO$_2$NHCOCH$_3$, —CH$_2$CO—(phenyl),

—CH$_2$CO—(aminophenyl), —CH$_2$CONH—(thiazolyl),

—CH$_2$—(phenyl), —CH$_2$—(fluorophenyl),

—CH$_2$CH$_2$O—(fluorophenyl), —CH$_2$—(thienyl),

—CH$_2$—(furyl), —CH$_2$—(pyrrolyl), —CH$_2$—(oxazolyl),

—CH$_2$—(imidazolyl), —CH$_2$—(thiazolyl), —CH$_2$—(thiazolyl),

—CH$_2$—(oxazolyl), —CH$_2$—(isoxazolyl), —CH$_2$—(N-methylimidazolyl),

—CH$_2$—(N-methylimidazolyl), —CH$_2$—(N-methyltriazolyl), —CH$_2$—S—(N-methylthiadiazolyl), —CH$_2$—S—(thiadiazolyl), —CH$_2$—S—(N-methyltetrazolyl), —CH$_2$—S—(thiadiazolyl), —CH$_2$—S—(imidazolyl with N—CH$_3$), —CH$_2$CH$_2$—N$^{\oplus}$(pyridinium), —CH$_2$CH$_2$—N$^{\oplus}$(thiazolium)S.

In the penem derivatives of the invention, the preferred are those having the following bycycloheterocyclic group (R$_3$) in which m equals to 1:

[Structures of various bicyclic heterocyclic groups with R$_4$ substituents]

-continued

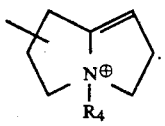

Among the penem derivatives of the formula (I), those having the substituent $R_3$ including an asymmetric carbon or carbons, contain stereoisomers. For instance, when there is one asymmetric carbon atom in $R_3$, two isomers should be present. Then, one of them will hereunder be referred to "isomer A" and the other referred to "isomer B". Moreover, in the case where $R_3$ has an asymmetric carbon atom as well as substituent $R_4$, position isomers may be present other than stereoisomers. In such case, they are expressed as "isomer A" to "isomer D" and so forth.

In the general formula (I), it is preferred that the steric configuration of the carbon atom at 5-position should be in R configuration which corresponds to that of natural penicillin and that there may be mentioned such as hydrogen and 1-hydroxy-ethyl group as the preferred examples of substituent $R_1$. The most preferred are such that the steric configuration of carbon atom at 6-position to which $R_1$ such as 1-hydroxyethyl group is bonded is in S configuration and that the steric configuration of the carbon atom at 8-position to which hydroxyl group is attached is in R configuration as in the case of thienamycin.

Furthermore, the most preferred substituent $R_2$ is hydrogen or an anion charge and the preferred examples of ester residue metabolisable are such as pivaloyloxymethyl, phthalidyl, 5-methyl-1, 3-dioxol-2-one-4-yl methyl. Groups such as p-Nitrobenzyl, allyl may preferably be used as the protective group for carboxyl group of the compound (I) when preparing the same.

In addition, the compound according to the present invention and a certain intermediates thereof may be in the form of tautomerism. Therefore, the scope of this invention is appreciated to include such tautomeric form, although the structural formula herein disclosed has not been described so as to include such structures.

As the preferred examples of $R_3$, there may be mentioned such as:

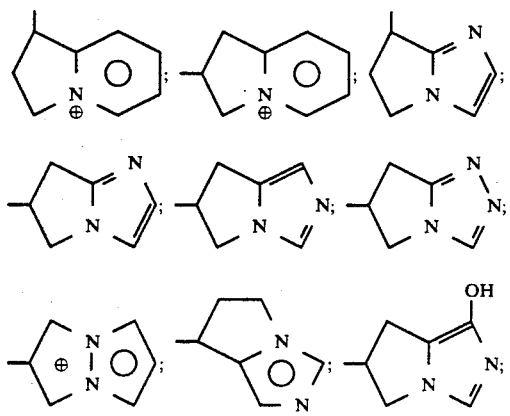

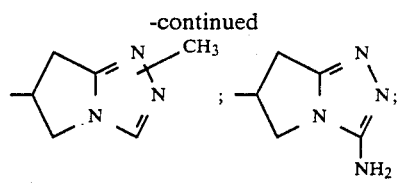

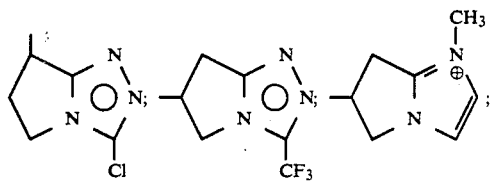

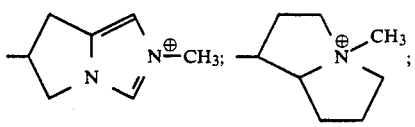

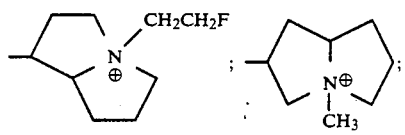

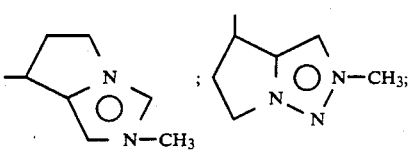

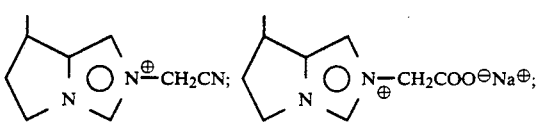

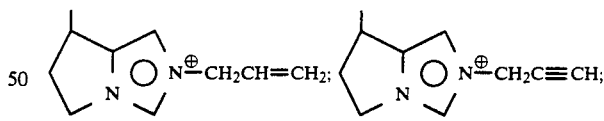

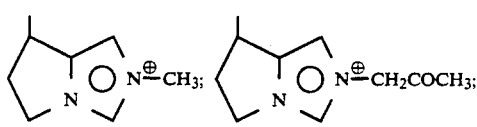

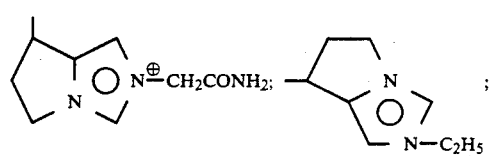

Thus, most preferred penem derivatives according to the present invention are those represented by the following general formulas:

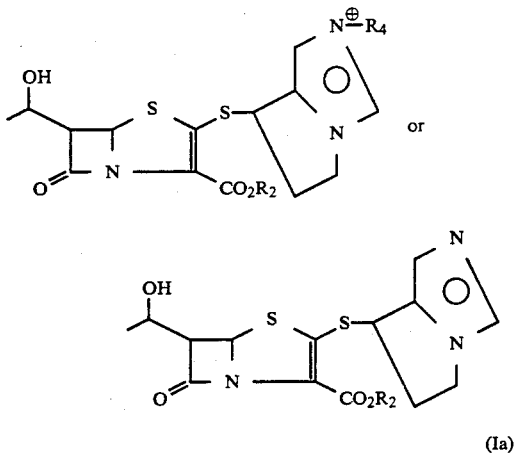

(Ia)

wherein $R_2$ is H or $COOR_2$ means a carboxylate anion, $R_4$ is $-CH_3$, $-C_2H_5$, $-CH_2CN$, $-CH_2-\equiv CH$, $-CH_2-CO-CH_3$, or $-CH_2-CO-NH_2$;

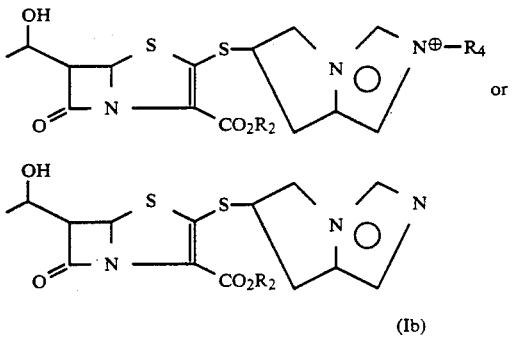

(Ib)

wherein $R_2$ is hydrogen or represents carboxylate anion as $COOR_2$ and $R_4$ is methyl; and

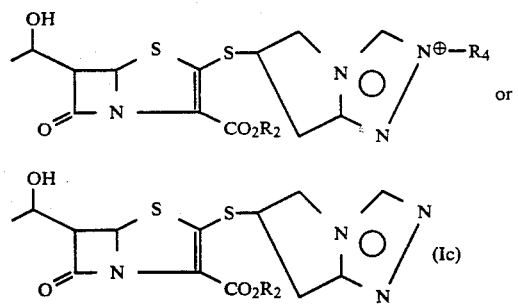

(Ic)

wherein $R_2$ is H or represents carboxylate anion as $COOR_2$ and $R_4$ is methyl group.

Salts of the compound (I) of the present invention include non-toxic salts of carboxylic acid derivative (in the formula (I), $COOR_2=COOH$) for instance metal salt such as sodium, potassium, aluminum, magnesium salt; ammonium salt; salts with a non-toxic amine such as triethylamine, procain, benzylamine and other amines used to form salts with penicillins and cephalosporins. Most preferred salts are sodium and potassium salts.

While, the penem derivatives of the present invention also include a basic group and therefore, pharmaceutically acceptable acid addition salts with, for instance, mineral acids such as hydrochloric acid, hydrobromic acid, phosphoric acid, sulfuric acid; organic acids such as acetic acid, citric acid, succinic acid, ascorbic acid, methane sulphonic acid may also be possible. The compound (I) according to the present invention may be in the form solvated in various degree, for example, hydrates and they also fall within the scope of this invention.

The compounds of the present invention may be combined with pharmaceutic carrier, stabilizer, solubilizing agents, adjuvant conventionally used, according to any known techniques to form preparations.

The pharmaceutical preparations of the present invention may be administered through various manner such as oral administration, intravenous injection, intramuscular injection, or parenteral administration. They are preferably in the form of unit dose suitable to a particular mode of administration. Therefore, they may be in the form of tablets, pills, capsules, granules, injections, suppository or the like known per se. The daily dose of the compound of this invention, in general, falls within the range of 250 mg to 3,000 mg with respect to adult, which are subjected to divided administration. However, the dose may vary depending on various factors such as age, sex, conditions to be treated.

On some of the compounds according to the present invention, the antibacterial activity was determined by broth dilution method in Muller-Hinton broth in which $10^5$/ml of bacteria were seaded and incubated at 37° C. for 18 hours. The results obtained are summarized in the following Table I:

TABLE I

| | Minimal Inhibitory Concentration (MIC: μg/ml) | | |
|---|---|---|---|
| | Compound Examined | | |
| Bacteria Tested | A | B | Sch 34343 (comparative) |
| E. coli, NIHJ | ≦0.05 | 0.1 | 0.39 |
| Ent. cloacae, 03400 | 0.39 | 0.2 | 0.78 |
| Ser. Marcescens, 10104 | 0.78 | 0.78 | 3.13 |
| Ps. aeruginosa, 32233 | 25 | 0.78 | 100 |
| S. aureus, 209P | ≦0.05 | ≦0.05 | 0.1 |

A: (5R, 6S, 8R)-6-(1-hydroxyethyl)-2-[(6,7-dihydro-5H-pyrrolo [2,1-c]-1,2,4-triazol-6-yl)-thio]-2-penem-3-carboxylic acid (Isomers A, B)
B: (5R, 6S, 8R)-6-(1-hydroxyethyl)-2-[(6,7-dihydro-2-methyl-5H-pyrrolo [1,2-c] imidazolium-7-yl)-thio]-2-penem-3-carboxylate (Isomer A)
Sch 34343: Developed and proposed by Scheering Company represented by the following formula:

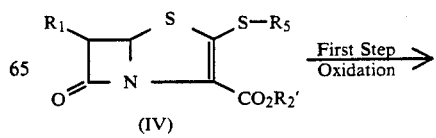

which has been known as an effective penem compound and the excellent results of clinical testing are reported.

The penem derivatives of the present invention can effectively and easily be prepared according to a method such as described in the following reaction scheme.

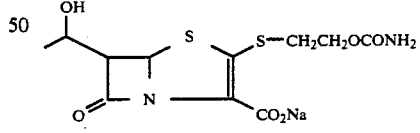

(IV)

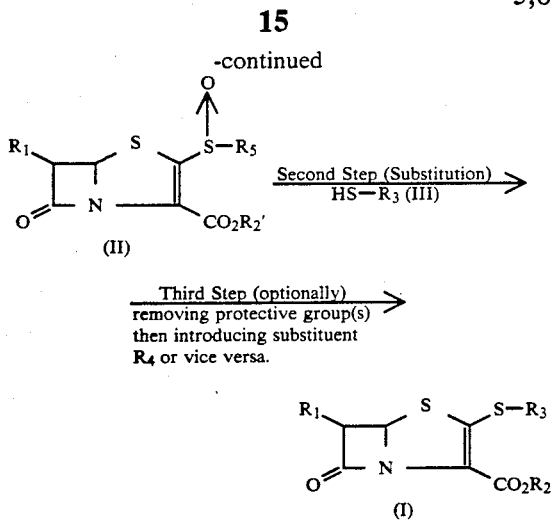

(i) First Step

The starting material (IV), which is one of penem derivative, may easily be prepared according to a known method (see, for example, J. Am. Chem. Soc., 1982, 104, 138) or an improved method thereof. In the formula (IV), $R_1$ has the same meaning as defined above, $R_2'$ is an ester residue disclosed above in the definition of $R_2$ and $R_5$ represents an organic group, for instance, an alkyl, preferably $C_1$-$C_6$ alkyl such as ethyl, n-propyl, isopropyl, an aryl such as phenyl, tolyl, an aralkyl such as benzyl, methyl benzyl, chlorobenzyl, phenethyl.

The penem derivative (IV) is oxidized, in a suitable medium, with an oxidizing agent such as perbenzoic acid, m-chloro-perbenzoic acid, peracetic acid, hydrogen peroxide, selenium dioxide, ozone or sodium metaperidic acid, preferably m-chloro-perbenzoic acid, to form sulfoxide derivatives (II) in a high yield (in the formula (II), a wavy arrow attached to sulfur atom means the fact that the resulting compound comprises a mixture of stereoisomers). The resulting sulfoxide derivative composed of mixed isomers may suitably be used in the subsequent second step without carrying out the separation of isomers. As the solvent which may be used in this reaction, there may be mentioned such as halogenated hydrocarbons, for instance, dichloromethane, chloroform, carbon tetrachloride; alcohols such as methanol, ethanol; ketones such as acetone, methylethylketone; acetic acid; pyridine, N,N-dimethylformamide (hereunder referred to as DMF), acetamide, dimethylsulfoxide (hereunder referred to as DMSO), water, phosphate buffer and a mixture thereof. Preferred examples thereof include solvents which do not have a harmful effect on reactants and reaction products. The first step can be carried out at a temperature of from $-50°$ C. to 50° C., however, it is preferable to carry out the reaction at a rather mild temperature condition such as $-30°$ C. to room temperature. The first step is, in general, continued for 5 minutes to 4 hours, however, it is usually sufficient to continue the reaction for 30 minutes to 1 hour.

(ii) Second Step

In this step, the sulfoxide derivative (II) obtained in the first step is subjected to a substitution reaction with a thiol compound (III) (in which $R_3$ is the same as defined above) or an acid addition salt or an reactive derivative thereof. In this step, organic solvent such as DMF, DMSO, tetrahydrofuran (hereunder referred to as THF), hexamethylphosphotriamide (hereunder referred to as HMPA) and a mixture thereof which do not affect on reactants and products, can be used as the reaction medium. The reaction temperature, in general, falls within the range of from $-50°$ C. to room temperature, preferably $-30°$ C. to 0° C. While the reaction period generally falls within the range of from 15 minutes to 2 hours, in particular, 30 minutes to 1 hour.

The reactivity of the thiol compound (III) may be improved by coexisting a base during reaction procedure and thus, the reaction proceeds in good rate and yield. However, it is a matter of course that the reaction proceeds without a base. As such base, there may be mentioned such as alkylamines, for example, triethylamine, diisopropylethylamine; alicyclic amines such as 1,8-diaza-bicyclo [5,4,0]-7-undecene (hereunder referred to as DBU), N-methylmorpholine; inorganic bases such as hydroxide and carbonate of sodium and potassium; metal alcoholates such as potassium tert-butoxide, sodium methoxide; sodium amide, sodium hydride and among others, diisopropylethyl amine and DBU are preferably used.

Examples of reactive derivatives of thiol compound (III) include thiolate compounds represented by the general formula (III'):

$$MS-R_3 \qquad (III')$$

wherein M is an alkali metal and $R_3$ has the same meaning as define above. In this substitution reaction, the thiol compound of the formula (III) or acid addition salt or active derivative thereof is, in general, used in an amount of from 1 to 3 eq. with respect to the sulfoxide derivative (II), preferably 1 to 2 eq. While the base is preferably used in an amount equivalent to that of thiol compound (III). When the thiol compound (III) is an acid addition salt thereof, the excellent result may be expected to use the base in an excess amount such that the added acid may be neutralized.

The product resulting from the above substitution reaction may be isolated according to any one of conventional post-treatments.

(iii) Third Step

If the resulting product substituted has a protective group, the group may eventually be removed. The removal of the protective group may be effected according to reductive decomposition by hydrogenation, chemical reduction, hydrolysis with an acid, a base or an enzyme or the like.

When $R_2$ in the formula (I) is an ester residue in particular, p-nitrobenzyl, benzhydryl, 2-naphthylmethyl or the like, the removal of protective group can effectively be carried out by catalytic reduction utilizing palladium supported by carbon, platinum oxide or any one of other known catalysts to obtain penem derivatives represented by the formula (I) in which $COOR_2$ is carboxyl group or carboxylate anion. In this step, reaction solvent such as dioxane, THF, water, a buffer or a mixture thereof, in particular, water-containing THF, water-containing dioxane, phosphate buffer-THF mixture may be utilizable, and the reaction is effected under a hydrogen pressure of 1 to 4 atms, at a temperature of from 0 to 50° C., preferably 10 to 30° C. for 30 minutes to 16 hours, preferably 1 to 4 hours. While if $R_2$ in the formula (I) is p-nitrobenzyl group, the removal of the protective group is effected by reacting the product with ammonium chloride aqueous solution and iron powder, in a water soluble solvent such as THF, dioxane; if $R_2$ is allyl group, it may be removed by reacting the product with tetrakistriphenylphosphine palladium (0), triphenylphosphine and 2-ethylhexanoic acid in an aprotic solvent such as THF, methylene chloride; when $R_2$ is 2,2,2-trichloroethyl group, it may also be removed by reducing the product with zinc powder and thus, the objective product, in which $COOR_2$ is carboxyl or carboxylate anion depending on the case, can be prepared.

Some of the products resulting from the substitution reaction (the step (ii)) may eventually be difficult to isolate them from each other because of their properties. Therefore, if it is intended to obtain compounds (I) in which $COOR_2$ is carboxyl or carboxylate anion, a good result can often be attained by removing the protective group in the same reactor as used to carry out the reaction without isolating the intermediate product resulting from the substitution reaction or removing it after subjecting the product to a simple currently used post-treatment. This is a particularly simple method and provides an excellent yield and quality of the product obtained. In addition, it permits the formation of objective product in a large scale without employing complex operations.

As seen from the above, the resulting product, in the third step may further be subjected to introduction of the substituent $R_4$, according to need, to obtain penem derivatives (I) in which $R_3$ is a quaternary nitrogen-containing heterocyclic group. The introduction of $R_4$ may be effected according to any one of conventional techniques, for example, alkylation in which conventional alkylating agents such as $C_1$-$C_6$ alkyl halides, for instance, methyl iodide, ethyl iodide; bromofluoroethane, dimethyl sulfate or diethyl sulfate is used and other identical techniques using, for example, a halide of the corresponding $R_4$. Moreover, preferred examples of solvent for alkylation reaction are acetone, acetonitrile, THF, dioxane or the mixture thereof. However, the compound having the substituent $R_4$ may be prepared by a process other than the third step using a raw-material HS-$R_3$ (III) in which $R_4$ was preliminarily introduced.

When $R_3$ in the formula (I) is a quaternary nitrogen-containing heterocyclic group, the objective compounds can be obtained, in a good yield, by alkylating the product of the step (ii) and then removing the protective group according to need.

The objective compounds of the formula (I) thus prepared may be isolated and purified according to any one of conventional techniques. That is, the product is, for example, isolated by extraction and concentration, and then it can be purified according to recrystallization, reprecipitation, chromatography. In general, the compounds (I) may be crystallized to purify the same. For this purpose, it is effective or preferable to convert the compound to its salt form. In this case, the salt must not be non-toxic acid addition salt. The product is first crystallized as a toxic salt to purify and then the acid is removed or the toxic salt is exchanged to pharmaceutically acceptable salt (this can be effected by exchanging counterions in the case of quaternary ammonium salt), whereby a high purity objective compound may be prepared.

Esters, which may be expected to be metabolized in a living body, may be prepared according to a method which is usually employed to form esters of penicillins or cephalosporins, which comprises esterifying the compounds (I) in which the substituent $COOR_2$ thereof is carboxyl or carboxylate anion.

In the present invention, the thiol compounds represented by the general formula (III) already disclosed are also new compounds and useful as the intermediate compounds for preparing penem derivatives of the formula (I). Therefore, it should be appreciated that these intermediate compounds fall within the scope of this invention.

The invention will now be explained in more detail with reference to the following illustrative examples In the following examples and reference examples, the following abbreviations are used for simplicity PNB p-nitrobenzyl; PMB: p-methoxybenzyl; Me: methyl; Et: ethyl; Ar: phenyl; Ts: p-toluene sulfonic acid residue; BOC: tert-butoxycarbonyl

EXAMPLE 1

Synthesis of Isomers A and B of (5R, 6S, 8R)-2-[(6,7-dihydro-5H-pyrrolo[1,2-c]imidazol-7-yl)thio]-6-(1-hydroxyethyl)-2-penem-3-carboxylic acid

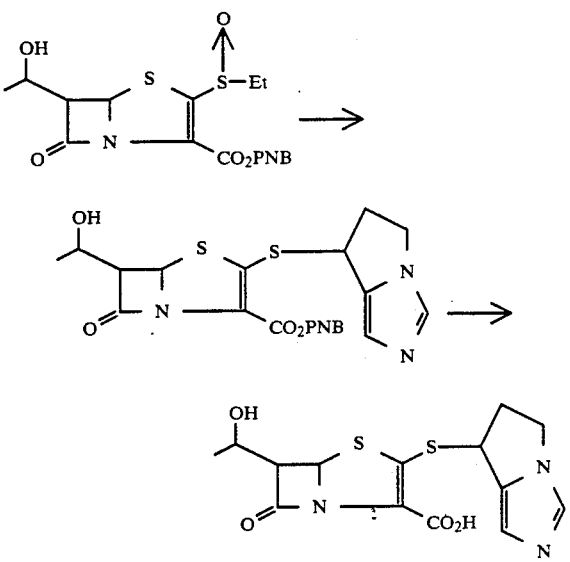

(1) Preparation of p-nitrobenzyl (5R, 6S, 8R)-2-[(6,7-dihydro-5H-pyrrolo[1,2-c]imidazol-7-yl)thio]-6-(1-hydroxyethyl)-2-penem-3-carboxylate 256mg of p-nitrobenzyl (5R, 6S, 8R)-2-ethylsulfinyl-6-(1-hydroxyethyl)-2-penem-3-carboxylate was dissolved in 2ml of DMF and cooled to $-40°$ C. Then, to the solution obtained there were added, with stirring, 440mg of 6,7-dihydro-7-mercapto-5H-pyrrolo [1,2-c]imidazole trifluoromethane sulfonate (obtained in the reference example 1 hereunder described) in 2ml of DMF and 0.54 ml of diisopropylethylamine and the solution was stirred for 30 minutes. To the reaction solution, 100 ml of ethyl acetate was added, and washed with water, then with saturated sodium chloride aqueous solution, dried over $Na_2SO_4$, thereafter concentrated in vacuo. The resulting residue was purified by chromatography using a column packed with 10 g of silica gel (elute: chloroform/methanol mixture; 96:4 v/v) and the objective compound was obtained as yellow oil (yield: 290mg).

N. M. R. δ(CDCl₃)ppm: 1.37 (3H; d; J=6Hz; —CH₃), 2.40~3.00 (1H; m), 3.00~3.50 (1H; m), 3.70~3.90 (1H; m; C₆—H), 4.00~4.40 (3H; m), 4.70~4.90 (1H; m), 5.30 (2H; ABq; J=14Hz; —OCH₂Ar), 5.78 (1H; brs; C₅-H), 6.96 and 6.99 (1H; s;

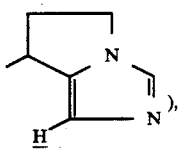

7.48 (1H; s;

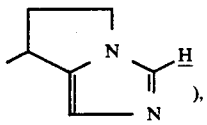

7.57 (2H; d; J=9Hz; 2×ArH), 8.15 (2H; d, J=9Hz; 2×ArH)

(2) Synthesis of (5R, 6S, 8R)-2-[(6,7-dihydro-5H-pyrrolo[1,2-c]imidazol-7-yl)thio]-6-(1-hydroxyethyl)-2-penem-3-carboxylic acid (Isomers A and B)

The compound (145 mg) obtained in the step (1) was dissolved in the mixture of 10 ml of THF and 10 ml of phosphate buffer (pH 7), 150 mg of carbon bearing 10% of palladium was added and catalytically reduced for 2 hours under 1 atm. of hydrogen pressure. The catalyst was filtered off and the filtrate and the wash liquid were washed with ether. The water phase was concentrated to about 20 ml in volume and purified by column chromatography packed with Diaion HP-20 (column size: 20×300mm). The fractions eluted with water were disposed and the fractions (showing UV absorption band at λ_max=324 mm) eluted with 5% THF-water were combined and concentrated in vacuo. The concentrate obtained was subjected to high performance liquid chromatography (HPLC) [carrier: Nucleosil 7C₁₈ (10×300 mm); solvent: 5% acetonitrile-water; flow rate: 5 ml/min.]and recovered fractions containing objective product, corresponding to the retention time of 10 minutes and 13.5 minutes which provide pale yellow powder of the objective compound after evaporation in vacuo and lyophilization.

Isomer A

Yield 19 mg
I. R. (KBr disc) cm⁻¹: 1770, 1580
U. V. λ_max (H₂O)nm: 250 (sh), 324
N. M. R. δ(D₂O)ppm: 1.39 (3H; d; J=6Hz: —CH₃), 2.6~3.05 (1H; m), 3.1~3.6 (1H; m), 4.04 (1H; dd; J=2, 6Hz; C₆-H), 4.19~4.63 (3H; m), 4.80 (HOD), 4.99~5.17 (1H; m), 5.81 (1H; d; J=2Hz; C₅-H), 7.44 (1H; s; imidazole-H), 8.61 (1H; s; imidazole-H)
HPLC (retention time): 10 min.

Isomer B

Yield 22 mg
I. R. (KBr disc)cm⁻¹: 1770, 1580
U. V. λ_max (H₂O) nm: 258, 324
N. M. R. δ(D₂O) ppm: 1.38 (3H; d; J=6Hz; —CH₃), 2.60~3.00 (1H; m), 3.05~3.51 (1H; m), 4.02 (1H; dd; J=2, 6Hz; C₆-H), 4.17~4.63 (3H; m), 4.80 (HOD), 4.97~5.13 (1H; m), 5.81 (1H; d; J=2Hz; C₅-H), 7.48 (1H; s; imidazole-H), 8.63 (1H; s; imidazole-H)
HPLC (retention time): 13.5 min.

EXAMPLE 2

Synthesis of (5R, 6S, 8R)-2-[(6,7-dihydro-2-methyl-5H-pyrrolo[1,2-c]imidazolium-7-yl)thio]-6-(1-hydroxyethyl)-2-penem-3-carboxylate (isomers A and B)

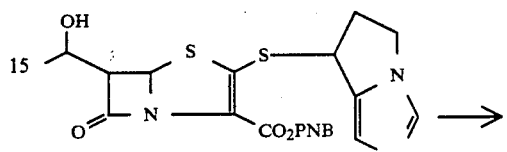

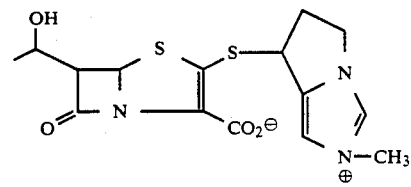

The compound (145 mg) obtained in the step (1) of the example 1 was dissolved in the mixture of THF (3 ml) and acetone (10 ml), 0.37 ml of methyl iodide was added to the solution and kept standing at 5° C. for 30 hours. The reaction solution was evaporated under reduced pressure, and the residue was washed with ether and dried. The resulting powder was dissolved in the mixed solvent consisting of THF (10 ml) and water (10 ml), then 2.5 g of ammonium chloride and 1.24 g of iron powder (100 mesh) were added while stirring under ice cooling and stirred vigorously for one hour at that temperature. Insolubles formed were filtered off and the filtrate was washed with ethyl acetate. The aqueous phase was evaporated to approximately 20 ml in volume and purified by column chromatography utilizing Diaion HP-20 (20×400 mm). After removing the fraction eluted with 150 ml of water, the fractions eluted with 5% THF-water were recovered, concentrated under reduced pressure, subjected to HPLC [carrier: Nucleosil 7C₁₈ (10×300 mm); solvent: 7% acetonitrile-water; flow rate: 4 ml/min.]and recovered the fractions, the retention time of which are 11 and 13.5 minutes respectively, containing objective products. Thus, the compound mentioned above was obtained as pale yellow powder after the evaporation in vacuo and lyophilization.

Isomer A

Yield 14 mg
I. R. (KBr disc)cm⁻¹: 1760, 1580
U. V. λ_max (H₂O)nm: 250 (sh), 325
N. M. R. δ(D₂O)ppm: 1.38 (3H; d; J=6Hz; —CH₃), 2.63~3.02 (1H; m), 3.08~3.55 (1H; m), 3.96 (3H; s; —NCH₃), 4.04 (1H; dd; J=2, 6Hz, C₆-H), 4.16~4.60 (3H; m), 4.80 (HOD), 4.96~5.13 (1H; m), 5.79 (1H; d; J=2Hz, C₅-H), 7.47 (1H; s; imidazole-H), 8.70 (1H; s; imidazole-H)
HPLC (retention time): 11 min.

Isomer B

Yield 17 mg

I. R. (KBr disc)cm$^{-1}$: 1760, 1595

U. V. $\lambda_{max}$ (H$_2$O)nm: 260, 325

N. M. R. $\delta$(D$_2$O)ppm: 1.38 (3H; d; J=6Hz; —CH$_3$), 2.55~2.90 (1H; m), 3.00~3.50 (1H; m), 3.96 (3H, s; —NCH$_3$), 4.02 (1H; dd; J=2, 6Hz, C$_6$-H), 4.16~4.60 (3H; m), 4.80 (HOD), 4.95~5.12 (1H; m), 5.80 (1H; d; J=2Hz; C$_5$-H), 7.51 (1H; s; imidazole-H), 8.70 (1H; s; imidazole-H)

HPLC (retention time): 13.5 min.

EXAMPLE 3

Synthesis of (5R, 6S, 8R)-2-[(6,7-dihydro-2-(2-oxopropyl)-5H-pyrrolo[1,2-c]imidazolium-7-yl)thio]-6-(1-hydroxyethyl)-2-penem-3-carboxylate (isomers A and B)

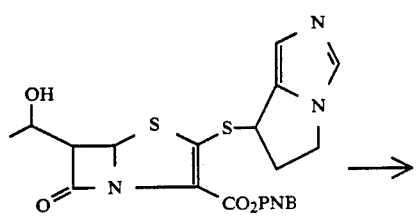

→

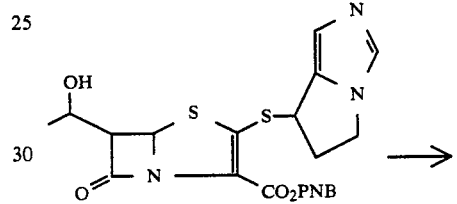

The product (200 mg) obtained in the step (1) of the example 1 was dissolved in acetone (15 ml) and stirred for 4 hours after the addition of 0.69 ml of bromoacetone. After the evaporation of solvent, the residue obtained was washed with ether and dried. The resulting solid was dissolved in 25 ml of 50% THF-water mixture, mixed with 3.6 g of ammonium chloride and 1.8 g of iron powder and stirred for 1.5 hours under ice cooling. The solution was evaporated to about 5 ml under reduced pressure after removing insolubles by filtration. The concentrate was passed through a column packed with Diaion HP-20 (manufactured and sold by MITSUBISHI CHEMICAL INDUSTRIES LTD.) and the fraction eluted with 5% THF-water was further purified by HPLC to obtain the objective compounds.

Conditions of HPLC

Carrier: Nucleosil 7C$_{18}$ (10×300 mm)

Flow rate: 3.65 ml/min.

Solvent: 7% acetonitrile-water

Isomer A

Yield 45 mg

I. R. (KBr disc)cm$^{-1}$: 3410, 2940, 1770, 1590, 1360

U. V. $\lambda_{max}$ (H$_2$O)nm: 248 (sh), 325

N. M. R. $\delta$(D$_2$O)ppm: 1.33 (3H; d; J=6.6Hz; —CH$_3$), 2.36 (3H; s), 2.6~3.0 (1H; m), 3.0~3.6 (1H; m), 3.99 (1H; dd; J=1.4Hz, 6.1Hz; C$_6$-H), 4.29 (1H; t; J=6.1Hz; C$_8$-H), 4.3~4.8 (2H; m), 4.74 (DOH), 4.8~5.1 (1H; m), 5.35 (2H; s), 5.73 (1H; d; J=1.4Hz; C$_5$-H), 7.37 (1H; s; side chain C$_1$-H), 8.67 (1H; s; side chain C$_3$-H)

HPLC (retention time): 19 min.

Isomer B

Yield 54 mg

I. R. (KBr disc)cm$^{-1}$: 3400, 2960, 1765, 1590, 1360

U. V. $\lambda_{max}$ (H$_2$O)nm: 259 (sh), 324

N. M. R. $\delta$(D$_2$O)ppm: 1.33 (3H; d; J=6.3Hz; —CH$_3$), 2.37 (3H; s), 2.5~2.9 (1H; m), 2.9~3.5 (1H; m), 3.97 (1H; dd; J=1.4Hz, 6.1Hz; C$_6$-H), 4.29 (1H; t; J=6.1Hz; C$_8$-H), 4.3~4.7 (2H; m), 4.74 (DOH), 4.9~5.3 (1H; m), 5.36 (2H; s), 5.73 (1H; d; J=1.4Hz), 7.41 (1H; s; side chain C$_1$-H), 8.69 (1H; s; side chain C$_3$-H)

HPLC (retention time): 24 min.

EXAMPLE 4

Synthesis of (5R, 6S, 8R)-2-[(6,7-dihydro-2-(cyclopropylcarbonyl)-5H-pyrrolo[1,2-c] imidazolium-7-yl)thio]-6-(1-hydroxyethyl)-2-penem-3-carboxylate (mixture of isomers A and B)

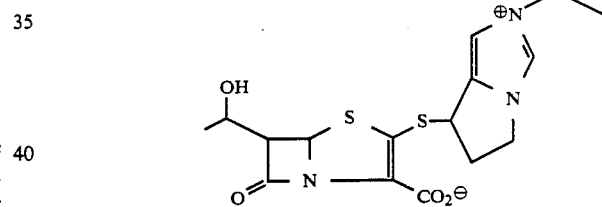

→

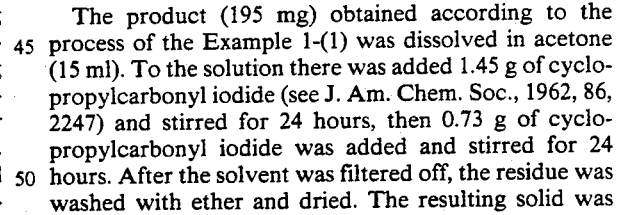

The product (195 mg) obtained according to the process of the Example 1-(1) was dissolved in acetone (15 ml). To the solution there was added 1.45 g of cyclopropylcarbonyl iodide (see J. Am. Chem. Soc., 1962, 86, 2247) and stirred for 24 hours, then 0.73 g of cyclopropylcarbonyl iodide was added and stirred for 24 hours. After the solvent was filtered off, the residue was washed with ether and dried. The resulting solid was dissolved in 25 ml of 50% THF-water and added 3.5 g of ammonium chloride and 1.7 g of iron powder and stirred for 1.5 hours under ice cooling. The solution was concentrated to above 5 ml under reduced pressure after the removal of insolubles by filtration. The concentrate was passed through a column packed with Diaion HP-20 and the fraction eluted with 5% THF-water was further purified by HPLC [carrier: Nucleosil 7C$_{18}$; solvent: 10% acetonitrile; flow rate: 4.75 ml/min.] to obtain 92 mg of the objective compound.

I. R. (KBr disc)cm$^{-1}$: 3360, 3110, 2950, 1765, 1580, 1440, 1350, 1280, 1120

U. V. $\lambda_{max}$ (H$_2$O)nm: 250 (sh), 325

N. M. R. $\delta$(D$_2$O)ppm: 0.3~0.6 (2H; m), 0.6~1.0 (2H; m), 1.218 1.5 (1H; m), 1.33 (3H; d; J=6.3Hz, —CH$_3$), 2.4~3.0 (1H; m), 3.0~3.5 (1H; m); 3.98 (1H; d; J=6.1Hz; C$_6$-H), 4.07 (2H; d; J=7.4Hz), 4.3~4.7 (2H;

m), 4.74 (DOH), 4.9~5.2 (1H; m), 5.73 (1H; brs; C$_5$-H), 7.52 (0.5H; s; side chain C$_1$-H), 7.56 (0.5H; s; side chain C$_1$-H), 8.76 (1H; s; side chain C$_3$-H)

HPLC (retention time): 20 min.

EXAMPLE 5

Synthesis of (5R, 6S, 8R)-6-(1-hydroxyethyl)-2-[(2-cyanomethyl-6,7-dihydro-5H-pyrrolo[1,2-c]imidazolium-7-yl)thio]-2-penem-3-carboxylate (isomers A and B)

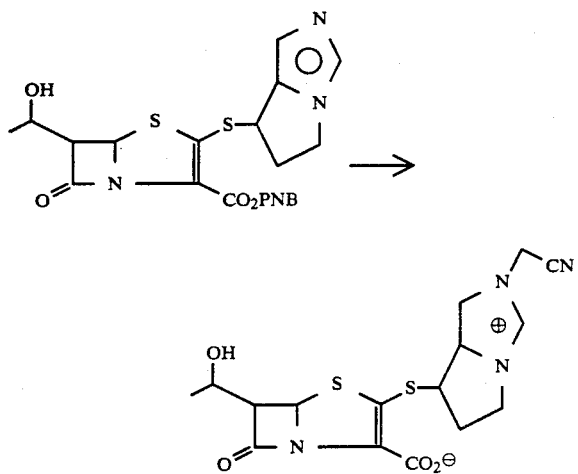

The procedures of the example 3 were repeated except that 20 eq. of bromoacetonitrile instead of bromoacetone was added at 0° to 5° C. and the reaction was continued for 20 hours and thus, the objective compounds mentioned above were obtained after the identical post-treatment in which the HPLC conditions were as follows:

Carrier: Nucleosil 7C$_{18}$ (10×300 mm)
Solvent: 7% acetonitrile-water
Flow rate: 5 ml/min.

Isomer A

Yield 39%
I. R. (KBr disc)cm$^{-1}$: 1765, 1590
N. M. R. δ(D$_2$O)ppm: 2.67~3.05 and 3.13~3.50 (each 1H; each m;

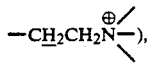

4.07 (1H; dd; J=2, 6Hz; C$_6$-H), 4.10~4.70 (3H; m; C$_8$-H,

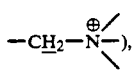

4.80 (HOD), 5.02~5.20 (1H; m;

5.56 (2H; s; —CH$_2$CN), 5.81 (1H; d; J™2Hz; C$_5$-H), 7.75 (1H; s; imidazole ring-H), 9.07 (1H; s; imidazole ring-H)

HPLC (retention time): 9 min.

Isomer B

Yield 43%
I. R. (KBr disc)cm$^{-1}$: 1765, 1595
N. M. R. δ(D$_2$O)ppm: 1.38 (3H; d; J=6Hz; —CH$_3$), 2.54~2.95 and 3.04~3.52 (each 1H; each m;

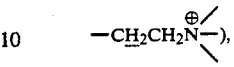

4.04 (1H; dd; J=2, 6Hz; C$_6$-H), 4.20~4.70 (3H; m; C$_8$-H,

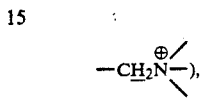

4.80 (HOD), 5.00~5.18 (1H; m;

5.56 (2H; s; —CH$_2$CN), 5.82 (1H; d; J=2Hz; C$_5$-H), 7.79 (1H; s; imidazole ring -H), 9.07 (1H; s; imidazole ring -H)

HPLC (retention time): 11.5 min.

EXAMPLE 6

Synthesis of sodium (5R, 6S, 8R)-6-(1-hydroxyethyl)-2-(2-carboxylatemethyl-6,7-dihydro-5H-pyrrolo[1,2-c]imidazolium-7-yl)thio]-2-penem-3-carboxylate (isomers A and B)

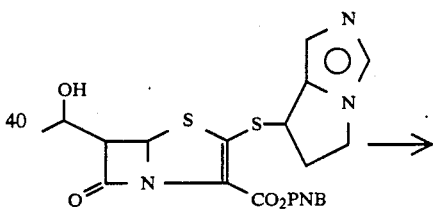

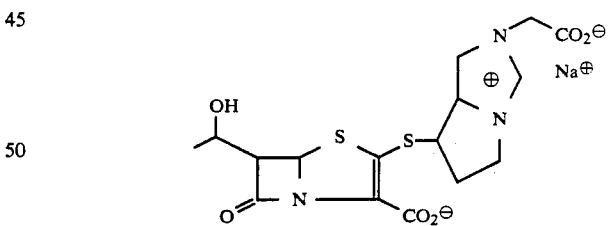

According to the procedures of the example 3, except that 5 eq. of p-nitrobenzyl ester of bromoacetic acid was added at 10° C. instead of bromoacetone and the reaction was continued for three days, the compounds mentioned above were obtained after the identical post-treatment in which the conditions of HPLC were as follows:

Carrier: Nucleosil 7C$_{18}$ (10×300 mm)
Solvent: 5% methanol-water
Flow rate: 5 ml/min.

Isomer A

Yield 19%
U. V. λ$_{max}$ (H$_2$O)nm: 250 (sh), 325

N. M. R. δ(D$_2$O)ppm: 1.37 (3H; d; J=6Hz; CH$_3$), 2.60~3.04 and 3.68~3.58 (each 1H; each m;

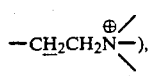

4.05 (1H; dd; J=2,6Hz; C$_6$-H), 4.16~4.64 (3H; m; C$_8$-H;

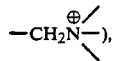

4.80 (HOD), 4.88 (2H; s; —CH$_2$CO$_2$), 5.00~5.20 (1H; m;

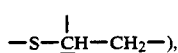

5.80 (1H; d; J=2Hz; C$_5$-H), 7.50 (1H; s; imidazole ring-H), 8.77 (1H; s; imidazole ring-H)
HPLC (retention time): 7.5 min.

Isomer B

Yield 20%
U. V. λ$_{max}$ (H$_2$O)nm: 255 (sh), 325
N. M. R. δ(D$_2$O)ppm: 1.37 (3H; d; J=6Hz; CH$_3$), 2.56~2.94 and 3.05~3.50 (each 1H; each m;

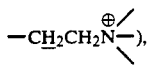

4.03 (1H; dd; J=2, 6Hz; C$_6$-H), 4.16~4.64 (3H; m; C$_8$-H,

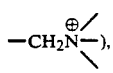

4.80 (HOD), 4.88 (2H, s; —CH$_2$CO$_2$), 4.99~5.18 (1H; m;

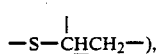

5.80 (1H; d; J=2Hz; C$_5$-H), 7.55 (1H; s; imidazole ring-H), 8.77 (1H; s; imidazole ring-H)
HPLC (retention time): 8.5 min.

EXAMPLE 7

Synthesis of (5R, 6S, 8R)-6-(1-hydroxyethyl)-2-[(2-allyl-6,7-dihydro-5H-pyrrolo[1,2-c]imidazolium-7-yl)thio]-2-penem-3-carboxylate (mixture of isomers A and B)

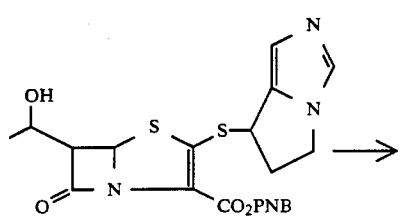

-continued

The procedures of the examples 3 were repeated, except that 20 eq. of allyl bromide was added in place of bromoacetone at 0° to 5° C. and that the reaction was effected for 20 hours and the compound mentioned above was obtained after the identical post-treatment in which HPLC was carried out under the following conditions:
Carrier: Nucleosil 7C$_{18}$ (10×300 mm)
Solvent: 10% acetonitrile-water
Flow rate: 6 ml/min.

Mixture of isomers A and B

Yield 34%
U. V. $_{max}$ (H$_2$O)nm: 253 (sh), 324
N. M. R. δ(D$_2$O)ppm: 1.32 (3H; d; J=6Hz; CH$_3$), 2.50~3.00 and 3.00~3.50 (each 1H; each m;

3.90~4.05 (1H; m; C$_6$-H), 4.10~4.60 (3H; m; C$_8$-H, 4.80 (HOD), 4.80~4.96 (2H; m; —CH$_2$CH=CH$_2$), 4.96~5.14 (1H; m;

5.20~5.60 (2H; m; —CH$_2$CH=CH$_2$), 5.77 (1H; d; J=2Hz; C$_5$-H), 5.84~6.36 (1H; m; —CH$_2$CH=CH$_2$), 7.51 and 7.56 (each 1/2H; each s; imidazole ring-H), 8.79 (1H; s; imidazole ring-H)
HPLC (retention time): 9.7 and 10.2 min.

EXAMPLE 8

Synthesis of (5R, 6S, 8R)-6-(1-hydroxyethyl)-2-[(6,7-dihydro-2-propargyl-5H-pyrrolo[1,2-c]imidazolium-7-yl)thio][-2-penem-3-carboxylate (isomers A and B)

-continued

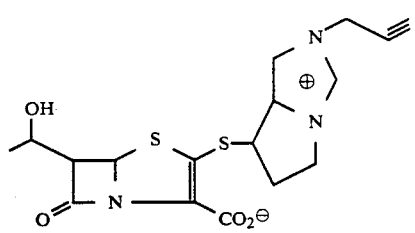

According to the example 3, except for using 20 eq. of propargyl bromide instead of bromoacetone and carrying out the reaction for 17 hours at room temperature, the compounds mentioned above were obtained, after the identical post-treatment in which HPLC was effected under the following conditions:

Carrier: Nucleosil 7$C_{18}$ (10×300 mm)
Solvent: 10% acetonitrile-water
Flow rate: 6 ml/min.

Isomer A

Yield 20%
U. V. $\lambda_{max}$ ($H_2O$)nm: 250 (sh), 324
N. M. R. δ($D_2O$)ppm: 1.38 (3H; d; J=6Hz; $CH_3$), 2.68~3.05 and 3.10~3.58 (each 3H; each m;

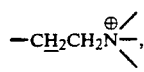

—C≡CH), 4.06 (1H; dd; J=2, 6Hz; $C_6$-H), 4.16~4.65 (3H; m; $C_8$-H, —$CH_2$C≡CH), 5.80 (1H; d; J=2Hz; $C_5$-H), 7.68 (1H; s; imidazole ring-H), 8.96 (1H; s; imidazole ring-H)
HPLC (retention time): 7.6 min.

Isomer B

Yield 23%
U. V. $\lambda_{max}$ ($H_2O$)nm: 257, 324
N. M. R. δ($D_2O$)ppm: 1.38 (3H; d; J=6Hz: $C_6$-H), 2.57~3.00 and 3.00~3.53 (each 3H; each m;

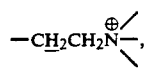

—C≡CH), 4.04 (1H; dd; J=2, 6Hz; $C_6$-H), 4.20~4.70 (3H; m; $C_8$-H,

4.80 (HOD), 5.00~5.25 (3H; m;

—$CH_2$C≡CH), 5.82 (1H; d; J=2Hz; $C_5$-H), 7.71 (1H; s; imidazole ring-H), 8.97 (1H; s; imidazole ring-H)
HPLC (retention time): 8.6 min.

EXAMPLE 9

Synthesis of (5R, 6S, 8R)-2-[(6,7-dihydro-2-(methoxycarbonylmethyl)-5H-pyrrolo[1,2-c]imidazolium-7-yl)thio]-6-(1-hydroxyethyl)-2-penem-3-carboxylate (isomers A and B)

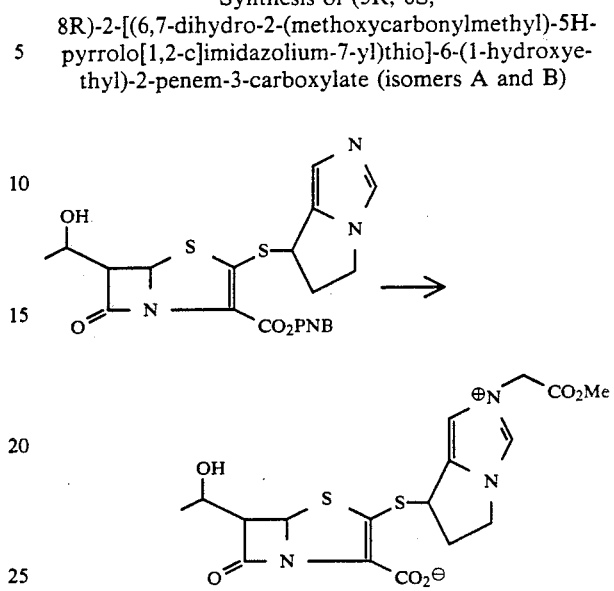

The product (150 mg) obtained according to the example 1-(1) was dissolved in acetone (12 ml), added 0.57 ml of methyl bromacetate and stirred for 96 hours. After evaporating the solvent, the resulting residue was washed with ether and dried. The solid obtained was dissolved in THF-water (23 ml), added 3.1 g of ammonium chloride and 1.6 g of iron powder and stirred for 2 hours while ice cooling. Insolubles were removed by filtration before concentrating the filtrate to about 5 ml in volume. The concentrate was first passed through a column packed with Diaion HP-20 and then the fraction eluted with 5% THF-water was purified by HPLC to obtain the objective compound. The conditions of HPLC were as follows:

Carrier: Nucleosil 7$C_{18}$ (10×300 mm)
Solvent 10% acetonitrile-water
Flow rate: 3.65 ml/min Isomer A Yield 7 mg
I. R. (KBr disc)$cm^{-1}$: 3400, 1760, 1590, 1360
U. V. $\lambda_{max}$ ($H_2O$)nm: 248 (sh), 322
N. M. R. δ($D_2O$)ppm: 1.43 (3H; d; J=6Hz; —$CH_3$), 2.5~3.0 (1H; m), 3.0~3.6 (1H: m). 3.86 (3H; s; —$COOCH_3$), 3.95 (1H; d; J=6Hz; $C_6$-H), 4.29 (1H; t; J=6Hz; $C_8$-H), 4.3~4.7 (2H; m), 4.74 (DOH), 4.9~5.2 (1H; m), 5.20 (2H; s), 5.83 (1H; brs, $C_5$-H), 7.56 (1H; s; side chain $C_1$-H), 8.81 (1H; s; side chain $C_3$-H)
HPLC (retention time): 9 min.

Isomer B

Yield 14 mg
I. R. (KBr disc)$cm^{-1}$: 3400, 1760, 1590, 1370
U. V. $\lambda_{max}$ ($H_2O$)nm: 259 (sh), 325
N. M. R. δ($D_2O$)ppm: 1.33 (3H; d; J=6.3Hz; —$CH_3$), 2.4~3.0 (1H; m), 3.0~3.5 (1H; m), 3.86 (3H; s; —$COOCH_3$), 3.96 (1H; d; J=6.3Hz; $C_6$-H), 4.29 (1H; t; J=6.3Hz; $C_8$-H), 4.4~4.7 (2H; m), 4.74 (DOH), 4.9~5.2 (1H; m), 5.20 (2H; s), 5.73 (1H; brs; $C_5$-H), 7.55 (1H; s; side chain $C_1$-H), 8.81 (1H; s; side chain $C_3$-H)
HPLC (retention time): 16 min.

EXAMPLE 10

Synthesis of (5R, 6S, 8R)-2-[(6,7-dihydro-2-(carbamoylmethyl)-5H-pyrrolo[1,2-c]imidazolium-7-yl)thio]-6-(1-hydroxyethyl)-2-penem-3-carboxylate (isomers A and B)

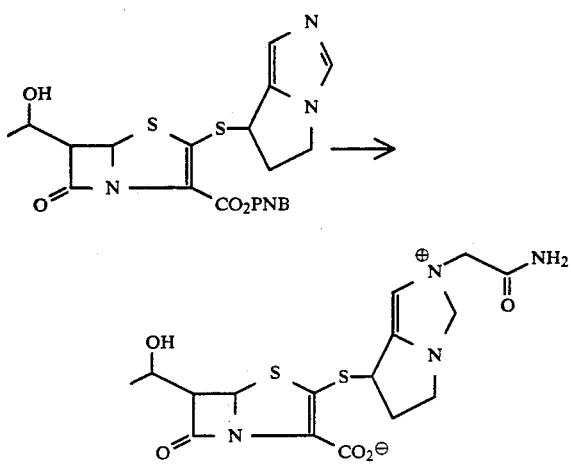

The penem derivative (196 mg) prepared according to the process disclosed in the example 1-(1) was dissolved in acetone (15 ml), added iodo acetamide (1.48 g) and stirred for 23 hours. The solvent was removed in vacuo and the resultant residue was washed with ether and dried. The solid obtained was dissolved in 50% THF-water (25 ml), added ammonium chloride (3.6 g) and iron powder (1.8 g) and stirred for 1.5 hours under ice cooling. After removing insolubles from the reaction solution by filtration, the resultant filtrate was condensed up to about 5 ml which was passed through a column packed with Diaion HP-20. The combined fractions eluted with 5% THF-water were further purified by HPLC which was effected under the following conditions:
Carrier: Nucleosil 7C$_{18}$ (10×300 mm)
Solvent: 7% acetonitrile-water
Flow rate: 3.65 ml/min.
Thus, the objective isomers were prepared.

Isomer A

Yield 45 mg
I. R. (KBr disc)cm$^{-1}$: 3380, 1760, 1680, 1580, 1360, 1290, 1120
U. V. $\lambda_{max}$ (H$_2$O)nm: 248 (sh), 326
N. M. R. $\delta$(D$_2$O)ppm: 1.31 (3H; d; J=6.4Hz; —CH$_3$), 2.5~3.0 (1H; m), 3.0~3.6 (1H; m), 3.99 (1H; dd; J=1.3Hz, 5.9Hz; C$_6$-H), 4.1~4.6 (2H; m), 4.26 (1H; t; J-5.9Hz; C$_8$-H), 4 74 (DOH), 4.9~5.2 (1H; m), 5.08 (2H; s), 5.72 (1H; d; J=1.3Hz; C$_5$-H), 7.46 (1H; s; side chain C$_1$-H), 8.77 (1H;s; side chain C$_3$-H)
HPLC (retention time): 11 min.

Isomer B

Yield 57 mg
I. R. (KBr disc)cm$^{-1}$: 3380, 1765, 1695, 1590, 1370, 1295, 1130
U. V. $\lambda_{max}$ (H$_2$O)nm: 256 (sh), 324
N. M. R. $\delta$(D$_2$O)ppm: 1.30 (3H; d; J=6.4Hz; —CH$_3$), 2.4~2.9 (1H; m), 2.9~3.5 (1H; m), 3.95 (1H; dd; J=1.5Hz, 5.9Hz; C$_6$-H), 4.1~4.6 (2H; m), 4.26 (1H; t; J=5.9Hz; C$_8$-H), 4.74 (DOH), 4.9~5.2 (1H; m), 5.09 (2H; s), 5.71 (1H; d; J=1.5Hz; C$_5$-H), 7.50 (1H; s; side chain C$_1$-H), 8.78 (1H; s; side chain C$_3$-H)
HPLC (retention time): 16 min.

EXAMPLE 11

Synthesis of (5R, 6S, 8R)-2-[(6,7-dihydro-2-benzyl-5H-pyrrolo[1,2-c]imidazolium-7-yl)thio]-6-(1-hydroxyethyl)-2-penem-3-carboxylate (mixture of isomers A and B)

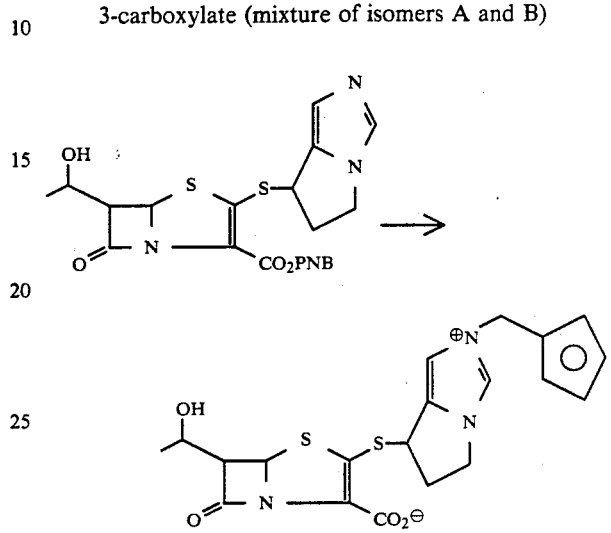

According to the procedures of the Example 3, except that 20 eq. of benzyl bromide was used instead of bromoacetone and that the reaction was continued for 18 hours and thus the objective compound (yield: 60%) was obtained after the post-treatment in which HPLC was effected under the following conditions:
Carrier: Nucleosil 7C$_{18}$ (10×300 mm)
Solvent: 15% acetonitrile-water
Flow rate: 5.9 ml/min.
I. R. (KBr disc)cm$^{-1}$: 3420, 1770, 1590, 1450, 1360,
U. V. $\lambda_{max}$ (H$_2$O)nm: 253 (sh), 325
N. M. R. $\delta$(D$_2$O)ppm: 1.31 (3H;, d; J=6Hz; CH$_3$), 2.5~3.0 (1H; m), 3.0~3.5 (1H; m), 3.7 and 3.89 (each 0.5H; each d; J=5.9Hz; C$_6$-H), 4.1~4.6 (3H; m; C$_8$-H, side chain C$_5$-H), 4.74 (DOH), 4.9~5.1 (1H; m), 5.41 (2H; s), 5.49 and 5.60 (each 0.5H; each brs; C$_5$-H), 7.48 (6H; brs; side chain C$_1$-H, Ar-H), 8.78 and 8.82 (each 0.5H; each s; side chain C$_3$-H)
HPLC (retention time): 16 min. (isomer A) 17 min. (isomer B)

EXAMPLE 12a

Synthesis of (5R, 6S, 8R)-2-[(6,7-dihydro-2-ethyl-5H-pyrrolo[1,2-c]imidazolium-7-yl)thio]-6-(1-hydroxyethyl)-2-penem-3-carboxylate (isomers A and B)

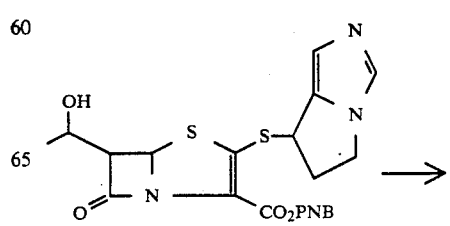

-continued

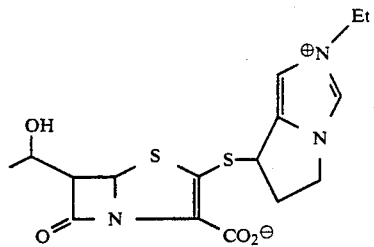

p-Nitrobenzyl (5R, 6S, 8R)-2-[(6,7-dihydro-5H-pyrrolo [1,2-c]imidazol-7-yl)thio]-6-(1-hydroxyethyl)-2-penem-3-carboxylate (161 mg) was dissolved in acetone (15 ml) and thereafter 0.53 ml of ethyl iodide was added three times every 24 hours, then stirred for 48 hours The solvent was distilled off before the resultant residue was washed with ether and dried. The solid obtained was dissolved in 25 ml of 50% THF-water, added 3.2 g of ammonium chloride and 1.6 g of iron powder and stirred for 70 minutes under ice cooling. Insolubles were filtered off before evaporating the filtrate to about 5 ml under reduced pressure. The concentrate was passed through a column Diaion HP-20 and the fractions eluted with 5% THF-water were further purified by HPLC effected under the following conditions:

Carrier: Nucleosil 7C$_{18}$ (10×300 mm)

Solvent: 10% acetonitrile-water

Flow rate: 3.65 ml/min.

and thus the objective compounds (isomers A and B) were obtained:

Isomer A

Yield 32 mg

I. R. (KBr disc)cm$^{-1}$: 3400, 1765, 1580, 1445, 1360, 1280, 1120

U. V. $\lambda_{max}$ (H$_2$O )nm: 248 (sh), 324

N. M. R. $\delta$(D$_2$O)ppm: 1.34 (3H; d; J=6.1Hz; CH$_3$), 1.52 (3H; t; J=7.2Hz), 2.6~3.0 (1H; m), 3.0~3.5 (1H; m), 4.00 (1H; d; J=5.9Hz; C$_6$-H), 4.1~4.7 (3H; m), 4.26 (2H; q; J=7.2Hz), 4.74 (DOH), 4.9~5.1 (1H; s; side chain, C$_5$-H), 5.75 (1H; s; C$_5$-H), 7.50 (1H; s; side chain C$_1$-H), 8.71 (1H; s; side chain C$_3$-H)

HPLC (retention time): 13 min.

Isomer B

Yield 44mg

I. R. (KBr disc)cm$^{-1}$: 3420, 1765, 1590, 1440, 1360, 1285, 1120

U. V. $\lambda_{max}$ (H$_2$O)nm: 258 (sh), 324

N. M. R. $\delta$(D$_2$O)ppm: 1.33 (3H; d; J=6.4Hz; CH$_3$), 1.52 (3H; t; J=7.2Hz), 2.5~2.9 (1H; m), 2.9~3.5 (1H; m), 3.97 (1H; d; J=5.9Hz; C$_6$-H), 4.1~4.7 (3H; m), 4.26 (2H; q; J=7.2Hz), 4.74 (DOH), 4.9~5.1 (1H; m), 5.77 (1H; s; C$_5$-H), 7.54 (1H; s; side chain C$_1$-H), 8.71 (1H; s; side chain C$_3$-H)

HPLC (retention time): 15 min.

EXAMPLE 12b

Synthesis of (5R, 6S, 8R)-2-[(6,7-dihydro-2-(3-methoxycarbonyl-2-oxopropyl)-5H-pyrrolo[1,2-c]imidazolium-7-yl)thio]-6-(1-hydroxyethyl)-2-penem-3-carboxylate (isomers A and B)

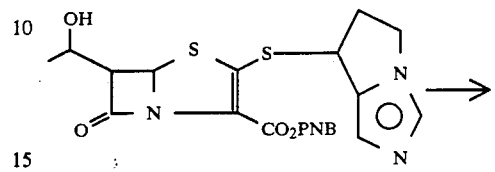

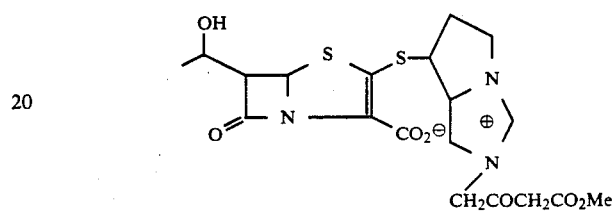

According to the procedures of the example 3, except that 10 eqs. of methyl bromoacetoacetate was used instead of bromoacetone and the reaction was effected at room temperature for 5 hours, the objective compound was obtained after post-treatment carried out according to the example 1-(2), in which HPLC was effected under the following conditions:

Carrier: Nucleosil 7C$_{18}$ (10×300 mm)

Solvent: 10% acetonitrile-water

Flow rate: 6 ml/ min.

Isomer A

Yield 10%

U. V. $\lambda_{max}$ (H$_2$O)nm: 250 (sh), 325

N. M. R. $\delta$(D$_2$O)ppm: 1.37 (3H; d; J=6Hz; CH$_3$), 2.60~3.10 and 3.10~3.65 (each 2H; each m;

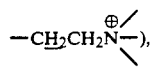

3.83 and 3.86 (each 3H; each s; CO$_2$CH$_3$), 3.96~4.10 (1H; m; C$_6$-H), 4.17~4.70 (3H; m), 4.80 (HOD), 5.80 (1H; brs; C$_5$-H), 7.44 and 7.56 (each 1H; each s; imidazole ring-H), 8.76 and 8.82 (each 1H; each s; imidazole ring-H)

HPLC (retention time): 14.5 min.

Isomer B

Yield 12%

U. V. $\lambda_{max}$ (H$_2$O)nm: 255 (sh), 324

N. M. R. $\delta$(D$_2$O)ppm: 1.39 (3H; d; J=6Hz; CH$_3$), 2.60~3.00 and 3.10~3.60 (1H; each m;

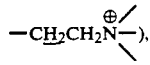

3.85 and 3.88 (each 3H; each s; CO$_2$CH$_3$), 3.95~4.10 (1H; m; C$_6$-H), 4.24~4.75 (3H; m), 4.80 (HOD), 5.76~5.84 (1H; m; C$_5$-H), 7.48 and 7.64 (each 1H; each s; imidazole ring-H), 8.80 and 8.84 (each 1H; each s; imidazole ring-H)

HPLC (retention time): 18.8 min.

EXAMPLE 12c

Synthesis of (5R, 6S, 8R)-2-[(6,7-dihydro-2-(4-fluorobenzyl)-5H-pyrrolo[1,2-c]imidazolium-7-yl)-thio]-6-(1-hydroxyethyl)-2-penem-3-carboxylate (a mixture of isomers A and B)

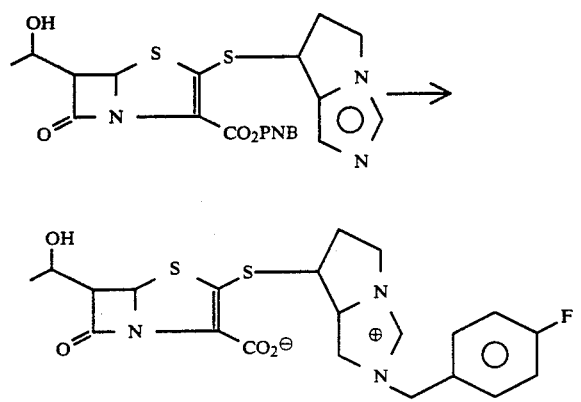

According to the procedures of the example 3, except that 10 eqs. of 4-fluorobenzylbromide was instead of bromoacetone and that the reaction was effected at room temperature for 17 hours, the objective compound was obtained after the post-treatment carried out according to the example 1-(2), in which HPLC was effected under the following conditions:

Carrier: Nucleosil 7C$_{18}$ (10×300 mm)
Solvent: 20% acetonitrile-water
Flow rate: 6 ml/min.

Mixture of Isomers A and B

Yield 43%

U. V. $\lambda_{max}$ (H$_2$O)nm: 255 (sh), 324

N. M. R. δ(D$_2$O)ppm: 1.36 (3H; d; J=6Hz; CH$_3$), 2.52~2.97 and 3.08~3.52 (each 2H; each m;

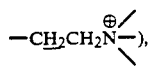

3.82 and 3.96 (each 1H; each dd; J=2, 6Hz; C$_6$-H), 4.20~4.75 (3H; m), 4.80 (HOD), 4.92~5.12 (1H; m), 5.44 (2H; s; —CH$_2$Ar) 5.55 and 5.65 (each 1H; each s; C$_5$-H), 7.12~7.64 (5H; m; 4×ArH, imidazole ring-H), 8.82 and 8.85 (each 1H; each s; imidazole ring-H)

HPLC (fetention time): 14.5 min. and 15 min.

EXAMPLE 13

Synthesis of (5R, 6S, 8R)-2-[(6,7-dihydro-methyl-5H-pyrrolo[1,2-c]-1,2,4-triazolium-7-yl)thio]-6-(1-hydroxyethyl)-2-penem-3-carboxylate (isomers A and B and a mixture of isomers C and D)

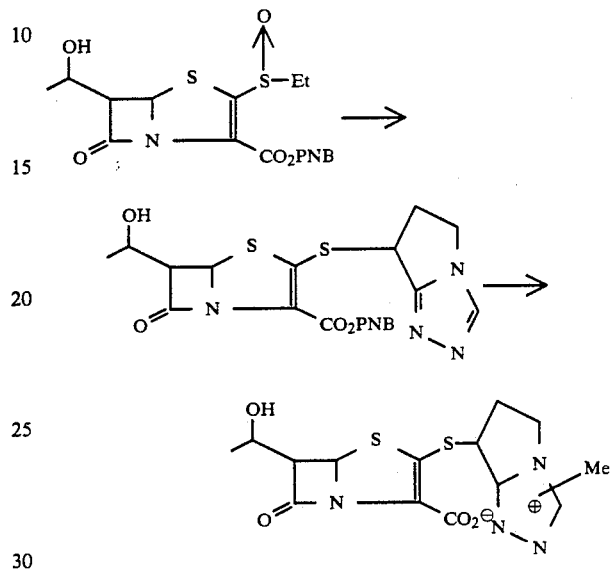

(1) Synthesis of p-nitrobenzyl ester of (5R, 6S, 8R)-2-[(6,7-dihydro-5H-pyrrolo[2,1-c]-1,2,4-triazol-7-yl)thio]-6-(1-hydroxyethyl)-2-penem-3-carboxylic acid Thiol derivative (361 mg) obtained by the process hereunder explained in the reference example 1 was treated according to the procedures of the example 1-(1) to form the objective compound (yield: 207 mg) mentioned above.

N. M. R. δ(CDCl$_3$)ppm: 1.40 (3H; d; J=6Hz; CH$_3$), 2.5~3.0 (1H; m; pyrrole ring C$_6$-H), 3.0~3.6 (1H; m; pyrrole ring C$_6$-H), 3.6~4.5 (4H; m; pyrrole ring C$_5$-H$_2$, C$_6$-H and C$_8$-H), 4.85 (1H; dd; J=8, 4Hz; pyrrole ring C$_7$-H), 5.25 and 5.39 (1H; ABq; J=14Hz; CO$_2$H$_2$Ar), 5.31 and 5.43 (1H; ABq; J=14Hz; C$_{02}$CH$_2$Ar), 7.63 and 7.65 (each 1H; each d; J=9Hz; ArH), 8.20 (1H; s; triazole ring C$_3$-H), 8.22 and 8.24 (each 1H; each d; J=9Hz; ArH)

(2) Synthesis of (5R, 6S, 8R)-2-[(6,7-dihydro-methyl-5H-pyrrolo[2,1c]-1,2,4-triazolium-7-yl)thio]-6-(1-hydroxyethyl)-2-penem-3-carboxylate (isomers A and B, a mixture of isomers C and D)

The compound (340 mg) obtained in the above step (1) was treated according to the procedures similar to those described in the example 2 to obtain the objective compounds mentioned above. The purification was effected according to HPLC which was carried out under the following conditions:

Carrier Nucleosil 7C$_{18}$ (10×300 mm)
Solvent: 5% acetonitrile-water
Flow rate: 3.65 ml/min.

Isomer A

Yield 8 mg
I. R. (KBr disc)cm$^{-1}$: 1775, 1600

U. V. λ_max (H2O)nm: 257, 327

N. M. R. δ(D2O)ppm: 1.33 (3H; d; J=6Hz; CH3), 2.9~3.3 (1H; m; pyrrole ring C6-H), 3.3~3.9 (1H; m; pyrrole ring C6-H), 4.04 (1H; dd; J=6, 2Hz; C6-H), 4.16 (3H; s; NCH3), 4.1~4.7 (3H; m; pyrrole ring C5-H2 and C8-H), 5.18 (1H; dd; J=10, 5Hz; pyrrole ring C7-H), 5.76 (1H; d; J=2Hz; C5-H), 8.80 (1H; s; triazole ring C3-H)

HPLC (retention time): 12.1 min.

Isomer B

Yield 20 mg

I. R. (KBr disc)cm$^{-1}$: 1775, 1600

U. V. λ_max (H2O)nm: 261, 328

N. M. R. δ(D2O)ppm: 1 33 (3H; d; J=6Hz; CH3), 2.9~3.3 (1H; m; pyrrole ring C6-H), 3.3~3.9 (1H; m; pyrrole ring C6-H), 4.04 (1H; dd; J TM 6, 2Hz; C6-H), 4.18 (3H; s; NCH3), 4.1~4.7 (3H; m; pyrrole ring C5-H2 and C8-H), 5.18 (1H; dd; J=10, 5Hz; pyrrole ring C7-H), 5.76 (1H; d; J=2Hz; C5-H), 8.80 (1H; s; triazole ring C3-H)

HPLC (retention time): 13.5 min.

Mixture of Isomers C and D

Yield 91 mg

I. R. (KBr disc)cm$^{-1}$: 1775, 1600

U. V. λ_max (H2O)nm: 253, 326

N. M. R. δ(D2O)ppm: 1.36 (3H; d; J=6Hz; CH3), 2.6~3.1 (1H; m; pyrrole ring C6-H), 3.1~3.7 (1H; m; pyrrole ring C6-H), 4.07 (1.5H; s; NCH3), 4.08 (1.5H; s; NCH3), 4.0~4.8 (4H; m; pyrrole ring C5-H2, C6-H and C8-H), 5.12 (1H; dd; J=10, 5Hz; pyrrole ring C7-H), 5.80 (1H; d; J=2Hz; C5-H)

HPLC (retention time): 16.2 and 16.6 min.

EXAMPLE 14

Synthesis of sodium (5R, 6S, 8R)-2-[(6,7-dihydro-3-trifluoromethyl-5H-pyrrolo[2,1-c]-1,2,4-triazol-6-yl)thio]-6-(1-hydroxyethyl)-2-penem-3-carboxylate (isomers A and B)

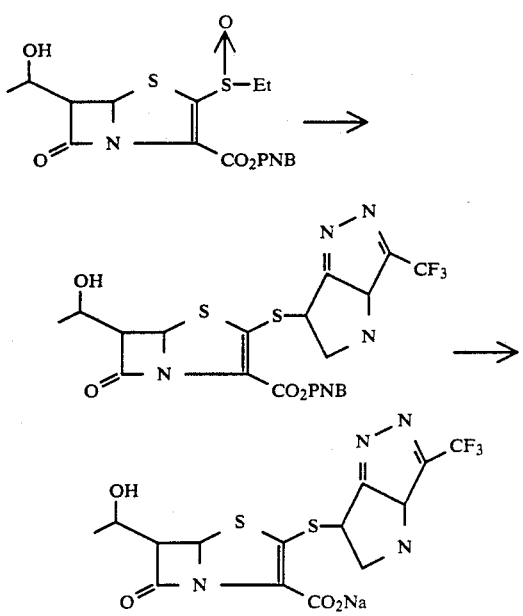

(1) Synthesis of p-nitrobenzyl ester of (5R, 6S, 8R)-2-(6,7-dihydro-3-trifluoromethyl-5H-pyrrolo[2,1-c]-1,2,4-triazol-6-yl)thio)-6-(1-hydroxyethyl)-2-penem-3-carboxylic acid A thiol derivative (231 mg) prepared according to the procedures of the reference example 2 hereunder explained in more detail was treated in accordance with the procedures disclosed in the example 1-(1) to form the objective compound described above.

N. M. R. δ(CDCl3)ppm: 1.40 (3H; d; J=6Hz; CH3), 3.0~3.4 (1H; m; pyrrole ring C7-H), 3.4~3.7 (1H; m; pyrrole ring C7-H), 3.84 (1H; m; C6-H), 4.1~4.5 (2H; m; pyrrole ring C6-H and C8-H), 4.5~4.9 (2H; m; pyrrole ring C5-H2), 5.20 and 5.48 (each 2H; each ABq; J=14Hz; CO2CHAr), 7.60 (2H; d; J=9Hz; ArH), 8.24 (2H; d; J=9Hz; ArH)

(2) Synthesis of sodium (5R, 6S, 8R)-2-[(6,7-dihydro-3-trifluoromethyl-5H-pyrrolo[2,1-c]-1,2,4-triazol-6-yl)thio]-6-(1-hydroxyethyl)-2-penem-3-carboxylate (isomers A and B)

The product (59 mg) obtained in the above step (1) was ed and the procedures similar to those disclosed in the example 1-(2) were repeated to obtain the compounds mentioned above. The products were purified by HPLC under the following conditions:

Carrier: Nucleosil 7C18 (10×300 mm)
Solvent: 5% acetonitrile-water
Flow rate: 3.65 ml/min.

Isomer A

Yield 13 mg

I. R. (KBr disc)cm$^{-1}$: 1770, 1595

U. V. λ_max (H2O)nm: 256, 323

N. M. R. δ(D2O)ppm: 1.36 (3H; d; J=6Hz; CH3), 3.09 (1H; dd; J=18, 5Hz; pyrrole ring C7-H), 3.68 (1H; dd; J=18, 7Hz; pyrrole ring C7-H), 3.99 (1H; dd; J=7, 2Hz; C6-H), 4.2~4.7 (4H; m; pyrrole ring C5-H2, pyrrole ring C6-H and C8-H), 5.76 (1H; d; J=2Hz; C5-H)

HPLC (retention time): 15.4 min.

Isomer B

Yield 13 mg

I. R. (KBr disc)cm$^{-1}$: 1760, 1590

U. V. λ_max (H2O)nm: 252, 324

N. M. R. δ(D2O)ppm: 1.40 (3H; d; J=6Hz; CH3), 3.28 (1H; dd; J=18, 5Hz; pyrrole ring C7-H), 3.78 (1H; dd; J=18, 7Hz; pyrrole ring C7-H), 4.00 (1H; dd; J=7, 2Hz; C6-H), 4.2~4.7 (4H; m; pyrrole ring C5-H2, pyrrole ring C6-H and C8-H), 5.76 (1H; d; J=2Hz; C5-H)

HPLC (retention time): 18.6 min.

According to the procedures similar to those disclosed above, the following compounds were prepared:

(a) Mixture of Isomers A and B of (5R, 6S, 8R)-2-[(3-amino-6,7-dihydro-5H-pyrrolo[2,1-c]-1,2,4-triazol-7-yl)-thio]-6-(1-hydroxyethyl)-2-penem-3-carboxylic acid

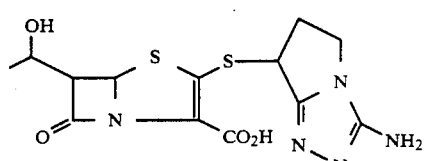

HPLC (retention time): 8 min.
Conditions of HPLC
Carrier: Nucleosil 7C$_{18}$ (10×300 mm)
Solvent: 5% methanol-water
Flow rate: 4 ml/min.
I. R. (KBr disc)cm$^{-1}$: 1776
N. M. R. δ(D$_2$O)ppm: 1.40 (3H; d; J=6Hz; CH$_3$), 2.60~3.20 and 3.20~3.65 (each 1H; each m; —CH$_2$CH$_2$N), 3.95~4.50 (4H; m; C$_6$-H, C$_8$-H, —CH$_2$N), 4.80 (HOD), 5.80 (1H; d; J=2Hz; C$_5$-H)

(b) Mixture of isomers A and B of (5R, 6S, 8R)-2-[(3-chloro-6,7-dihydro-5H-pyrrolo[2,1-c]-1,2,4-triazol-7-yl)thio]-6-(1-hydroxyethyl)-2-penem-3-carboxylic acid

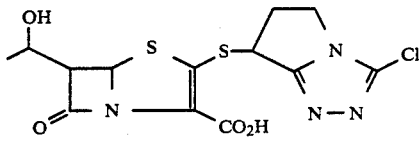

HPLC (retention time): 17 min.
Conditions
Carrier: Nucleosil 7C$_{18}$ (10×300 mm)
Solvent: 5% acetonitrile-water
Flow rate: 4 ml/min.
I. R. (KBr disc)cm$^{-1}$: 1770
N. M. R. δ(D$_2$O)ppm: 1.38 (3H; d; J=6Hz; CH$_3$), 2.60~3.80 (2H; m; —CH$_2$CH$_2$N), 3.85~4.40 (4H; m; C$_6$-H, C$_8$-H, —CH$_2$N), 4.80 (HOD), 5.78 (1H; d; J=2Hz; C$_5$-H)

(c) Isomers A and B of (5R, 6S, 8R)-2-[(2-amino-6,7-dihydro-5H-pyrrolo[2,1-b]-1,2,4-triazol-7-yl)thio]-6-(1-hydroxyethyl)-2-penem-3-carboxylic acid

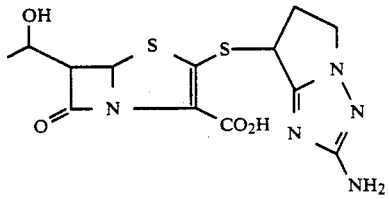

Isomer A

I. R. (KBr disc)cm$^{-1}$: 1767
N. M. R. δ(D$_2$O)ppm: 1.35 (3H; d; J=6Hz; CH$_3$), 2.55~3.60 (2H; m; CH$_2$CH$_2$N), 3.85~4.50 (4H; m; C$_5$-H, C$_8$-H, CH$_2$N), 4.80 (HOD), 5.75 (1H; d; J=2Hz; C$_5$-H)
HPLC (retention time): 12 min.
Conditions
Nucleosil 7C$_{18}$ (10×300 mm)
3% acetonitrile-water
4 ml/min.

Isomer B

I. R. (KBr disc)cm$^{-1}$: 1770
N. M. R. δ(D$_2$O)ppm: 1.36 (3H; d; J=6Hz; CH$_3$) 2.60~3.60 (2H; m; CH$_2$CH$_2$N), 3.85~4.40 (4H; m; C$_6$-H, C$_8$-H, —CH$_2$N), 4.80 (HOD), 5.90 (1H; d; J=2Hz; C$_5$-H)
HPLC (retention time): 13 min.

(d) Isomers A and B of (5R, 6S, 8R)-2-[(2-chloro-6,7-dihydro-5H-pyrrolo[2,1-b]-1,2,4-triazol-7-yl)thio]-6-(1-hydroxyethyl)-2-penem-3-carboxylic acid

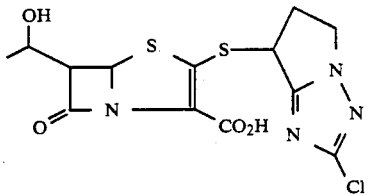

Isomer A

I R. (KBr disc)cm$^{-1}$: 1770
N. M. R. δ(D$_2$O)ppm: 1.40 (3H; d; J=6Hz; CH$_3$), 2.60~3.00 and 3.20~3.62 (each 1H; each m; CH$_2$CH$_2$N), 4.80 (HOD), 5.78 (1H; d; J=2Hz; C$_5$-H)
HPLC (retention time): 14 min.
Conditions:
Nucleosil 7C$_{18}$ (10×300 mm)
5% acetonitrile-water
4 ml/min.

Isomer B

I. R. (KBr disc)cm$^{-1}$: 1770
N. M. R. δ(D$_2$O)ppm: 1.35 (3H; d; J=6Hz; CH$_3$), 2.65~3.05 and 3.18~3.60 (each 1H; each m; CH$_2$CH$_2$N), 3.85~4.55 (4H; m; C$_5$-H, C$_8$-H, —CH$_2$N), 4.80 (HOD), 5.78 (1H; d; J=2Hz; C$_5$-H)
HPLC (retention time): 16 min.

(e) Isomers A and B of (5R, 6S, 8R)-2-[(6,7-dihydro-5H-pyrrolo[1,2-c]thiazolium-6-yl)thio]-6-(1-hydroxyethyl)-2-penem-3-carboxylate

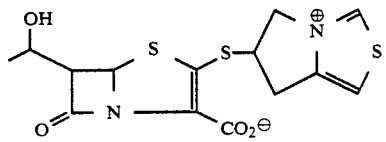

Isomer A

I. R. (KBr disc)cm$^{-1}$: 3430, 1765, 1590, 1370, 1280, 1260
U. V. λ$_{max}$ (H$_2$O)nm: 249, 323 N. M. R. δ(D$_2$O)ppm: 1.31 (3H; d; J=6.2Hz; CH$_3$), 3.0~3.8 (2H; m), 3.97 (1H; dd; J=1.1Hz, 6.4Hz; C$_6$-H), 4.27 (1H; t; J=6.4Hz; C$_8$-H), 4.2~5.2 (3H; m), 4.74 (DOH), 5.75 (1H; d; J=1.1Hz; C$_5$-H), 7.85 (1H; s; side chain C$_1$-H), 9.84 (1H; s; side chain C$_3$-H)
HPLC (retention time): 14 min.
Condition
Nucleosil 7C$_{18}$ (10×300 mm)
5% acetonitrile-water
3.65 ml/min.

Isomer B

I. R. (KBr disc)cm$^{-1}$: 3420, 1770, 1580, 1370, 1280, 1260
U. V. λ$_{max}$ (H$_2$O)nm: 249, 323
N. M. R. δ(D$_2$O)ppm: 1.31 (3H; d; J=6.2Hz; CH$_3$), 3.0~3.8 (2H; m), 4.01 (1H; dd; J™1.1Hz; 6.4Hz;

C6-H), 4.27 (1H; t; J=6.4Hz; C8-H), 4.2~5.2 (3H; m), 4.74 (DOH), 5.77 (1H; d; J=1.1Hz; C5-H), 7.86 (1H; s; side chain C1-H), 9.84 (1H; s; side chain C3-H)

HPLC (retention time): 17 min.

(f) Mixture of isomers A and B of (5R, 6S, 8R)-2-[(5,6-dihydro-4H-pyrrolo[1,2-c]-1,2,3-triazol-4-yl)-thio]-6-(1-hydroxyethyl)-2-penem-3-carboxylic acid

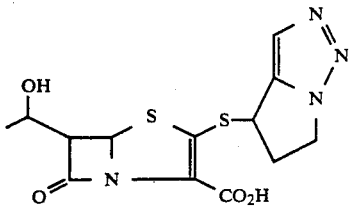

I. R. (KBr disc)cm$^{-1}$: 3400, 1765, 1585, 1380
U. V. $\lambda_{max}$ (H$_2$O)nm: 253, 324
N. M. R. $\delta$(D$_2$O)ppm: 1.34 (3H; d; J=6Hz; CH$_3$), 2.6~3.2 (1H; m), 3.2~3.7 (1H; m), 3.8~4.1 (1H; m; C6-H), 4.27 (1H; t; J=6Hz; C8-H), 4.3~5.2 (3H; m), 4.74 (DOH), 5.72 (1H; brs, C5-H), 7.75 (0.5H; s; side chain C3-H), 7.79 (0.5H; s; side chain C3-H)

HPLC (retention time): 16.5 min.
Conditions
Nucleosil 7C$_{18}$ (10×300 mm)
3% acetonitrile-water
3.65 ml/min.

(g) Isomers A and B of (5R, 6S, 8R)-2-[(5,6-dihydro-2-methyl-4H-pyrrolo[1,2-c]-1,2,3-triazolium-4-yl)-thio]-6-(1-hydroxyethyl)-2-penem-3-carboxylate

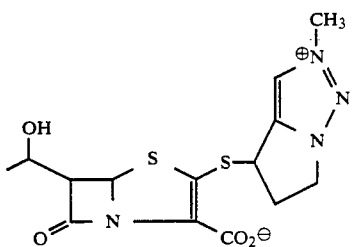

Isomer A

I. R. (KBr disc)cm$^{-1}$: 1765
U. V. $\lambda_{max}$ (H$_2$O)nm: 325
N. M. R. $\delta$(D$_2$O)ppm: 1.34 (3H; d; J=5.9Hz; CH$_3$), 2.6~3.2 (1H; m), 3.2~3.8 (1H; m), 3.9~4.1 (1H; m; C6-H), 4.1~4.9 (3H; m), 4.35 (3H; s; CH$_3$), 4.74 (DOH), 4.9~5.3 (1H; m), 5.77 (1H; d; J=1.2Hz; C5-H), 8.51 (1H; s; side chain C3-H)

HPLC (retention time): 14 min.
Condition
Nucleosil 7C$_{18}$ (10×300 mm)
5% acetonitrile-water
3 65 ml/min.

Isomer B

I. R. (KBr disc)cm$^{-1}$: 1765
U. V. $\lambda_{max}$ (H$_2$O)nm: 326
N. M. R. $\delta$(D$_2$O)ppm: 1.34 (3H; d; J=6.3Hz; CH$_3$), 2.6~3.1 (1H; m), 3.2~3.8 (1H; m), 3.9~4.1 (1H; m; C6-H), 4.1~5.0 (3H; m), 4.36 (3H; s; CH$_3$), 4.74 (DOH), 5.0~5.3 (1H; m), 5.81 (1H; d; J=1.2Hz; C5-H), 8.58 (1H; s; side chain C3-H)

HPLC (retention time) 18 min.

(h) Isomers A and B of (5R, 6S, 8R)-2-[(5,6-dihydro-4H-pyrrolo[1,2-b]pyrazol-4-yl)thio]-6-(1-hydroxyethyl)-2-penem-3-carboxylic acid

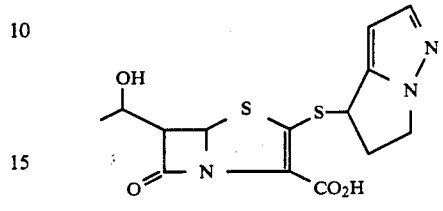

Isomer A

I. R. (KBr disc)cm$^{-1}$: 3380, 2950, 1760, 1580, 1365
U. V. $\lambda_{max}$ (H$_2$O)nm: 252 (sh), 324
N. M. R. $\delta$(D$_2$O)ppm: 1.26 (3H; d; J=5.9Hz; CH$_3$), 2.4~2.9 (1H; m), 2.9~3.5 (1H; m), 3.8~4.0 (1H; m; C6-H), 4.0~4.8 (4H; m), 4.74 (DOH), 5.65 (1H; brs; C5-H), 6.29 (1H; brs; side chain C3-H), 7.55 (1H; brs; side chain C2-H)

HPLC (retention time) 20 min.
Conditions: the same as those described in (g)

Isomer B

I. R. (KBr disc)cm$^{-1}$: 3390, 2950, 1760, 1590, 1370
U. V. $\lambda_{max}$ (H$_2$O)nm 253 (sh), 324
N. M. R. $\delta$(D$_2$O)ppm: 1 26 (3H; d; J=5.9Hz; CH$_3$), 2.4~2.9 (1H; m)) 3.5 (1H; m), 3.8~4.0 (1H; m; C6-H), 4.0~4.8 (4H; m), 5.63 (1H; brs; C5-H), 6.27 (1H; brs; side chain C3-H), 7.55 (1H; brs; side chain C2-H)

HPLC (retention time): 24 min.

EXAMPLE 15

Isomers A and B of (5R, 6S, 8R)-6-(1-hydroxyethyl)-2-[(5,6,7,8-tetrahydroimidazo[1,2-a]pyridin-7-yl)thio]-2-penem-3-carboxylic acid

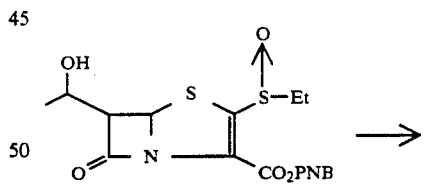

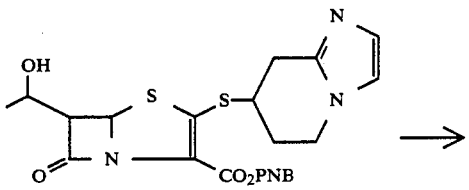

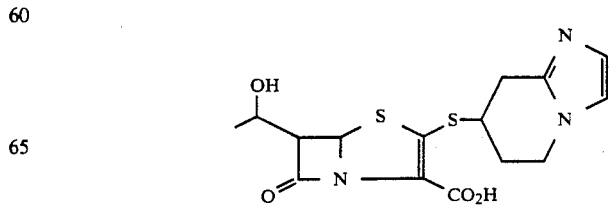

(1) Synthesis of p-nitrobenzyl ester of (5R, 6S, 8R)-6-(1-hydroxyethyl)-2-[(5,6,7,8-tetrahydroimidazo-[1,2-a]pyridin-7-yl)thio]-2-penem-3-carboxylic acid A thiol derivative (292 mg) obtained in the reference example 10 hereunder explained was used and the procedures similar to those disclosed in the example 1-(1) were repeated to obtain the objective compound (yield: 185 mg)

N. M. R. $\delta(CDCl_3)$ppm: 1.36 (3H; d; J=6Hz; $CH_3$), 1.9~2.6 (2H; m; pyridine ring $C_6$-$H_2$), 2.6~3.5 (2H; m; pyridine ring $C_8$-$H_2$), 3.5~3.9 (2H; m; pyridine ring $C_7$-H) and $C_6$-H), 3.9~4.3 (3H; m; pyridine ring $C_5$-$H_2$ and $C_8$-H), 5.12 and 5.42 (each 2H; each ABq; J=14Hz; $CO_2CH_2Ar$), 5.70 (1H; d; J=2Hz, $C_5$-H), 6.75 (1H; brs; imidazole ring $C_3$-H), 6.92 (1H; brs; imidazole ring $C_2$-H), 7.53 (2H; d; J=9Hz; ArH), 8.12 (2H; d; J=9Hz, ArH)

(2) Synthesis of isomers A and B of (5R, 6S, 8R)-6-(1-hydroxyethyl)-2-[(5,6,7,8-tetrahydroimidazo[1,2-a]pyridin-7-yl)thio]-2-penem-3-carboxylic acid The procedures of the example 1-(2) were repeated using the product (71 mg) obtained in the above step (1) to form the objective compounds (isomers A and B).

Isomer A

Yield 13 mg
I. R. (KBr disc)cm$^{-1}$: 1770, 1590
U. V. $\lambda_{max}$ ($H_2O$)nm: 260, 322
N. M. R. $\delta(D_2O)$ppm: 1.38 (3H; d; J=6Hz: $CH_3$), 2.1~2.6 (2H; m; pyridine ring $C_6$-$H_2$), 3.13 (1H; dd; J=18, 7Hz; pyridine ring $C_8$-H), 3.60 (1H; dd; J=18, 5Hz; pyridine ring $C_8$-H), 4.01 (1H; dd; J=7, 2Hz; $C_6$-H), 4.0~4.5 (4H; m; pyridine ring $C_5$-$H_2$, pyridine ring $C_7$-H and $C_8$-H), 4.80 (HOD), 5.75 (1H; d; J=2Hz; $C_5$-H), 7.35 (2H; s; imidazole ring $C_2$-H and $C_3$-H)
HPLC (retention time): 22.7 min.
Conditions
Nucleosil 7$C_{18}$ (10×300 mm)
5% acetonitrile-water
3.65 ml/min.

Isomer B

Yield 15 mg
I. R. (KBr disc)cm$^{-1}$: 1770, 1590
U. V. $\lambda_{max}$ ($H_2O$)nm: 258, 322
N. M. R. $\delta(D_2O)$ppm: 1.38 (3H; d; J=6Hz; $CH_3$), 2.1~2.6 (2H; m; pyridine ring $C_6$-$H_2$), 3.17 (1H; dd; J=18, 7Hz; pyridine ring $C_8$-H), 3.63 (1H; dd; J=18, 6Hz; pyridine ring $C_8$-H), 4.00 (1H; dd; J=7, 2Hz; $C_6$-H), 4.0~4.5 (4H; m; pyridine ring $C_5$-$H_2$, pyridine ring $C_7$-H and $C_8$-H), 4.80 (HOD), 5.78 (1H; d; J=2Hz; $C_5$-H), 7.35 (2H; s; imidazole ring $C_2$-H and $C_3$-H)
HPLC (retention time): 27.7 min.

EXAMPLE 16

Synthesis of the mixture of isomers A and B of (5R, 6S, 8R)-6-(1-hydroxyethyl)-2-[(1-methyl-5,6,7,8-tetrahydroimidazo[1,2-a]pyridinium-7-yl)thio]-2-penem-3-carboxylate

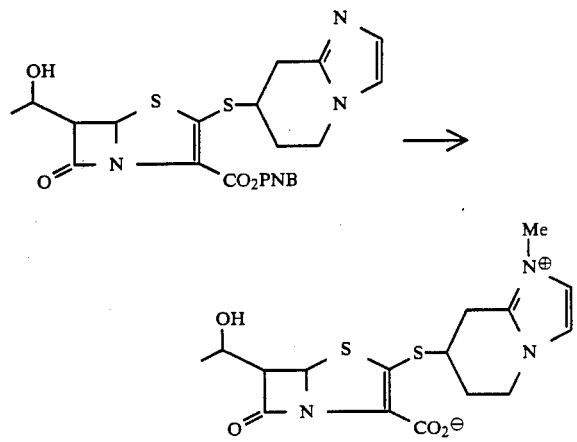

The compound (114 mg) obtained in the example 15 was used and the objective compound (yield: 33 mg) was obtained according to the procedures of the example 2.

I. R. (KBr disc)cm$^{-1}$: 1770, 158
N. M. R. $\delta(D_2O)$ppm: 1.36 (3H; d; J=6Hz; $CH_3$), 2.1~2.7 (2H; m; pyridine ring $C_6$-$H_2$), 3.0~4.4 (7H; m; pyridine ring $C_5$-$H_2$, pyridine ring $C_7$-H, pyridine ring $C_8$-$H_2$, $C_6$-H and $C_8$-H), 3.80 (3H; s; $NCH_3$), 4.80 (HOD), 5.80 (1H; s; $C_5$-H), 7.42 (2H; s; imidazole ring $C_2$-H and $C_3$-H)
HPLC (retention time) 14.4 min.
Conditions
Nucleosil 7$C_{18}$ (10×300 mm)
7% acetonitrile-water
3.65 ml/min.

EXAMPLE 17

Synthesis of (5R, 6S, 8R)-6-(1-hydroxyethyl)-2-[(5,6,7,8-tetrahydro-1,2,4-triazolo[4,3-a]pyridin-7-yl)thio]-2-penem-3-carboxylic acid (mixture of isomers A and B)

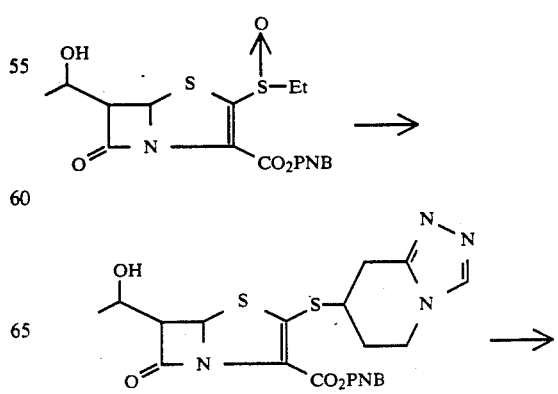

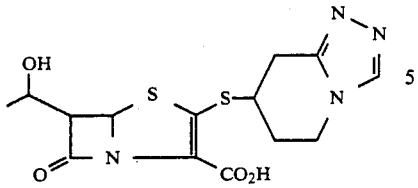

(1) Synthesis of p-nitrobenzyl ester of (5R, 6S, 8R)-6-(1-hydroxyethyl)-2-[(5,6,7,8-tetrahydro-1,2,4-triazolo[4,3-a]pyridin-7-yl)thio]-2-penem-3-carboxylic acid The thiol derivative (213 mg) obtained in the reference example 11 described below was reacted and treated according to the procedures of the example 1-(1) to obtain the objective compound (yield: 186 mg).

M. M. R. δ(CDCl$_3$)ppm 1.40 (3H; d; J=6Hz; CH$_3$), 2.0~2.6 (2H; m; pyridine ring C$_6$-H$_2$), 3.0~4.0 (4H; m; pyridine ring C$_8$-H$_2$, pyridine ring C$_7$-H and C$_6$-H), 4.0~4.4 (3H; m; pyridine ring C$_5$-H$_2$ and C$_8$-H), 5.20 and 5.48 (each 2H; each ABq; J=14Hz; CO$_2$CH$_2$Ar), 5.88 (0.5H; d; J=2Hz; C$_5$-H), 5.91 (0.5H; d; J=2Hz; C$_5$-H), 7.60 (2H; d; J=9Hz; ArH), 8.12 (1H; s; triazole ring C$_3$-H), 8.24 (2H; d; J=9Hz; ArH)

(2) Synthesis of (5R, 6S, 8R)-6-(1-hydroxyethyl)-2-(5,6,7,8-tetrahydro-1,2,4-triazolo[4,3-a]pyridin-7-yl)thio]-2-penem-3-carboxylic acid (mixture of isomers A and B)

The product (70 mg) obtained in the above step (1) was treated according to the procedures of the example 1-(2) and thus, the objective product was prepared (yield: 29 mg).

I. R. (KBr disc)cm$^{-1}$: 1765, 1595
U. V. λ$_{max}$ (H$_2$O)nm: 258, 322
N. M. R. δ(D$_2$O)ppm: 1.38 (3H; d; J=6Hz; CH$_3$), 2.1~2.6 (2H; m; pyridine ring C$_6$-H), 2.9~3.6 (2H; m; pyridine ring C$_8$-H$_2$), 4.00 (1H; dd; J=6, 2Hz; C$_6$-H), 4.0~4.5 (4H; m; pyridine ring C$_5$-H$_2$, pyridine ring C$_7$-H and C$_8$-H), 4.80 (HOD), 5.80 (1H; d; J=2Hz; C$_5$-H), 8.48 (1H; s; triazole ring C$_3$-H)
HPLC (retention time): 14.2 and 15.2 min.
Conditions
Nucleosil 7C$_{18}$ (10×300 mm)
3% acetonitrile-water
3.65 ml/min.

EXAMPLE 18

Synthesis of (5R, 6S, 8R)-6-(1-hydroxyethyl)-2-(methyl-5,6,7,8-tetrahydro-1,2,4-triazolo-[4,3-a]pyridinium-7-yl)thio]-2-penem-3-carboxylate (mixture of isomers A and B; isomers C and D)

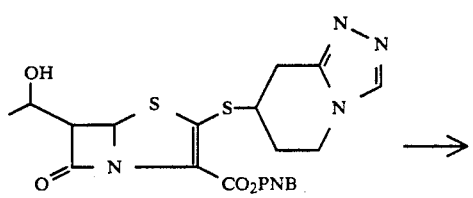

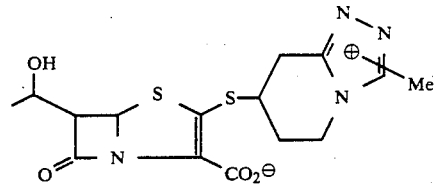

The procedures of the example 2 were repeated, utilizing the product (116 mg) obtained in the example 17, to form the objective compounds:

Mixture of isomers A and B

Yield 15 mg
I. R. (KBr disc)cm$^{-1}$: 1760, 1580
U. V. λ$_{max}$ (H$_2$O)nm: 255, 323
N M. R. δ(D$_2$O)ppm: 1.36 (3H; d; J=6Hz; CH$_3$), 2.1~4.6 (9H; m; pyridine ring C$_6$-H$_2$, pyridine ring C$_8$-H$_2$, pyridine ring C$_5$-H$_2$, pyridine ring C$_7$-H, C$_6$-H and C$_8$-H), 4.04 (3H; s; NCH$_3$), 4.86 (HOD), 5.80 (1H; d; J=2Hz; C$_5$-H), 8.80 (1H; s; triazole ring C$_3$-H)
HPLC (retention time): 14.4 min.
Conditions
Nucleosil 7C$_{18}$ (10×300 mm)
5% acetonitrile-water
3.65 ml/min.

Isomer C

Yield 7 mg
I. R. (KBr disc)cm$^{-1}$: 1765, 1590
U. V. λ$_{max}$ (H$_2$O)nm: 258, 323
N. M. R. δ(D$_2$O)ppm: 1.39 (3H; d; J=6Hz; CH$_3$), 2.2~2.7 (2H; m; pyridine ring C$_6$-H$_2$), 3.32 (1H; dd; J=18, 7Hz; pyridine ring C$_8$-H), 3.68 (1H; dd; J=18, 5Hz; pyridine ring C$_8$-H), 4.03 (1H; dd; J=6, 2Hz; C$_6$-H), 4.16 (3H; s; NCH$_3$), 4.2~4.6 (4H; m; pyridine ring C$_5$-H$_2$, pyridine ring C$_7$-H; and C$_8$-H), 4.80 (HOD), 5.83 (1H; d; J=2Hz; C$_5$-H)
HPLC (retention time): 21.2 min.

Isomer D

Yield 6 mg
I. R. (KBr disc)cm$^{-1}$: 1765, 1590
U. V. λ$_{max}$ (H$_2$O)nm: 260, 322
N. M. R. δ(D$_2$O)ppm: 1.36 (3H; d; J=6Hz; CH$_3$), 2.3~2.6 (2H; m; pyridine ring C$_6$-H$_2$), 3.21 (1H; dd; J=18, 7Hz; pyridine ring C$_8$-H), 3.68 (1H; dd; J=18, 5Hz; pyridine ring C$_8$-H), 4.06 (1H; dd; J=6, 2Hz; C$_6$-H), 4.16 (3H; s; NCH$_3$), 4.0~4.6 (4H; m; pyridine ring C$_5$-H$_2$, pyridine ring C$_7$-H and C$_8$-H), 480 (HOD), 5.80 (1H; d; J=2Hz; C$_5$-H)
HPLC (retention time) 29.6 min.

REFERENCE EXAMPLE A

Synthesis of 6,7-dihydro-7-mercapto-5H-pyrrolo[1,2-c]imidazole trifluoromethane sulfonate

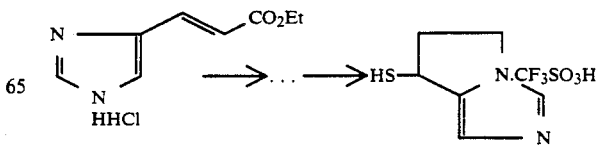

(1) Ethyl 3-(imidazol-4-yl)-3-(p-methoxybenzylthio) propionate 3 g of ethyl ester of urocanic acid hydrochloride (W. Hubball and F. L. Pyman, J. Chem. Soc., 1928, 26) was made alkaline with aqueous solution of sodium bicarbonate and saturated with NaCl and extracted with chloroform and dried over Na₂SO₄. The solution was concentrated to 50 ml under reduced pressure, added 3.1 g of methoxybenzylmercaptan and 3.44 g of DBU and stirred for 24 hours at room temperature under argon. The solvent was distilled off under reduced pressure, the residue was purified by column chromatography utilizing 40 g of silica gel and benzene-ethyl acetate (1:1 v/v) as an eluent to obtain 4.8 g of the objective compound.

N. M. R. $\delta$(CDCl₃) 1.18 (3H; t; J=6Hz), 2.83~3.00 (2H; m), 3.60 (2H; s), 3.76 (3H; s), 4.07 (2H; q; J=6Hz), 4.23 (1H; t; J=6Hz), 6.13 (1H; brs), 6.75 (2H; d; J=9Hz), 6.86 (1H; s), 7.13 (2H; d; J=9Hz), 7.53 (1H; s)

(2) 3-(Imidazol-4-yl)-3-(p-methoxybenzylthio)propanol 4.8 g of the compound obtained in the above step (1) was dissolved in 50 ml of THF, cooled to 0°~5° C., added 0.33 g of lithium borohydride and stirred for 17 hours at room temperature. The solvent was distilled off under reduced pressure, added chloroform, water and ammonium chloride to the residue obtained and the organic phase was separated. The organic phase was dried over Na₂SO₄ and the solvent was distilled off under reduced pressure. The objective compound was obtained after purifying the residue by passing it through a column packed with 50 g of silica gel and eluting the product with chloroform-methanol (95:5 v/v) (yield: 1.98 g).

N. M. R. $\delta$(CDCl₃)ppm: 1.90~2.30 (2H; m), 3.50 (2H; s), 3.69 (3H; s), 3.94 (1H; t; J=6Hz), 6.69 (2H; d; J=9Hz), 6.81 (1H; s), 7.06 (2H; d; J=9Hz), 7.49 (1H; s)

(3) 3-(Imidazol-4-yl)-3-(p-methoxybenzylthio)propyl chloride 1.2 g of the compound obtained in the above step (2) was dissolved in a mixed solvent consisting of THF (30 ml) and carbon tetrachloride (30 ml), added 2.26 g of triphenylphosphine and stirred for 17 hours at 50° C. The reaction mixture was subjected to distillation under reduced pressure and the resulting residue was purified by column chromatography utilizing 30 g of silica gel and benzenemethanol (97:3 v/v) as an eluent. Thus, the objective compound was obtained in the yield of 0.41 g.

N. M. R. $\delta$(CDCl₃)ppm: 2.15~2.50 (2H; m), 3.55 (2H; s), 3.74 (3H; s), 4.00 (1H; t; J=6Hz), 6.74 (2H; d; J=9Hz), 6.86 (1H; s), 7.12 (2H; d; J=9Hz), 7.57 (1H; s)

(4) 6,7-Dihydro-7-(p-methoxybenzylthio)-5H-pyrrolo[1,2-c]imidazole 400 mg of the compound obtained in the preceeding step (3) was dissolved in 10 ml of acetone, added 2.0 g of sodium iodide and stirred for 17 hours at room temperature. The mixture was further refluxed under heating for eight hours and distilled off the solvent under reduced pressure. To the residue were added chloroform, water and sodium carbonate (3 g), isolated the organic phase, dried over Na₂SO₄ and distilled off the solvent under reduced pressure. The residue was purified by column chromatography utilizing 10 g of silica gel and chloroform-methanol (99:1 v/v) as an eluent to obtain the objective compound (yield: 250 mg).

N. M. R. $\delta$(CDCl₃)ppm: 2.27~2.60 (1H; m), 2.65~3.15 (1H; m), 3.70 (2H; s), 3.75 (3H; s), 3.80~4.20 (3H; m), 6.76 (1H; s), 6.78 (2H; d; J=9Hz), 7.18 (2H; d; J=9Hz), 7.34 (1H; s)

(5) 6,7-Dihydro-7-mercapto-5H-pyrrolo[1,2-c]imidazole trifluoromethane sulfonate

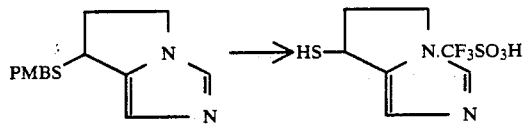

To 6,7-dihydro-7-p-methoxybenzylthio-5H-pyrrolo[1,2-c]imidazole (400 mg) obtained in the above step (4) there were added anisole (1.5 ml), trifluoroacetic acid (9 ml) and trifluoromethane sulfonic acid (0.36 ml) and stirred for 30 minutes at room temperature. The reaction solution was concentrated under reduced pressure and further concentrated after the addition of xylene (20 ml). Such procedures were repeated twice and the resulting residue was washed with ether. Ether was removed by decantation, dried under reduced pressure to form the objective compound (yield: 440 mg).

N. M. R. $\delta$(D₂O)ppm: 2.50~2.80 (1H; m), 3.00~3.43 (1H; m), 4.20~4.70 (3H; m), 4.80 (HOD), 7.33 (1H; 2), 8.60 (1H; s)

REFERENCE EXAMPLE 1

Synthesis of 6,7-dihydro-7-mercapto-5H-pyrrolo[2,1-c]-1,2,4-triazole trifluoro-methane sulfonate

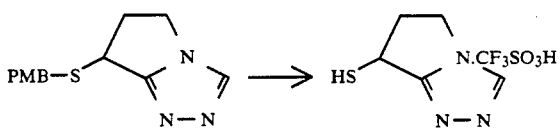

Utilizing 6,7-dihydro-7-p-methoxybenzylthio-5H-pyrrolo [2,1-c]-1,2,4-triazole (280 mg), the procedures of the reference example A were repeated to obtain the objective compound (yield: 361 mg; transparent colorless oil).

N. M. R. $\delta$(DMSO-d₆+D₂O)ppm: 1.8~2.6 (1H; m), 3.0~3.6 (1H; m), 4.1~4.5 (2H; m), 4.65 (1H; dd; J=8, 4Hz), 9.50 (1H; s)

REFERENCE EXAMPLE 2

Synthesis of 6,7-dihydro-6-mercapto-3-trifluoromethyl-5H-pyrrolo[2,1-c]-1,2,4-triazole trifluoromethane sulfonate

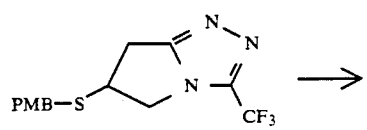

-continued

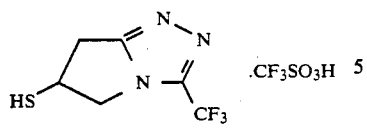.CF₃SO₃H

According to the procedures similar to those described in the reference example A, the above described compound was obtained, as pale yellow oil (231 mg), from 6,7-dihydro-6-p-methoxybenzylthio-3-trifluoromethyl-5H-pyrrolo[2,1-c]-1,2,4-triazole (116 mg).

N. M. R. δ(D₂O)ppm: 3.08 (1H; dd; J=18, 7Hz), 3.68 (1H; dd; J=18, 7Hz), 4.1~4.7 (3H; m), 4.80 (HOD)

The following compounds were also prepared according to the procedures similar to those disclosed in the reference example A.

REFERENCE EXAMPLE 3

3-Amino-6,7-dihydro-7-mercapto-5H-pyrrolo[2,1-c]-1,2,4-triazole trifluoromethane sulfonate

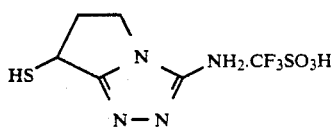

REFERENCE EXAMPLE 4

3-Chloro-6,7-dihydro-7-mercapto-5H-pyrrolo[2,1-c]-1,2,4-triazole trifluoromethane sulfonate

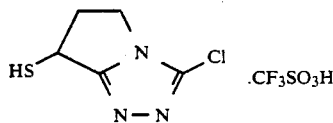

N. M. R. δ(D₂O)ppm: 2.50~2.95 and 3.15~3.60 (1H; m), 4.05~4.80 (3H; m), 4.80 (HOD)

REFERENCE EXAMPLE 5

2-Amino-6,7-dihydro-7-mercapto-5H-pyrrolo[2,1-b]-1,2,4-triazole trifluoromethane sulfonate

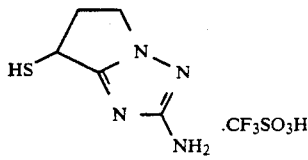

N. M. R. (D₂O)ppm: 2.60~2.90 and 3.18~3.60 (1H; m), 4.10~4.75 (3H; m), 4.80 (HOD)

REFERENCE EXAMPLE 6

2-Chloro-6,7-dihydro-7-mercapto-5H-pyrrolo[2,1-b]-1,2,4-triazole trifluoromethane sulfonate

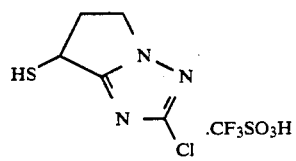

N. M. R. δ(D₂O)ppm: 2.49~2.80 and 3.10~3.50 (1H; m), 4.05~4.58 (3H; m), 4.80 (HOD)

REFERENCE EXAMPLE 7

6.7-Dihydro-6-mercapto-5H-pyrrole[1,2-c]thiazolium trifluoromethane sulfonate

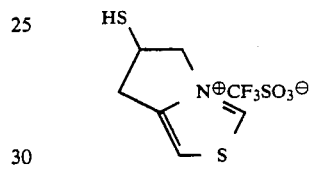

N. M. R. δ(D₂O)ppm: 3.15 (1H; dd), 3.70 (1H; dd), 4.2~5.2 (3H; m), 4.74 (DOH), 7.84 (1H; d; J=1.9Hz), 9.83 (1H; d; J=19.Hz)

REFERENCE EXAMPLE 8

5,6-Dihydro-4-mercapto-4H-pyrrolo[1,2-c]-1,2,3-triazole trifluoromethane sulfonate

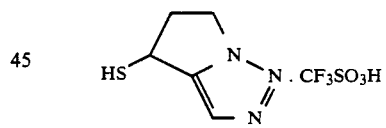

N. M. R. δ(D₂O)ppm: 2 5~3.1 (1H; m), 3.2~3.7 (1H; m), 4.4~5.1 (3H; m), 4.74 (DOH), 8.20 (1H; s)

REFERENCE EXAMPLE 9

5,6-Dihydro-4-mercapto-4H-pyrrolo[1,2-b]pyrazole trifluoromethane sulfonate

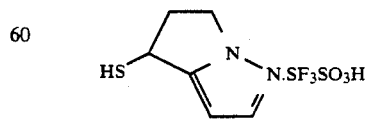

N. M. R. δ(D₂O)ppm: 2.4~3.0 (1H; m), 3.0~3.6 (1H; m), 4.1~4.8 (3H; m), 4.74 (DOH), 6.55 (1H; d; J=3Hz), 7.98 (1H; d; J=3Hz)

REFERENCE EXAMPLE 10

Synthesis of 7-mercapto-5,6,7,8-tetrahydroimidazo[1,2-a]pyridine trifluoromethane sulfonate

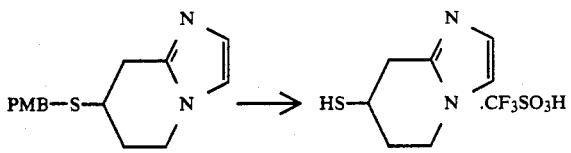

Using 7-p-methoxybenzylthio-5,6,7,8-tetrahydroimidazo[1,2-a]pyridine (249 mg), the objective compound was prepared according to the procedures similar to those disclosed in the reference example A. The yield thereof was 292 mg (transparent colorless oil).

REFERENCE EXAMPLE 11

Synthesis of 7-mercapto-5,6,7,8-tetrahydro-1,2,4-triazolo[4,3-a]pyridine trifluoromethane sulfonate

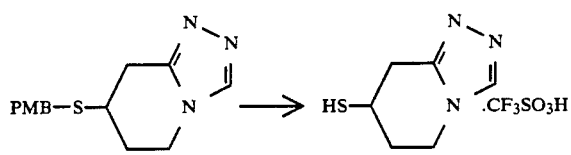

Starting from 307 mg of 7-p-methoxybenzylthio-5,6,7,8-tetrahydro-1,2,4-triazolo[4,3-a]pyridine, the procedures similar to those disclosed in the reference example A were repeated and 435 mg of the objective compound was obtained as transparent colorless oily product.

N. M. R. $\delta(C_2O+DMSO\text{-}d_6)$ppm: 2.1~2.7 (2H; m), 3.31 (1H; dd; J=18, 7Hz), 3.80 (1H; dd; J=18, 7Hz), 3.6~3.9 (1H; m), 4.4~4.6 (2H; m), 9.19 (1H; s)

EXAMPLE 19

Synthesis of (5R, 6S, 8R)-2-[(2,3-dihydro-1H-indolizinium-1-yl)thio]-6-(1-hydroxyethyl)-penem-3-carboxylate

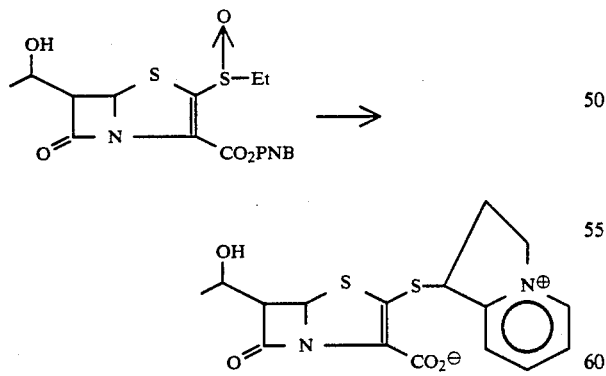

In DMF (3 ml), there were dissolved 180 mg of p-nitrobenzyl (5R, 6S, 8R)-2-ethylsulfinyl-6-(1-hydroxyethyl)-penem-3-carboxylate (prepared according to the example 1 disclosed in Japanese Patent Laid-Open No. 56987/1985) and 271 mg of 2,3-dihydro-1-mercapto-1H-indolizinium trifluoromethane sulfonate, added 108 mg of diisopropylethyl amine in nitrogen atmosphere while cooling at −40° C. and stirred for 30 minutes at that temperature. The reaction liquid was poured into ether, subjected to centrifugation and the supernatant liquid was removed by decantation. The precipitates were dissolved in 50% THF-water (40 ml), added 4.16 g of ammonium chloride and 2.08 g of iron powder under ice cooling and vigorously stirred for 50 minutes at that temperature. The reaction solution was filtered with Celite ® (manufactured and sold by Johns-Manville), the filtrate was concentrated under reduced pressure and washed with ethyl acetate. The water phase was concentrated in vacuo and the resulting concentrate was purified by passing it through a column packed with Diaion HP-20 (1.8 cm×22 cm). The fractions eluted with 350 ml of water were discarded, the fractions eluted with 5% THF-water were concentrated in vacuo, purified by HPLC. [carrier: Nucleosil 7C$_{18}$ (10 mm×300 mm); solvent: 7% acetonitrile-water; flow rate: 3.65 ml/min.] and liophilized to obtain the objective product as pale yellow powder (yield: 30 mg).

I. R. (KBr disc)cm$^{-1}$: 1760, 1590
U. V. $\lambda_{max}$ (H$_2$O)nm: 265, 325
N. M. R. $\delta$(D$_2$O)ppm: 1.33 (3H; d; J=6Hz; CH$_3$), 2.48~2.92 (1H; m; indolizinium ring C$_2$-H), 2.92~3.40 (1H; m; indolizinium ring C$_2$-H), 3.95~5.20 (5H; m; indolizinium ring C$_1$-H and C$_3$-H$_2$, C$_6$-H and C$_8$-H), 4.80 (HOD), 5.64 (1/3H; d; J=2Hz; C$_5$-H), 5.76 (2/3H; d; J=2Hz; C$_5$-H), 7.92~8.32 (2H; m; indolizinium ring C$_6$-H and C$_8$-H). 8.58 (1H; dt; J=1, 7Hz; indolizinium ring C$_7$-H), 8.88 (1H; dd; J=1, 7Hz; indolizinium ring C$_5$-H)

HPLC (retention time): 13.0 min. and 13.6 min.
Elemental Analysis (%) (as C$_{16}$H$_{16}$N$_2$O$_4$S$_2$.H$_2$O)

|  | C | H | N |
|---|---|---|---|
| Calculated: | 49.98 | 4.72 | 7.29 |
| Found: | 50.22 | 4.75 | 7.38 |

EXAMPLE 20

Preparation of (5R, 6S, 8R)-2-[(2,3-dihydro-1H-indolizinium-2-yl)thio]-6-(1-hydroxyethyl)-penem-3-carboxylate

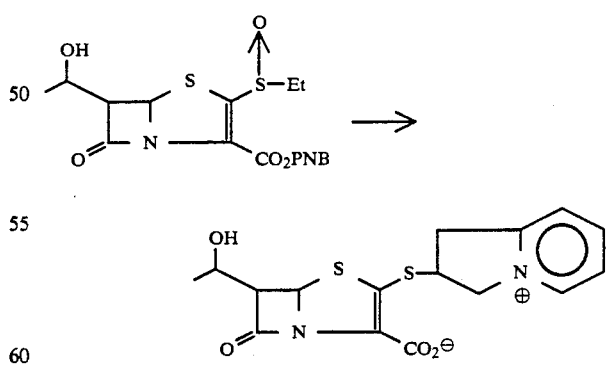

According to the procedures similar to those in the example 19, the objective product was prepared as pale yellow powder, utilizing 2,3-dihydro-2-mercapto-1H-indolizinium trifluoromethane sulfonate.

Isomer A

U. V. $\lambda_{max}$ (H$_2$O)nm: 264, 322

HPLC (retention time): 11.7 min.
Carrier: Nucleosil 7C$_{18}$ (10×300 mm)
Solvent: 7% acetonitrile-water
Flow rate: 3.65 ml/min.

Isomer B

U. V. $\lambda_{max}$ (H$_2$O)nm: 264, 322
HPLC (retention time): 13.4 min.

EXAMPLE 21

Preparation of (5R, 6S, 8R)-2-[(6,7-dihydro-5H-pyrrolo-[1,2-a]imidazol-7-yl)thio]-6-(1-hydroxyethyl)-penem-3-carboxylic acid

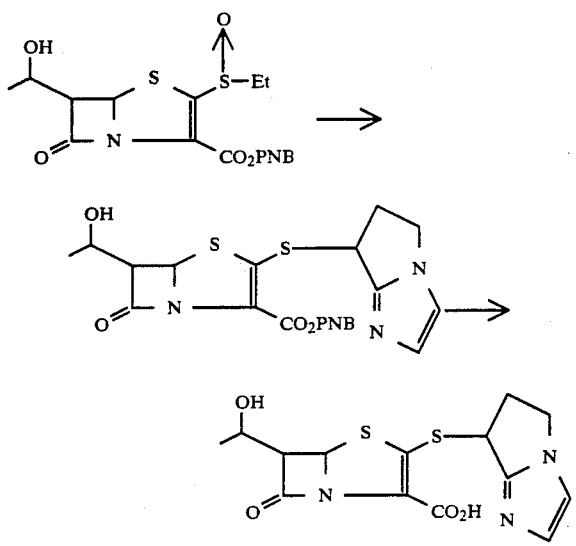

(1) Synthesis of p-nitrobenzyl (5R, 6S, 8R)-6-(1-hydroxyethyl)-2-[(6,8-dihydro-5H-pyrrolo[1,2-a]imidazol-7-yl)thio]penem-3carboxylate p-Nitrobenzyl (5R, 6S, 8R)-2-ethylsulfinyl-6-(1-hydroxyethyl)-penem-3-carboxylate (190 mg) and 6,7-dihydro-7-mercapto-5H-pyrrolo [1,2-a]imidazole trifluoromethane sulfonate (261 mg) were dissolved in 5 ml of DMF, added 232 mg of diisopropylethylamine while cooling the solution at −50° C. and stirred for 30 minutes at that temperature. The reaction solution was diluted with ethyl acetate and the solvent was distilled off under reduced pressure after washing and drying over MgSO$_4$. The residue was purified by column chromatography using 18 g of silica gel (chloroform: methanol=5:1 v/v) and the caramel-like objective compound was obtained (yield 178 mg).

N. M. R. δ(CDCl$_3$)ppm: 1.40 (3H; d; J=6Hz; CH$_3$), 2.6∼3.5 (2H; m; pyrroline ring C$_6$-H$_2$), 3.7∼4.4 (4H; m; pyrroline ring C$_5$-H$_2$, C$_6$-H and C$_8$-H), 4.80 (1H; dd; J=4, 7Hz; pyrroline ring C$_7$-H), 5.18 and 5.36 (each 0.5H; each ABq; J=14Hz; CO$_2$CH$_2$Ar), 5.28 and 5.41 (each 0.5H; each ABq; J=14Hz; CO$_2$CH$_2$Ar), 5.75 (0.5H; d; J=2Hz; C$_5$-H), 5.98 (0.5H; d; J=2Hz; C$_5$-H), 6.92 (0.5H; d; J=2Hz; imidazole ring-H), 6.96 (0.5H; d; J=2Hz; imidazole ring-H), 7.16 (1H; d; J=2Hz; imidazole ring-H), 7.58 (1H; d; J=9Hz; ArH), 7.64 (1H; d; J=9Hz; ArH), 8.16 (1H; d; J=9Hz; ArH), 8.24 (1H; d; J=9Hz; ArH).

(2) Synthesis of (5R, 6S, 8R)-2-[(6,7-dihydro-5H-pyrrolo [1,2-a]imidazol-7-yl)thio]-6-(1-hydroxyethyl)-penem-3-carboxylic acid:

The compound (178 mg) obtained in the above step (1) was dissolved in a mixture of THF (15 ml) and phosphate buffer (15 ml; pH 7.0), added 200 mg of 10% palladium-carbon to carry out catalytic reduction at room temperature for two hours After removing the catalyst by filtration, the resulting filtrate and wash liquid were combined, concentrated and washed with ethyl acetate. The water phase was concentrated and the concentrate was purified by column chromatography using Diaion HP-20 (1.8 cm×20 cm). After removing the fractions eluted by 50 ml of water, the fractions eluted by 150 ml of water and 80 ml of 5% THF-water were combined together, concentrated, purified by HPLC. [carrier: Nucleosil 7C$_{18}$ (10×300 mm); solvent: 5% acetonitrile-water; flow rate: 3.65 ml/min.]and liophilized to obtain 58 mg of the objective product as colorless powder.

I. R. (KBr disc)cm$^{-1}$: 1760, 1580
U. V. $\lambda_{max}$ (H$_2$O)nm: 325
N. M. R. δ(D$_2$O)ppm: 1.33 (1.5H; d; J=6Hz; CH$_3$), 1.36 (1.5H; d; J=6Hz; CH$_3$), 2.8∼3.1 (1H; m; pyrroline ring C$_6$-H), 3.1∼3.5 (1H; m; pyrroline ring C$_6$-H), 4.0∼4.6 (4H; m; pyrroline ring C$_5$-H$_2$, C$_6$-H and C$_8$-H), 4.80 (HOD), 5.66 (0.5H; d; J=2Hz; C$_5$-H), 5.73 (0.5H; d; J=2Hz; C$_5$-H), 7.2∼7.4 (2H; m; imidazole ring-H)
HPLC (retention time): 13.6 min.

EXAMPLE 22

(1) Synthesis of p-nitrobenzyl (5R, 6S, 8R)-6-(1-hydroxyethyl)-2-[(6,7-dihydro-5H-pyrrolo[1,2-a]imidazol-6-yl)thio]-2-penem-3-carboxylate

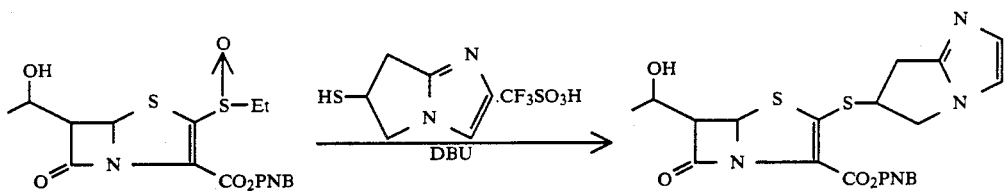

p-Nitrobenzyl (5R, 6S, 8R)-2-ethylsulfinyl-6-(1-hydroxyethyl)-penem-carboxylate (213 mg) was dissolved in a mixture of acetonitrile (5 ml) and THF (2 ml) and cooled to −40° C. to −50° C. To the solution, there were added a solution of 6,7-dihydro-6-mercapto-5H-pyrrolo [1,2-a]imidazole.trifluoromethane sulfonate (390 mg) in THF (3 ml) and DBU (410 mg) and stirred for 20 minutes at the same temperature mentioned above. After the reaction was completed, 30 ml of ethyl acetate was added, washed with water and saturated NaCl solution, dried over Na$_2$SO$_4$ and concentrated under reduced pressure. The resultant residue was passed through a column packed with 15 g of silica gel and eluted with chloroform-methanol (19:1 v/v) and the fractions containing the objective product were collected and concentrated. Thus, 225 mg of the objective compound was obtained as yellowish oil.

N. M. R. δ(CDCl₃)ppm: 1.38 (3H; d; J=6Hz; CH₃), 2.8~3.7 (2H; m;

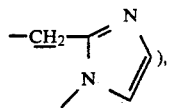

3.7~4.7 (5H; m;

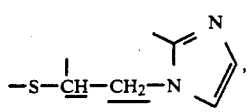

C₆-H, C₈-H), 5.32 (2H; ABq; J=14Hz; —COO—CH₂—), 5.76 (1H; d; J=2Hz; C₅-H), 6.87 and 7.05 (each 1H; each d; J=1Hz; imidazole ring-H), 7.59 and 8.18 (each 2H; each d; J=9Hz; —C₆H₄NO₂)

TLC (thin layer chromatography), Rf: 0.4
Conditions
Silica Gel Plate (Merck: 0.25 mm in thick)
Developing Solvent: chloroform-methanol (9:1 v/v)

(2) Synthesis of (5R, 6S, 8R)-6-(1-hydroxyethyl)-2-[(6,7-dihydro-5H-pyrrolo[1,2-a]imidazol-6-yl)-thio]-2-penem-3-carboxylic acid (isomers A and B)

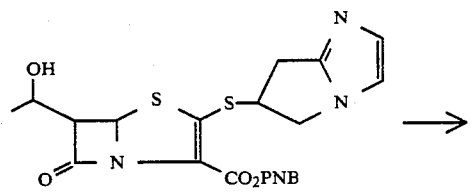

The compound (84 mg) obtained in the above step (1) was dissolved in a mixture of THF (5 ml) and phosphate buffer (5 ml; pH 7), added 10% palladium-carbon (160 mg) to carry out catalytic reduction at room temperature for 3 hours under atm. of hydrogen After removing the catalyst by filtration, the filtrate was diluted with water and washed with ether-ethyl acetate mixed solvent (1:1 v/v). The water phase was concentrated to about 30 ml under reduced pressure and passed through a column packed with Diaion HP-20 (1.8 cm×22 cm) to purify the product. The fractions eluted with 100 ml of water were discarded while the fractions eluted with 5% THF-water (showing maximum U. V. absorption at around 320 nm) were collected and concentrated. The concentrate was subjected to HPLC [carrier: Nucleosil 7C₁₈ (10×300 mm); solvent: 5% acetonitrile-water; flow rate: 4 ml/min.]and the fractions containing the objective compound and having the retention time of 14 min. were collected, concentrated under reduced pressure and liophilized to obtain the objective product (pale yellow powder: yield 24 mg).

I. R. (KBr disc)cm⁻¹: 3400, 1765, 1585
U. V. λ$_{max}$ (H₂O)nm: 323
N. M. R. δ(D₂O)ppm: 1.37 (3H; d; J=6Hz; CH₃), 3.2 and 3.6 (each 1H; each m;

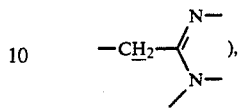

4.02 (1H; dd; J=2, 6Hz; C₆-H), 4.1~4.5 (4H; m;

C₈-H), 4.80 (HOD), 5.79 (1H; d; J=2Hz; C₅-H), 7.22 (2H; brs; imidazole ring-H).

While the product was purified by HPLC [carrier: C₁₈-octadecylsilane (SSC-ODS-762 manufactured by Senshu Kagaku Co., Ltd.), 20×300 mm; solvent: 6% acetonitrile-water; flow rate: 10 ml/min.]and the fractions containing the objective compound and showing the retention time of 15 min. and 16.5 min. respectively. Thus, isomers A and B were obtained as pale yellow powder after the liophilization.

Isomer A

N. M. R. δ(D₂O)ppm: 1.37 (3H; d; J=6Hz; CH₃), 2.96~3.23 (1H; m); 3.46~3.80 (1H; m), 4.00 (1H; dd; J=2, 6Hz, C₆-H), 4.10~4.50 (2H; m), 4.50~4.75 (2H; m), 4.80 (HOD), 5.80 (1H; d; J=2Hz; C₅-H), 7.30 (2H; s; imidazole ring-H)

HPLC (retention time): 15 min.

Isomer B

N. M. R. δ(D₂O)ppm: 1.36 (3H; d; J=6Hz; CH₃), 3.14~3.44 (1H; m), 3.63~3.93 (1H; m), 3.99 (1H; dd; J=2, 6Hz; C₆-H), 4.10~4.50 (2H; m), 4.80 (HOD), 5.78 (1H; d; J=2Hz; C₅-H), 7.35 (2H; s; imidazole ring-H)

HPLC (retention time): 16.5 min.

EXAMPLE 23

Synthesis of (5R, 6S, 8R)-6-(1-hydroxyethyl)-2-[(6,7-dihydro-1-methyl-5H-pyrrolo[1,2-a]imidazolium-6-yl)thio]-2-penem-3-carboxylate

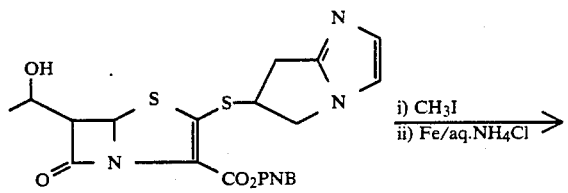

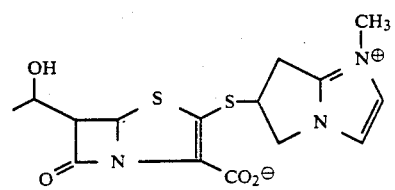

The compound (220 mg) obtained in the step (1) of the example 22 was dispersed in a mixture of acetone (3 ml) and THF (5 ml), added 0.84 ml of methyl iodide under ice cooling and reacted at 3° C. for 16 hours. The reaction solution was concentrated to dryness under reduced pressure and the resultant residue was washed with ether and dried. The resulting powder was dissolved in a mixed liquid consisting of 20 ml of THF and 20 ml of water, added 4.4 g of ammonium chloride and 2.2 g (100 mesh) of iron powder and vigorously stirred for one hour. Insolubles were removed by filtration using Celite ® (Johns-Manville), the filtrate was diluted with water, washed with ethyl acetate-ether (1:1) mixed liquid, then the water phase was concentrated to 30 ml under reduced pressure and purified by passing the concentrate through a column packed with Diaion HP-20 (1.8 cm×23 cm). After removing the fractions eluted with 100 ml of water, the fractions eluted with 5% THF-water were collected and concentrated under reduced pressure. The concentrate was then subjected to HPLC [carrier: Nucleosil 7C$_{18}$ (10×300 mm); solvent: 3% acetonitrile-water; flow rate: 4 ml/min.]and the fractions containing the objective compound and showing the retention time of 23 min. was collected, concentrated in vacuo and dried to obtain the objective compound (yield 54 mg; pale yellow powder)

I. R. (KBr disc)cm$^{-1}$: 3400, 1770, 1590

U. V. $\lambda_{max}$ (H$_2$O)nm: 324

N. M. R. δ(D$_2$O) 1.36 (3H; d; J=6Hz; CH-C$\underline{H}_3$), 3.4 (2H; brm;

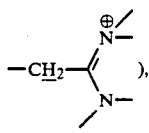

3.83 (3H; s; N-CH$_3$), 4.01 (1H; dd; J=2, 6Hz; C$_6$-H), 4.2~4.5 (4H; m;

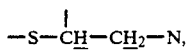

C$_8$-N), 4.80 (HOD), 5.79 (1H; d; J=2Hz; C$_5$-H), 7.43 (2H; s; imidazolium ring-H)

EXAMPLE 24

Synthesis of (5R, 6S, 8R)-6-(1-hydroxyethyl)-2-[(6,7-dihydro-5H-pyrrolo[1,2-c]imidazol-6-yl)-thio]-2-penem-3-carboxylic acid (isomers A and B)

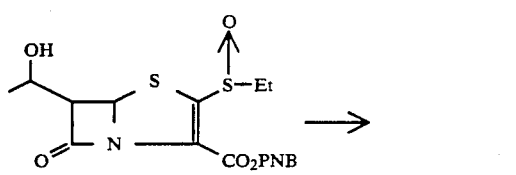

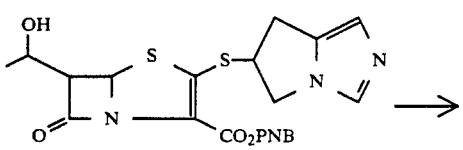

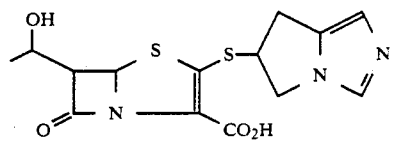

(1) Synthesis of p-nitrobenzyl (5R, 6S, 8R)-6-(1-hydroxyethyl)-2-[(6,7-dihydro-5H-pyrrolo[1,2-c]imidazol-6-yl)thio]-2-penem-3-carboxylate p-Nitrobenzyl (5R, 6S, 8R)-2-ethylsulfinyl-6-(1-hydroxyethyl)-2-penem-3-carboxylate (213 mg) was dissolved in a mixture of THF (4 ml) and acetonitrile (3 ml) and stirred at −50° C. To the solution, was added a solution of 6,7-dihydro-6-mercapto-5H-pyrrolo[1,2-c]-imidazole trifluoromethane sulfonate (360 mg), obtained in the reference example 16-(6), in THF (3 ml) and 380 mg of DBU and the mixture was stirred for 15 minutes at −50° C. Ethyl acetate (30 ml) was added to the reaction liquid and washed with water, then with saturated NaCl solution, dried over Na$_2$SO$_4$ and concentrated under reduced pressure. The resulting residue was purified by column chromatography using 10 g of silica gel (eluent=CHCl$_3$: CH$_3$OH (19:1 v/v)) and thus the objective compound (yield: 94 mg) was obtained as yellow oil (a part thereof being solidified).

N. M. R. δ(CDCl$_3$)ppm: 1 39 (3H; d; J=6Hz; CH$_3$), 2.8~3.6 (2H; m), 3.81 (1H;. dd; J=2, 6Hz; C$_6$-H), 4.0~4.6 (4H; m), 5.33 (2H; ABq; J=14Hz; —OCH$_2$Ar), 5.76 (1H; d; J=2Hz; C$_5$-H), 6.76 (1H; s;

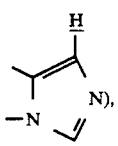

7.45 (1H; s;

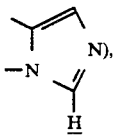

7.60 (2H; d; J=9Hz; 2×ArH), 8.20 (2H; d; J=9Hz; 2×ArH)

(2) Synthesis of (5R, 6S, 8R)-6-(1-hydroxyethyl)-2-[(6,7-dihydro-5H-pyrrolo[1,2-c]imidazol-6-yl)thio]-2-penem-3-carboxylic acid (isomers A and B)

The compound (94 mg) obtained in the preceeding step (1) was dissolved in a mixture of THF (7 ml) and phosphate buffer (7 ml; pH 7), added 180 mg of 10% palladium-carbon to carry out catalytic reduction at room temperature for 4.5 hours under 1 atm. of hydrogen. The catalyst was removed by filtration, then the filtrate was diluted with water and washed with 1:1 mixture of ether and ethyl acetate. The water phase was concentrated to 30 ml and passed through a column packed with Diaion HP-20 (1.8 cm×23 cm) to purify.

After removing the fractions eluted with 100 ml of water, the fractions eluted with 5% acetonitrile-water and showing maximum U. V. absorption at 323nm were combined together and concentrated under reduced pressure. The concentrate was further purified by HPLC [carrier: Nucleosil 7C$_{18}$ (10×300 mm); solvent: 5% acetonitrile-water; flow rate: 4 ml/min.], the fractions showing the retention time of 16 min. and 21 min. were collected, concentrated in vacuo and lyophilized to obtain the objective isomers A and B respectively, as pale yellow powder.

Isomer A

Yield 13 mg
I. R. (KBr disc)cm$^{-1}$: 3400, 1765, 1620, 1580
U. V. $\lambda_{max}$ (H$_2$O)nm: 323
N. M. R. $\delta$(D$_2$O)ppm: 1.37 (3H; d; J=6Hz; CH$_3$), 3.0~3.8 (2H; m), 4.01 (1H; dd; J=2, 6Hz; C$_6$-H), 4.20~4.50 (4H; m), 4.80 (HOD), 5.79 (1H; d; J=2Hz; C$_5$-H), 7.11 (1H; s; imidazole ring-H), 8.37 (1H; s; imidazole ring-H)
HPLC (retention time): 16 min.

Isomer B

Yield 10 mg
I. R. (KBr disc)cm$^{-1}$: 3400, 1765, 1585
U. V. $\lambda_{max}$ (H$_2$O)nm: 323
N. M. R. $\delta$(D$_2$O)ppm: 1.37 (3H; d; J=6Hz; CH$_3$), 2.9~3.80 (2H; m), 4.01 (1H; dd; J=2, 6Hz; C$_6$-H), 4.20~4.60 (4H; m), 4.80 (HOD), 5.78 (1H; d; J=2Hz; C$_5$-H), 7.11 (1H; s; imidazole ring-H), 8.36 (1H; s; imidazole ring-H)
HPLC (retention time): 21 min.

EXAMPLE 25

Synthesis of (5R, 6S, 8R)-6-(1-hydroxyethyl)-2-[(6,7-dihydro-2-methyl-5H-pyrrolo[1,2-c]imidazolium-6-yl)thio]--penem-3-carboxylate (isomers A and B)

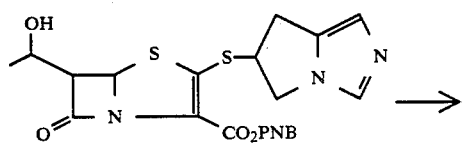

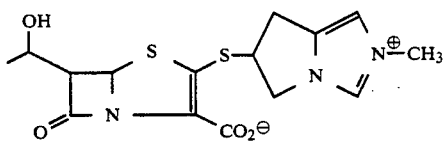

The compound (60 mg) obtained in the step (1) of the example 24 was dissolved in 4 ml of acetone, added 0.5 ml of methyl iodide and kept standing for three days at 3° C. The reaction solution was evaporated to dryness under reduced pressure and the resulting residue was washed with ether and dried. The powder obtained was dissolved in a mixture of THF (10 ml) and water (10 ml), added 1.2 g of ammonium chloride and 600 mg of iron powder (100 mesh) and vigorously stirred for one hour. Insolubles were filtered off using Celite ®, the filtrate was diluted with water, washed with 1:1 mixture of ethyl acetate-ether and the water phase was concentrated to 20 ml, under reduced pressure. The concentrate was purified by column chromatography using Diaion HP-20 (1.8 cm×20 cm), the fractions eluted with 100 ml of water were discarded, before collecting the fractions eluted with 5% THF-water and concentrating them under reduced pressure The resultant concentrate was further subjected to HPLC [carrier: Nucleosil 7C$_{18}$ (10×300 mm); solvent: 5% acetonitrile-water; flow rate: 4 ml/min.]and the fractions having the retention time of 18 min. and 24 min. respectively, which gave the objective isomers A and B as pale yellow powder respectively.

Isomer A

Yield 9 mg
I. R. (KBr disc)cm$^{-1}$: 1760, 1725, 1670, 1640, 1580
U. V. $\lambda_{max}$ (H$_2$O)nm: 323
N. M. R. $\delta$(D$_2$O)ppm: 1.37 (3H; d; J=6Hz; CH$_3$), 3.22 (1H; dd; J=18, 4Hz), 3.68 (1H; dd; J=18, 7Hz), 3.94 (3H; s; ≡⊕NH$_3$), 4.01 (1H; dd; J=7, 2Hz; C$_6$-H), 4.20~4.70 (4H; m), 4.80 (HOD), 5.78 (1H; d; J=2Hz; C$_5$-H), 7.23 (1H; s; imidazolium ring-H), 8.64 (1H; s; imidazolium ring-H)
HPLC (retention time): 18 min.

Isomer B

Yield 6 mg
I. R. (KBr disc)cm$^{-1}$: 1765, 1590
U. V. $\lambda_{max}$ (H$_2$O)nm: 323
N. M. R. $\delta$(D$_2$O)ppm: 1.37 (3H; d; J=6Hz; CH$_3$), 3.12 (1H; dd; J=18, 4Hz), 3.64 (1H; dd; J=18, 7Hz), 3.94 (3H; s; ≡⊕NCH$_3$), 4.20~4.70 (4H; m), 4.80 (HOD), 5.78 (1H; d; J=2Hz; C$_5$-H), 7.24 (1H, s, imidazolium ring-H), 8.64 (1H; s; imidazolium ring-H)
HPLC (retention time): 24 min.

EXAMPLE 26

Synthesis of (5R, 6S, 8R)-6-(1-hydroxyethyl)-2-[(6,7-dihydro-1-hydroxy-5H-pyrrolo[1,2-c]imidazol-6-yl)thio]-2-penem-3-carboxylic acid

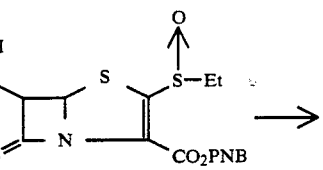

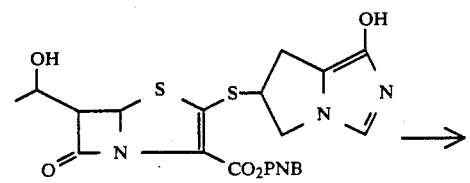

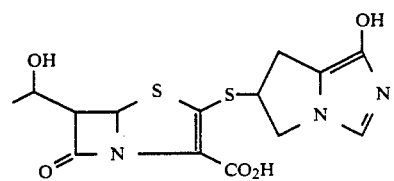

(1) Synthesis of p-nitrobenzyl (5R, 6S, 8R)-6-(1-hydroxyethyl)-2-[(6,7-dihydro-1-hydroxy-5H-pyrrolo[1,2-c]imidazol-6-yl)thio]-2-penem-3-carboxylate According to the procedures similar to those in the step (1) of the example 22, the objective compound was prepared using 170 mg of p-nitrobenzyl (5R, 6S, 8R)-2-ethylsulfinyl-6-(1-hydroxyethyl)-2-penem-3-carboxylate, 300 mg of 6,7-dihydro-1-hydroxy-6-mercapto-5H-pyrrolo [1,2-c]imidazole obtained in the step (8) of the reference example 17 and 396 mg of DBU. Yield: 195 mg.

N. M. R. δ(CDCl₃-CD₃OD)ppm: 1.35 (3H; d; J=6Hz; CH₃), 5.35 (2H; ABq; J=14Hz; OCH₂Ar), 5.72 (1H; d; J=2Hz; C₅-H), 7.64 (2H; d; J=9Hz; 2×ArH), 8.23 (2H; d; J=9Hz; 2×ArH), 8.23 (1H; s; imidazole ring-H)

(2) Synthesis of (5R, 6S, 8R)-6-(1-hydroxyethyl)-2-[(6,7-dihydro-1-hydroxy-5H-pyrrolo[1,2-c]imidazol-6-yl)thio]-2-penem-3-carboxylic acid According to the procedures similar to those disclosed in the step (2) of the example 22, the objective compound (yield: 36 mg) was obtained by utilizing 195 mg of the compound obtained in the preceeding step (1) and 300 mg of palladium-carbon.

I. R. (KBr disc)cm⁻¹: 3400, 1760, 1650, 1580
U. V. λmax (H₂O)nm: 323
N. M. R. δ(D₂O)ppm: 1.37 (3H; d; J=6Hz; CH₃), 2.60 (2H; m), 4.00~4.40 (5H; m), 4.80 (HOD), 5.78 (1H; d; J=2Hz; C₅-H), 8.32 (1H; s; imidazole ring-H)
HPLC (retention time) 13 min.
Conditions
Carrier: Nucleosil 7C₁₈ (10×300 mm)
Solvent: 1% acetonitrile-water
flow rate: 4 ml/min.

EXAMPLE 27

(1) Synthesis of p-nitrobenzyl (5R, 6S, 8R)-6-(1-hydroxyethyl)-2-[(6,7-dihydro-5H-pyrrolo[2,1-c]-1,2,4-triazol-6-yl)thio]-2-penem-3-carboxylate

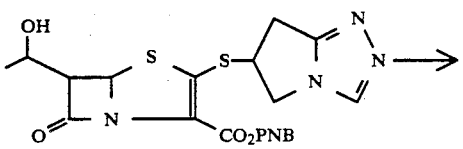

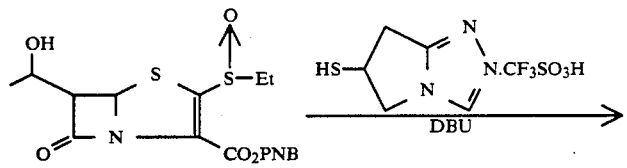

p-Nitrobenzyl (5R, 6S, 8R)-2-ethylsulfinyl-6-(1-hydroxyethyl)-penem-3-carboxylate (170 mg) was dissolved in a mixture of acetonitrile (2 ml) and THF (2 ml) and cooled to −30° C. To the cooled solution there were added a solution of 6,7-dihydro-6-mercapto-5H-pyrrolo[2,1-c]-1,2,4-triazole trifluoromethane sulfonate (250 mg) in acetonitrile (2 ml) and DBU (244 mg) and stirred for 20 minutes at that temperature. After the reaction was completed, 30 ml of ethyl acetate was added, washed with water, then with saturated NaCl aqueous solution, dried over Na₂SO₄ and concentrated under reduced pressure. The residue obtained was subjected to column chromatography using 15 g of silica gel, in which the elution was effected using methanol containing chloroform (the polarity thereof being gradually increased by changing the mixing ratio between CHCl₃ and CH₃OH from 19:1 to 4:1). The fractions containing the objective compound were collected and concentrate under reduced pressure to obtain the objective compound (yield: 147 mg) as yellowish oil.

N. M. R. δ(CDCl₃+CD₃OD)ppm: 1.36 (3H; d; J=6Hz; CH₃), 3.0~3.9 (3H; m), 4.0~4.8 (4H; m), 5.34 (2H; ABq; J=14Hz; —COOCH₂—), 5.77 (1H; d; J=2Hz; C₅-H), 7.61 and 8.21 (each 2H; each d; J=9Hz; —C₆H₄NO₂), 8.18 (1H; s; triazole ring-H)

TLC: Rf=0.3 [silica gel plate (Merck), 0.25 mm in thick; developing solvent: chloroform-methanol (4:1 v/v)]

(2) Synthesis of (5R, 6S, 8R)-6-(1-hydroxyethyl)-2-[(6,7-dihydro-5H-pyrrolo[(2,1-c]-1,2,4-triazol-6-yl)thio]-2-penem-3-carboxylic acid (isomers A and B)

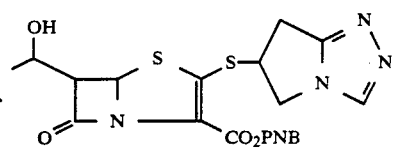

The compound (141 mg) obtained in the preceeding step (1) was dissolved in a mixture of THF (6 ml) and phosphate buffer (pH 7.0; 6 ml), added 200 mg of 10% palladium-carbon to effect catalytic reduction at room temperature for 3.5 hours under 1 atm. of hydrogen. After the catalyst was filtered off, the filtrate was diluted with water and the water phase was washed with 1:1 mixture of ether and ethyl acetate. The water phase was concentrated to 30 ml and purified by passing it through a column packed with Diaion HP-20 (1.8 cm×20 cm). 94The fractions eluted with 100 ml of water were discarded and those eluted with 5% THF-water were collected and concentrated under reduced pressure. The concentrate was further subjected to HPLC [carrier: Nucleosil 7C₁₈ (10×300 mm); solvent: 3% acetonitrile-water; flow rate: 4 ml/ min.], the fractions showing the retention time of 11 min. were collected, concentrated under reduced pressure and liophilized to obtain 30 mg of the objective compound as colorless powder.

I. R. (KBr disc)cm⁻¹: 3400, 1760, 1580
U. V. λmax (H₂O)nm 323
N. M. R. δ(D₂O)ppm: 1.36 (3H; d; J=7Hz; CH₃), 3.0~3.8 (2H; m;

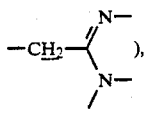

4.00 (1H; dd; J=2, 6Hz; C6-H), 4.2~4.4 (m); 4.80 (HOD), 5.77 (1H; d; J=2Hz; C5-H), 8.44 (1H; s; triazole ring-H)

The product was further purified by HPLC [carrier: ODS (20×300 mm); solvent 3% acetonitrile-water; flow rate: 10 ml/min]and collected the fractions showing the retention time of 12.3 min. and 13 min. which gave isomers A and B respectively after liophilization, as pale yellow powder.

Isomer A

N. M. R. δ(D2O)ppm: 1.36 (3H; d; J=6Hz; CH3), 3.00~3.32 (1H; m), 3.50~3.83 (1H; m), 4.00 (1H; dd; J=2, 6Hz; C6-H), 4.10~4.50 (2H; m), 4.80 (HOD), 5.77 (1H; d; J=2Hz; C5-H), 8.44 (1H; s; triazole ring-H)

Isomer B

N. M. R. δ(D2O)ppm: 1.36 (3H; d; J=6Hz; CH3), 2.96~3.22 (1H; m), 3.46~3.78 (1H; m), 4.00 (1H; dd; J=2, 6Hz; C6-H), 4.13~4.50 (2H; m), 4.80 (HOD), 5.77 (1H; d; J=2Hz; C5-H), 8.44 (1H; s; triazole ring-H)

EXAMPLE 28

Synthesis of (5R, 6S, 8R)-6-(1-hydroxyethyl)-2-[(6,7-dihydro-N-methyl-5H-pyrrolo[2,1-c]-1,2,4-triazolium-6-yl)thio]-2-penem-3-carboxylate (mixture of isomers A and B and isomers C and D)

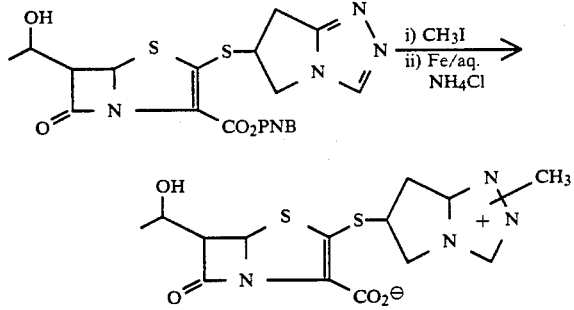

The compound (400 mg) obtained in the step (1) of the example 27 was treated according to the procedures similar to those disclosed in the example 23 and then subjected to HPLC [carrier: Nucleosil 7C18 (10×300mm); solvent: 5% acetonitrile-water; flow rate: 5 ml/min.]to isolate and purify the product. Thus, the three fractions showing the retention time of 7.8 and 8.4, 9.7 and 13.5 min. were separated which gave the objective mixed isomer A, B and isomers C. and D after liophilization as yellow powder.

Mixed Isomer A, B

Yield 35 mg
I. R. (KBr disc)cm$^{-1}$: 3400, 1770, 1640, 1580
U. V. λ$_{max}$ (H2O)nm: 323
N. M. R. δ(D2O)ppm: 1.36 (3H; d; J=6Hz; CH3), 3.3~4.0 (2H; m), 4.06 (3H; s; N-CH3), 4.80 (HOD), 5.80 (1H; d; J=2Hz; C5-H), 8.76 (1H; s; triazolium ring-H)

Isomer C

Yield 36 mg
U. V. λ$_{max}$ (H2O)nm: 323
N. M. R. δ(D2O)ppm: 1.38 (3H; d; J=6Hz; CH3), 3.25~3.56 (1H; m), 3.71~4.10 (2H; m), 4.18 (3H; s; N-CH3), 4.80 (HOD), 5.81 (1H; d; J=2Hz; C5-H)

Isomer D

Yield 38 mg
U. V. λ$_{max}$ (H2O)nm: 323
N. M. R. δ(D2O)ppm: 1.37 (3H; d; J=6Hz; CH3), 3.15~3.45 (1H; m), 3.63~4.10 (2H; m), 4.18 (3H; s; N-CH3), 4.80 (HOD) 5.81 (1H; d; J=2Hz; C5-H)

EXAMPLE 29

Synthesis of (5R, 6S, 8R)-2-[(3-amino-6,7-dihydro-5H-pyrrolo[2,1-c]-1,2,4-triazol-6-yl)thio]-6-(1-hydroxyethyl)-penem-3-carboxylic acid

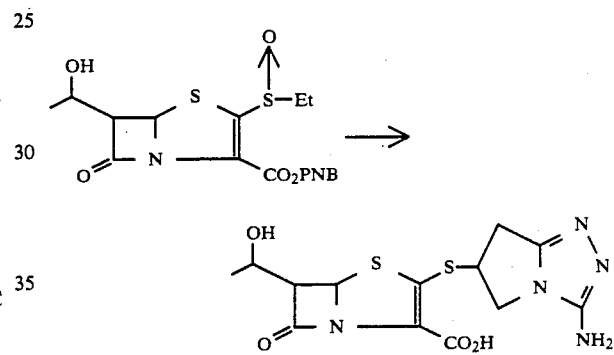

p-Nitrobenzyl (5R, 6S, 8R)-2-ethylsulfinyl-6-(1-hydroxyethyl)-penem-3-carboxylate (70 mg) and 3-amino-6,7-dihydro-6-mercapto-5H-pyrrolo[2,1-c]-1,2,4-triazole trifluoromethane sulfonate (100 mg) were dissolved in DMF (2 ml), added diisopropylethyl amine (85 mg) while cooling to −50° C. and stirred for 30 minutes at that temperature. The reaction solution was poured into ether and the supernatant liquid was removed by decantation. The precipitates were dissolved in a mixture of THF (15 ml) and phosphate buffer (pH 7.0; 15 ml), and added 10% palladium-carbon (100 mg) to carry out catalytic reduction at room temperature for five hours. After the removal of catalyst by filtration, the filtrate and the wash liquid were concentrated under reduced pressure and washed with ethyl acetate. The water phase was concentrated and the concentrate was purified by passing through a column packed with Diaion HP-20 (1.8×18 cm). At this stage, the fractions eluted by 130 ml of water were discarded and the fractions eluted with 5% THF-water were combined, concentrated and purified by HPLC [carrier: Nucleosil 7C18 (10×300 mm); solvent: 3% acetonitrile-water; flow rate: 3.65 ml/min]. After liophilization, 24 mg of the objective product was obtained as colorless powder.
I. R. (KBr disc)cm$^{-1}$: 1760, 1675
U. V. λ$_{max}$ (H2O)nm: 253, 323
N. M. R. δ(D2O)ppm: 1.36 (9/5H; d; J=6Hz; CH3), 1.40 (6/5H; d; J=6Hz; CH3), 3.1~3.5 (1H; m; pyrroline ring C7-H). 3.50~4.0 (1H; m; pyrroline ring C7-H), 4.0~5.0 (5H; m; pyrroline ring $C_5$-$H_2$, pyrroline ring $C_6$-H,
$C_6$-H and $C_8$-H), 4.80 (HOD), 5.80 (1H; d; J=1Hz; $C_5$-H)

HPLC (retention time) 23.2 and 28.8 min.

EXAMPLE 30

Synthesis of (5R, 6S, 8R)-2-[(2,3-dihydro-1H-pyrazolo[1,2-a]pyrazolium-2-yl)thio]-6-(1-hydroxyethyl)-2-penem-3-carboxylate

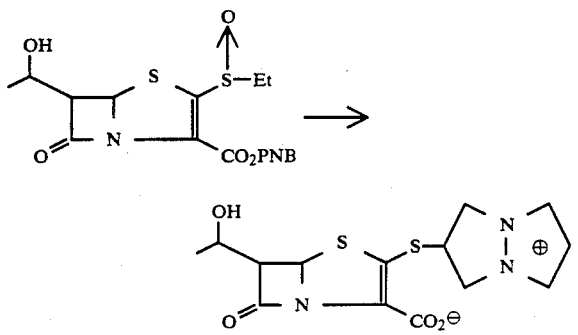

According to the procedures similar to those in the example 19 except for using 2,3-dihydro-2-mercapto-1H-pyrazolo[1,2-a]pyrazolium.trifluoromethane sulfonate, the objective compound was prepared as pale yellow powder.

I. R. (KBr disc)cm$^{-1}$: 1775, 1595
U. V. $\lambda_{max}$ ($H_2O$)nm: 250, 323
N. M. R. $\delta$($D_2O$)ppm: 1.36 (3H; d; J=6Hz; $CH_3$), 4.03 (1H; dd; J=2, 6Hz; $CH_3$), 4.15~4.43 (1H; m; $C_8$-H), 5.80 (1H; d; J=2Hz; $C_5$-H), 6.97 (1H; t; J=3Hz; pyrazolium-H at 6-position), 8.28 (2H; d; J=3Hz; pyrazolium-H at 5- and 7-positions)

HPLC (retention time: 13 min.
Conditions
Carrier: Nucleosil 7$C_{18}$ (10×300 mm)
Solvent: 3% acetonitrile-water
Flow rate: 5 ml/min.

EXAMPLE 31

Synthesis of (5R, 6S, 8R)-6-(1-hydroxyethyl)-2-[(4-methylpyrrolizidinium-1-yl)thio]-2-penem-3-carboxylate (isomers A and B)

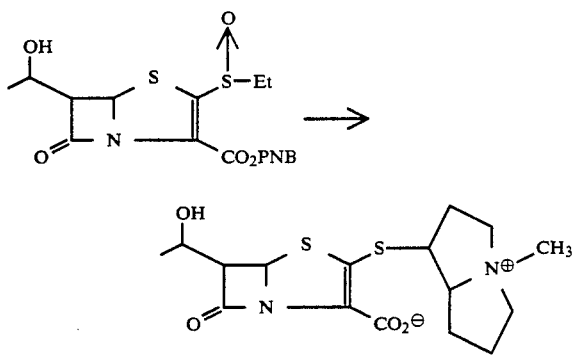

p-Nitrobenzyl (5R, 6S, 8R)-2-ethylsulfinyl-6-(1-hydroxyethyl)-2-penem-3-carboxylate (150 mg) and 1-mercapto-4-methylpyrrolizidinium.trifluoromethane sulfonate (215 mg) were dissolved in 4 ml of DMF, added 130 mg of diisopropylethylamine while stirring and cooling at $-40°$ C. and stirred for one hour under argon atmosphere. To the reaction mixture was added ether and the ether phase was removed. The residue was dissolved in a mixture of THF (20 ml) and phosphate buffer (pH 7.0; 20 ml), added 200 mg of platinum oxide and subjected to reduction under 4 atms. of hydrogen for one hour. The water phase was concentrated under reduced pressure, the concentrate was subjected to 7 column chromatography using Diaion HP-20 (20×300 mm), the fractions eluted with 5% THF-water were collected, concentrated under reduced pressure and purified by HPLC [carrier: Nucleosil 7$C_{18}$ (10×300 mm); solvent: 5% acetonitrile-water; flow rate: 5 ml/min.]. Thus, the objective compound was obtained as pale yellow powder after liophilization.

Isomer A

Yield 15 mg
I. R. (KBr disc)cm$^{-1}$: 1765, 1590
U. V. $\lambda_{max}$ ($H_2O$)nm: 258, 323
N. M. R. $\delta$($D_2O$)ppm: 1.37 (3H; d; J=6Hz; $CH_3$), 1.90~2.90 (6H; m), 3.29 (3H; s; $\equiv\oplus NCH_3$), 3.40~4.60 (8H; m), 4.80 (HOD), 5.80 (1H; d; J=2Hz; $C_5$-H)

HPLC (retention time): 12 min.

Isomer B

Yield 22 mg
I. R. (KBr disc)cm$^{-1}$: 1760, 1590
U. V. $\lambda_{max}$ ($H_2O$)nm: 258, 324
N. M. R. $\delta$($D_2O$)ppm: 1.37 (3H; d; J=6Hz; $CH_3$), 1.90~3.10 (6H; m), 3.32 (3H; s; $\equiv\oplus NCH_3$), 3.50~4.50 (8H; m), 4.80 (HOD), 5.80 (1H; d; J=2Hz; $C_5$-H)

HPLC (retention time): 17.5 min.

EXAMPLE 32

Synthesis of (5R, 6S, 8R)-2-[(4-(2-fluoroethyl)pyrrolizidinium-1-yl)thio]-6-(1-hydroxyethyl)-2-penem-3-carboxylate (isomers A and B)

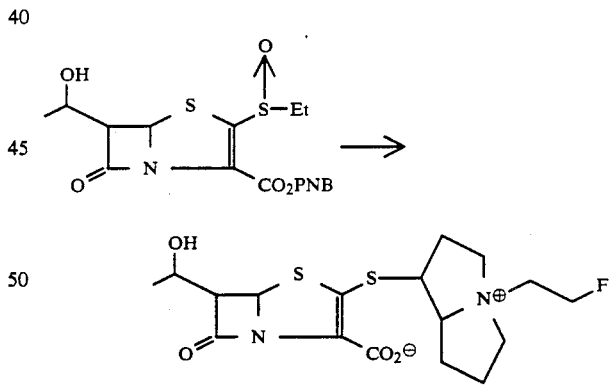

The procedures similar to the example 31 were repeated using 4-(2-fluoroethyl)-1-mercapto-pyrrolizidinium trifluoromethane sulfonate and obtained the objective product as pale yellow powder.

Isomer A

I. R. (KBr disc)cm$^{-1}$: 1770, 1595
U. V. $\lambda_{max}$ ($H_2O$)nm: 255, 323
N. M. R. $\delta$($D_2O$)ppm: 1.36 (3H; d; J=6Hz; $CH_3$), 1.90~2.80 (6H; m), 3.20~4.50 (10H; m), 4.80 (HOD), 5.20~5.40 (1H; m), 5.80 (1H; d; J=2Hz; $C_5$-H)

HPLC (retention time): 10.5 min.
Conditions

Carrier: Nucleosil 7C$_{18}$ (10×300 mm)
Solvent: 7% acetonitrile-water
Flow rate: 5 ml/min.

Isomer B

I. R. (KBr disc)cm$^{-1}$: 1770, 1590
U. V. $\lambda_{max}$ (H$_2$O)nm: 255, 323
N. M. R. δ(D$_2$O)ppm: 1.36 (3H; d; J=6Hz; CH$_3$), 1.80~3.00 (6H; m), 3.50~4.50 (10H; m), 4.80 (HOD), 5.20~5.40 (1H; m), 5.80 (1H; d; J=2Hz; C$_5$-H)
HPLC (retention time): 12.5 min.

EXAMPLE 33

Synthesis of (5R, 6S, 8R)-6-(1-hydroxyethyl)-2-[(4-methylpyrrolizidinium-2-yl)thio]-2-penem-3-carboxylate (isomers A and B)

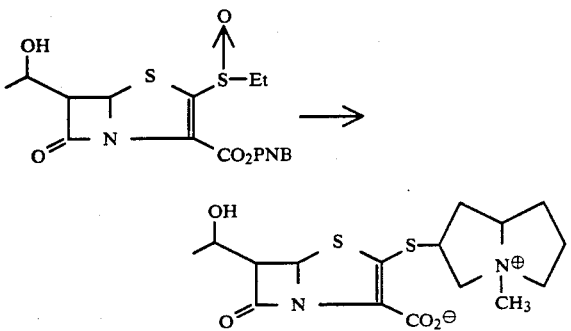

According to the procedures similar to the example 31 except that 2-mercapto-4-methylpyrrolizidinium trifluoromethane sulfonate was used, the objective isomers were obtained as pale yellow powder.

Isomer A

I. R. (KBr disc)cm$^{-1}$: 1765, 1590
U. V. $\lambda_{max}$ (H$_2$O)nm: 250, 322
N. M. R. δ(D$_2$O)ppm: 1.37 (3H; d; J TM 6Hz; CH$_3$), 1.80~2.70 (6H; m), 3.30 (3H; s; ≡⊕NCH$_3$), 3.55~3.80 (3H; m), 3.90~4.45 (5H; m), 4.80 (HOD), 5.78 (1H; d; J=2Hz; C$_5$-H)
HPLC (retention time): 11.5 min.
Conditions
Carrier: Nucleosil 7C$_{18}$ (10×300 mm)
Solvent: 5% acetonitrile-water
Flow rate: 5 ml/min.

Isomer B

U. V. $\lambda_{max}$ (H$_2$O)nm: 250, 323
N. M. R. δ(D$_2$O)ppm: 1.36 (3H; d; J=6Hz; CH$_3$), 1.80~2.60 (6H; m), 2.70~3.10 (1H; m), 3.24 (3H; s; ≡⊕NCH$_3$), 3.40~4.40 (7H; m), 4.80 (HOD), 5.76 (1H; d; J=2Hz; C$_5$-H)
HPLC (retention time): 15 min.

EXAMPLE 33

Synthesis of [5R,6S,8R]-2-[[6,7-dihydro-2-[N-methylcarbamoylmethyl]-5H-pyrrolo[1,2-C]imidazolium-7-yl]thio]-6-[1-hydroxyethyl]-2-penem-3-carboxylate (isomer A and isomer B)

The compound (171 mg) obtained in Example 1-(1) was dissolved in 15 ml of anhydrous acetone and 1.06 g of N-methylbromoacetamide was added thereto at the room temperature. The mixture was stirred at room temperature for 40 hours and after addition of 0.53 g of N-methylbromoacetamide, the resulting mixture was stirred for additional 22 hours. The reaction mixture was concentrated and the residue was washed with diethylether two times and dried to obtain 298 mg of yellow gummy substance. This was dissolved in 25 ml of 50% water-tetrahydrofuran and 3.40 g of ammonium chloride was added thereto. 1.70 g of iron powder( 100 mesh) was added to the mixture while stirring vigorously under room temperature and the resulting mixture was stirred for 10 minutes at room temperature and additional 90 minutes under ice-cooling. The unsoluble substance was removed by filtration using celite. The filtrate was concentrated to about 5 ml under reduced pressure and purified by column chromatography using 35 ml of Diaion HP-20. After removing the fraction flowed out with 150 ml of water, the fraction eluting with 100 ml of 5% THF-water was collected. This was concentrated to about 5 ml under reduced pressure and purified by HPLC(solvent:7% acetonitrile-water, flow rate: 3.65 ml/minute). Fractions corresponded to the retention time of 16 minutes and 21 minutes were collected and each fraction was concentrated under reduced pressure and lyophilized to obtain 33 mg of the object isomer A and 33 mg of the object isomer B, respectively.

Isomer A

IR(KBr disc)cm$^{-1}$: 3370,1765,1680,1590,1370,1290
UV $\lambda_{max}$ (H$_2$O)nm: 248(sh),324
NMR δ(D$_2$O)ppm: 1.27 (3H, d, J=6.3Hz, —CH$_3$), 2.5 3.0 (1H, m), 2.76 (3H, s, —NH—CH$_3$), 3.0~3.6 (1H, m), 3.95 (1H, dd, J=1.3Hz, 5.9Hz, C$_6$-H), 4.23 (1H, t, J=5.9Hz C$_8$-H), 4.3~4.6 (2H, m) 4.74 (HOD), 4.9~5.1 (1H, m), 4.99 (2H, s, —CH$_2$—CO—), 5.67 (1H, d, J=1.3Hz, C$_5$-H), 7.42 (1H, s) 8.74 (1H, s)

Isomer B

IR(KBr disc)cm$^{-1}$: 3370,1775,1685,1595,1370,1295
UV $\lambda_{max}$(H$_2$O)nm 258(sh.),325
NMR δ(D$_2$O)ppm: 1.27 (3H, d, J=6.3Hz, —CH$_3$), 2.4~2.9 (1H, m) 2,76 (3H, s, —NHCH$_3$), 2.9~3.4 (1H, m) 3.95 (1H, dd, J=1.5Hz, 6.1Hz), 4.27 (1H, t, J=6.1Hz, C$_8$-H), 4.3~4.6 (2H, m) 4.74 (HOD), 4.9~5.1 (1H, m), 5.00 (2H, s, —CH$_2$—CO—) 5.68 (1H, d, J=1.5Hz, C$_5$-H), 7.44 (1H, s), 8.75 (1H, s)

EXAMPLE 34

Synthesis of (5R,6S,8R)-2-((6,7-dihydro-2-(N-ethylcarbamoylmethyl)-5H-pyrrolo(1,2-C)imidazolium-7-yl)thio)-6-(1-hydroxyethyl)-2-penem-3-carboxylate (isomer A and isomer B)

According to similar procedures to Example 33 using N-ethylbromoacetamide, the object isomer A and isomer B were obtained in a yield of 37 mg and 38 mg, respectively. Conditions of HPLC were the same as in EXAMPLE 33, and retention time for the isomer A was 25 minutes and 31 minutes for the isomer B.

Isomer A

IR(KBr disc)cm$^{-1}$: 3380,2980,1775,1680,1595,1450,1370, 1290
UV $\lambda_{max}$(H$_2$O)nm: 250(sh),324
NMR δ(D$_2$O)ppm: 1.10 (3H, t, J=7.3Hz, —CH$_2$—CH$_3$), 1.28 (3H, d, J=6.3Hz, —CH$_3$), 2.5~3.0 (1H, m), 3.24 (2H, q, J=7.3Hz, CH$_2$—CH$_3$), 3.0~3.4 (1H, m), 3.95 (1H, dd, J=1.3Hz, 5.9Hz, C$_6$-H), 4.23 (1H, t, J=5.9Hz, C$_8$-H), 4.3~4.6 (2H, m), 4.74 (HOD), 4.9~5.1 (1H, m), 4.98 (2H, s, —CH$_2$—CO—), 5.69 (1H, d, J=1.3Hz, C$_5$-H), 7.42 (1H, s) 8.74 (1H, s)

IR(KBr disc)cm$^{-1}$: 3400,2970,1775,1675,1590,1440,1365, 1290

UV λ$_{max}$(H 0)nm 258(sh.),324

NMR δ(D$_2$O)ppm: 1.12 (3H, t, J=7.2Hz, —CH$_2$CH$_3$), 1.29 (3H, d, J=6.4Hz, —CH$_3$), 2.4~2.9 (1H, m), 3.25 (2H, q, J=7.2Hz, —CH$_2$—CH$_3$), 2.9~3.4 (1H, m), 3.93 (1H, dd, J=1.3Hz, 5.9Hz, C$_6$-H), 4.24 (1H, t, J=5.9Hz, C$_8$-H), 4.3~4.6 (2H, m), 4.74 (HOD), 4.9~5.1 (1H, m), 4.99 (2H, s, —CH$_2$—CO—), 5.69 (1H, d, J=1.3Hz, C$_5$-H), 7.45 (1H, s), 8.74 (1H, s)

EXAMPLE 35

Synthesis of (5R,6S,8R}-2-((6,7-dihydro-2-(N-dimethylcarbamoyl-methyl)-5H-pyrrolo(1,2-C)imidazolium-7-yl)thio)-6-(1-hydroxyethyl)-2-penem-3-carboxylate (isomer A and isomer B)

According to similar procedures to Example 33, the object isomer A and isomer B were obtained in a yield of 17 mg and 40 mg, respectively. Conditions of HPLC were the same as in Example 33, and retention time for the isomer A was 19.5 minutes and 22.5 minutes for the isomer B.

Isomer A

IR(KBr disc)cm$^{-1}$: 3400,3130,2970,1775,1660,1585,1360, 1280

UV λ$_{max}$(H 0)nm: 247(sh),325

NMR δ(D$_2$O)ppm: 1.34 (3H, d, J=6.4Hz, —CH$_3$), 2.5~3.5 (2H, m), 3.01 (3H, s,

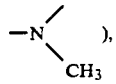), 3.13 (3H, s,

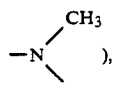), 4.00 (1H, d, C$_6$-H), 4.1~4.6 (3H, m), 4.74 (HOD), 4.9~5.1 (1H, m), 5.31 (2H, s, CH$_2$CO—), 5.74 (1H, br, s, C$_5$-H), 7.42 (1H, s), 8.73 (1H, s)

Isomer B

IR(KBr disc)cm$^{-1}$: 3400,3130,2970,1775,1660,1590,1360, 1285

UV λ$_{max}$(H$_2$O)nm 256(sh.),325

NMR δ(D$_2$O)ppm: 1.32 (3H, d, J=6.1Hz, —CH$_3$), 2.5~3.5 (2H, m), 3.01 (3H, s,

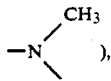), 3.13 (3H, s,

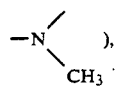), 3.97 (1H, d, —CH$_6$H), 4.1~4.6 (3H, m), 4.74 (HOD), 4.9~5.1 (1H, m), 5.30 (2H, s, —CH$_2$—CO—), 5.73 (1H, br, s, C$_5$-H), 7.43 (1H, s)

EXAMPLE 136

Synthesis of (5R, 6S, 8R)-2-((2-(2-carbamoylethyl)-6,7-dihydro-5H-pyrrolo(1,2-C) imidazolium-7-yl)thio)-6-(1-hydroxyethyl)-2-penem-3-carboxylate (isomer A and isomer B)

According to similar procedures to Example 33, the object isomer A and isomer B were obtained in a yield of 16 mg and 23 mg, respectively. Conditions of HPLC were the same as in Example 33, and retention time for the isomer A was 12 minutes and 17 minutes for the isomer B.

Isomer A

IR(KBr disc) cm$^{-1}$: 3350,1765,1670,1575,1360,1285

UV λ$_{max}$(H$_2$O)nm: 214, 250(sh), 325

NMR δ(D$_2$O) ppm: 1.34 (3H, d, J=6.4Hz, —CH$_3$), 2.6~3.6 (2H, m), 2,92 (2H, t, J=6.4Hz, —CH$_2$—CO—), 4.00 (1H, dd, J=1.3Hz, 5.9Hz, C$_6$H), 4.1~4.7 (5H, m), 4.74 (HOD), 4.95~5.1 (1H, m), 5.73 (1H, d, J=1.3Hz, C$_5$H), 7.49 (1H, s), 8.74 (1H, s)

Isomer B

IR(KBr disc) cm$^{-1}$: 3370,1775,1675,1585,1360,1290

UV λ$_{max}$(H$_2$O)nm: 215, 260(sh), 324

NMR δ(D$_2$O) ppm: 1.33 (3H, d, J=6.4Hz, —CH$_3$), 2.5~3.5 (2H, m), 2.90 (2H, t, J=6.2Hz, —CH$_2$—CO), 3.98 (1H, d, J=5.9Hz, —C6H), 4.1~4.7 (5H, m), 4.74 (HOD), 4.9~5.1 (1H, m), 5.76 (1H, br.s, C$_5$-H), 7.53 (1H, s), 8.74 (1H, s)

EXAMPLE 37

Synthesis of [5R,6S,8R]-2-[[6,7-dihydro-2-phenacyl-5H-pyrrolo[1,2-C]imidazolium-7-yl)thio)-6-(1-hydroxyethyl)-2-penem-3-carboxylate (mixture of isomer A and isomer B).

According to similar procedures to Example 33, the mixture of the isomer A and isomer B was obtained in a yield of 54 mg.

Conditions of HPLC
Column : Nucleosil 7C$_{18}$ (10 mm×300 mm)
Solvent :20% acetonitrile-water
Flow rate : 3.65 ml/min.
Retention time : 14 minutes
IR(KBr disc)cm$^{-1}$: 3400,1770,1690,1590,1450,1360
UV λ$_{max}$(H$_2$O)nm: 250(sh), 324

NMR δ(D$_2$O) ppm: 1.28 (3H, d, J=6.6Hz, —CH$_3$), 2.3~3.0 (1H, m), 3.0~3.5 (1H, m), 3.93 (1H, d, J=6.5Hz, C$_6$-H), 4.23 (1H, t, J=6.5Hz, C$_8$H), 4.3~4.7 (2H, m), 4.74 (HOD), 5.0~5.2 (1H, m), 5.68 (1H, s, C$_5$-H), 6.00 (2H, s, —CH$_2$—CO—), 7.48 (1H, s), 7.5~7.9 (3H, m), 8.10 (2H, d, J=7.0Hz), 8,79 (1H, s)

EXAMPLE 38

Synthesis of (5R,6S,8R)-2-((6,7-dihydro-2-(1-methyltetrazol-5-yl)thiomethyl)-5H-pyrrolo(1,2-C)imidazolium-7-yl)thio)-6-(1-hydroxyethyl)-2-penem-3-carboxylate (isomer A and isomer B)

According to similar procedures to Example 33, the object isomer A and isomer B were obtained in a yield of 22 mg and 25 mg, respectively.

Condition of HPLC
Column : Nucleosil 7C$_{18}$
Solvent : actnitril-water(1:9)
Flow rate : 5 ml/min.
Retention time : 14 minutes(isomer A), Isomer A 17 minutes (isomer B)

UV $\lambda_{max}$(H 0)nm: 325

NMR $\delta$(D$_2$O) ppm: 1.37 (3H, d, J=6Hz, —CH$_3$), 2.70~3.00 (1H, m), 3.10~3.60 (1H, m), 4.02 (1H, dd, J=2Hz, 6Hz, C$_6$-H), 4.10 (3H, s, J=7.3Hz, CH$_3$), 4.20~4.70 (3H, m), 4.80 (HOD), 5.76 (1H, d, J=2Hz, C$_5$-H), 6.03 (2H, s, —C$_2$—S), 7.72 (1H, s), 9.08 (1H, s)

Isomer B

UV $\lambda_{max}$(H$_2$O)nm 258(sh.), 325

NMR $\delta$(D$_2$O) ppm: 1.38 (3H, d, J=6Hz, CH$_3$), 2.56~2.90 (1H, m), 3.00~3.50 (1H, m), 4.00 (1H, dd, J=2Hz, 6Hz), 4.08 (3H, s, CH$_3$), 4.20~4.70 (3H, m), 4.80 (HOD), 5.76 (1H, d, J=2Hz), 6.04 (2H, s, —CH$_2$—S—), 7.77 (1H, s), 9.08 (1H, s)

REFERENCE EXAMPLE 12

Synthesis of 2,3-dihydro-1-mercapto-1H-indolizinium trifluoromethane sulfonate

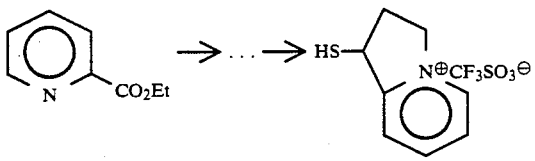

(1) Ethyl picolinoyl acetate

Sodium hydride was suspended in 200 ml of DMF and a mixed solution of ethyl picolinate (20 g) and ethyl acetate (17.5 g) dissolved in 150 ml of DMF a the bath-temperature of 50° C. was added dropwise over about 30 minutes. The reaction solution was ice cooled after stirring for 30 minutes at the temperature of 50° C. and acetic acid (13.0 g) was added dropwise.

The reaction solution was diluted with ethyl acetate, washed with water and dried over MgSO$_4$, then the solvent was distilled off in vacuo. The objective compound was obtained (yield: 21.2 g).

N. M. R. $\delta$(CDCl$_3$)ppm: 1.23 (3H; t; J=7Hz), 4.16 (2H; s), 4.16 (2H; q; J=7Hz), 7.40 (1H; ddd; J=1, 7, 7Hz), 7.77 (1H; dd; J=1, 7Hz), 7.95 (1H; ddd; J=1, 7, 7Hz), 8.58 (1H; dd; J=1, 7Hz)

(2) Ethyl 3-hydroxy-3-(2-pyridyl) propionate

The compound (21.0 g) obtained in the step (1) was dissolved in 300 ml of ethanol and sodium borohydride (2.1 g) was added under ice cooling and stirring, and further stirred for 30 minutes at that temperature. The reaction solution was neutralized by 0.5N hydrochloric acid under ice cooling and the solvent was distilled off in vacuo. The residue was distributed between water and ethyl acetate, the ethyl acetate phase was washed with water, dried over MgSO$_4$ and the solvent was distilled off in vacuo. The residue was purified by column chromatography using 150 g of silica gel (eluent: benzene/ethyl acetate (1:1 v/v)) and thus the objective compound was obtained (yield: 14.6 g).

N. M. R. $\delta$(CDCl$_3$)ppm: 1.14 (3H; t; J=7Hz), 2.61 (1H; dd; J=8, 17Hz), 2.80 (1H; dd; J=5, 17Hz), 4.04 (2H; q; J=7Hz), 4.30 (1H; m), 5.05 (1H; m), 7.04 (1H; dt; J=1, 7Hz), 7.27 (1H; dd; J=1, 7Hz), 7.55 (1H; dt; J=1, 7Hz), 8.36 (1H; dd; J=1, 7Hz)

(3) Ethyl 3-benzoylthio-3-(2-pyridyl)proprionate

Triphenylphosphine (37.6 g) was dissolved in 400 ml of THF, diethyl azodicarboxylate (25.0 g) was added under ice cooling and continuously stirred for 30 minutes at that temperature. A mixed solution consisting of a solution of the compound (14.0 g) obtained in the step (2) in 100 ml of THF and thiobenzoic acid (16.0 g) was added to the reaction solution and stirred for 2 hours at that temperature. The reaction solution was evaporated to dryness in vacuo and the residue was distributed between ethyl acetate and an aqueous solution of 5% sodium bicarbonate. The ethyl acetate layer was washed with water, dried over MgSO$_4$ and then the solvent was distilled off in vacuo. The precipitated crystals were washed with isopropyl ether. The residue was purified by column chromatography using a column packed with 500 g of silica gel [eluent: benzene/ethyl acetate (10:1 v/v)]. The resulting residue was purified once more by column chromatography using a column packed with 300 g of silica gel [eluent: benzene/ethyl acetat (10:1 v/v)] and the objective compound was obtained (yield: 15.2 g).

N. M. R. $\delta$(CDCl$_3$)ppm: 1.17 (3H; t; J=7Hz), 3.12 (1H; dd; J=7, 15Hz), 3.44 (1H; dd; J=8, 15Hz), 4.08 (2H; q; J=7Hz), 5.38 (1H; dd; J=8, 15Hz), 7.1~7.8 (6H; m), 7.8~8.0 (2H; m), 8.56 (1H; dd; J=1, 7Hz)

(4) Ethyl 3-p-methoxybenzylthio-3-(2-pyridyl)propionate

The compound (5.55 g) obtained in the step (3) was dissolved in 80 ml of methanol, sodium methoxide (0.95 g) was added under ice cooling and stirred for 2.5 hours at that temperature. Acetic acid (1.06 g) was added to the reaction solution and the solution was evaporated to dryness in vacuo.

The residue was distributed between 5% aqueous solution of sodium bicarbonate and ethyl acetate, the ethyl acetate phase was dried over MgSO$_4$ and then the solvent was distilled off in vacuo. The resultant oily material (5.02 g) was dissolved in 150 ml of benzene, p-methoxybenzyl chloride (2.76 g) and DBU (2.68 g) were added thereto and stirred for one hour at room temperature. The reaction solution was washed with water and dried over MgSO$_4$, then the solvent was distilled off in vacuo. The residue was purified by column chromatography using a column packed with 150 g of silica gel [eluent: benzene/ethyl acetate (10:1 v/v)] and the objective compound was thus obtained (yield: 3.26 g).

N M. R. $\delta$(CDCl$_3$)ppm: 1.12 (3H; t; J=7Hz), 2.88 (1H; dd; J=7, 16Hz), 3.13 (1H; dd; J=9, 16Hz), 3.60 (2H; s), 3.76 (3H; s), 4.03 (2H; q; J=7Hz), 4.28 (1H; dd; J=7, 9Hz), 6.76 (2H; d; J=9Hz), 7.13 (2H; d; J=9Hz), 7.0~7.4 (2H; m), 7.57 (1H; dt, J=2, 8Hz), 8.48 (1H; dd; J=2, 7Hz)

(5) 3-p-Methoxybenzylthio-3-(2-pyridyl)propanol

Lithium alumium hydride (1.07 g) was suspended in 150 ml of ether, a solution of the compound (9.34 g) obtained in the step (4) in 70 ml of ether in the argon atmosphere was added dropwise thereto and refluxed under heating for 1.5 hours. An aqueous solution of 20% ammonium chloride (50 ml) was carefully added to the reaction solution under ice cooling and filtered with Cerite ®. After the ether phase was washed with water and dried over MgSO₄, the solvent was distilled off in vacuo. The residue was purified by column chromatography using 70 g of silica gel (eluent: ethyl acetate) and the objective compound was obtained (yield: 7.36 g).

N. M. R. δ(CDCl₃)ppm: 2.0~2.3 (2H; m), 3.56 (2H; s), 3.5~3.8 (2H; m), 3.78 (3H; s), 4.08 (1H; t; J=7Hz), 6.80 (2H; d; J=9Hz); 7.15 (2H; d; J=9Hz), 7.1~7.5 (2H; m); 7.68 (1H; dt; J=2, 8Hz), 8.54 (1H; dd; J=2, 7Hz)

(6) 2,3-Dihydro-1-(p-methoxybenzylthio)-1H-indolizinium p-toluene sulfonate:

The compound (7.86 g) obtained in the step (5) was dissolved in 50 ml of pyridine, p-toluenesulfonyl chloride (7.10 g) was added thereto and stirred for 4.5 hours under ice cooling. 100 ml of water was added to the reaction solution, the solution was adjusted to pH=9.2 with an aqueous solution of 1N sodium hydroxide and continuously extracted with ether to remove pyridine. The water phase was washed with benzene and ethyl acetate and pH thereof was adjusted to 1.8 by the addition of concentrated hydrochloric acid and evaporated to dryness in vacuo. Ethanol was added to the residue, the insoluble materials were filtered off. After the filtrate was decolored with active carbon, the filtrate was concentrated and poured into ether. The supernatant liquid was removed and the precipitates were dried so that the objective compound was obtained (yield: 9.56 g).

N. M. R. δ(DMSO-d₆)ppm: 2.26 (3H; s), 2.2~2.6 (1H; m), 2.6~3.1 (1H; m), 3.70 (2H; s), 3.90 (3H; s), 3.9 (1H; m), 4.83 (2H; m), 6.82 (2H; d; J=9Hz), 7.06 (2H; d; J=9Hz), 7.23 (2H; d; J=9Hz), 7.46 (2H; d; J=9Hz), 7.8~8.1 (2H; m), 8.41 (1H; dt; J=1,8Hz), 8.91 (1H; dd; J=1, 7Hz)

(7) 2,3-Dihydro-1-mercapto-1H-indolizinium trifluoromethane sulfonate

The compound (8.29 g) obtained in the step (6) and anisole (10.14 g) were dissolved in 50 ml of trifluoroacetic acid, trifluoromethane sulfonic acid (4.55 g) was added with ice cooling and stirred for 30 minutes at the same temperature and then for 1.5 hours at room temperature. The reaction solution was evaporated to dryness in vacuo, the residue was washed with hexane, isopropyl ether and ether, respectively. The residue was dissolved in methanol and poured into ether with stirring and the supernatant liquid was removed. The precipitates were dried and the objective compound was thus obtained (yield: 4.20 g).

N. M. R. δ(DMSO-d₆)ppm: 2.1~2.5 (1H; m), 2.6~3.2 (1H; m), 4.5~5.1 (3H; m), 7.9~8.2 (2H; m), 8.40 (1H; dt; J=1, 8Hz), 8.91 (1H; dd; J=1, 7Hz)

REFERENCE EXAMPLE 13

Synthesis of 2,3-dihydro-2-mercapto-1H-indolizinium trifluoromethane sulfonate

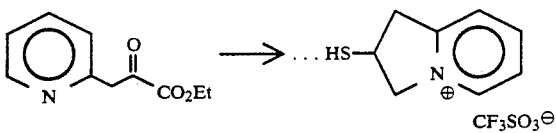

(1) Ethyl 2-hydroxy-3-(2-pyridyl) propionate

The objective compound was obtained by reacting 4.31 g of ethyl 2-pyridyl pyruvate (synthesized by the method disclosed in Chem. Pharm. Bull., 1972, 20, 1628) and subjecting the product to post-treatment according to the procedures similar to those disclosed in the step (2) of the reference example 12 (yield: 3.84 g).

N. M. R. δ(CDCl₃)ppm: 1.22 (3H; t; J=7Hz), 3.18 (1H; dd; J=7, 14Hz), 3.25 (1H; dd; J=4, 14Hz), 4.17 (2H; q; J=7Hz), 4.60 (1H; dd; J=4, 7Hz), 4.87 (1H; brs), 7.0~7.2 (2H; m), 7.56 (1H; dt; J=2, 7, 7Hz), 8.41 (1H; dd; J=1, 6Hz)

(2) Ethyl 2-benzoylthio-3-(2-pyridyl)propionate

The objective compound was obtained by reacting the compound (3.96 g) obtained in the step (1) and subjecting the product to post-treatment according to the procedures similar to those described in the step (3) of the reference example 12 (yield: 5.92 g).

N. M. R. δ(CDCl₃)ppm: 1.17 (3H; t; J=7Hz), 3.39 (1H; dd; J=7, 15Hz), 3.50 (1H; dd; J=7, 15Hz), 4.15 (2H; q; J=7Hz), 4.88 (1H; t; J=7Hz), 7.0~7.6 (6H; m), 7.86 (2H; m), 8.46 (1H; dd; J=1, 6Hz)

(3) Ethyl 2-p-methoxybenzylthio-3-(2-pyridyl)propionate

The objective compound was obtained by reacting the compound (5.90 g obtained in the step (2) and subjecting the product to post-treatment according to the method similar to that disclosed in the step (4) of the reference example 12 (yield: 4.76 g).

N. M. R. δ(CDCl₂)ppm: 1.21 (3H; t; J=7Hz), 3.10 (1H; dd; J=7, 15Hz), 3.27 (1H; dd; J=8, 15Hz), 3.75 (3H; s), 3.77 (2H; s), 3.7~3.9 (1H; m), 4.12 (2H; q; J=7Hz), 6.76 (2H; d; J=9Hz), 6.9~7.3 (4H; m), 7.50 (1H; dt; J=2, 8Hz), 8.40 (1H; dd; J=1, 6Hz)

(4) 2-p-Methoxybenzylthio-3-(2-pyridyl)propanol

The objective compound was obtained by reacting the compound (994mg) obtained in the step (3) and subjecting the product to post-treatment according to the method similar to that described in the step (5) of the reference example 12 (yield: 694mg).

N. M. R. δ(CDCl₃)ppm: 3.0~3.5 (2H; m), 3.5~4.3 (3H; m), 3.64 (2H; s), 3.76 (3H; s), 6.76 (2H; d; J=9Hz), 7.0~7.3 (2H; m), 7.12 (2H; d; J=9Hz), 7.54 (1H; dt; J=2, 7Hz), 8.40 (1H; dd; J=2, 7Hz)

(5) 2,3-Dihydro-2-(p-methoxybenzylthio)-1H-indolizinium chloride

The compound (0.8 g) obtained in the step (4) was dissolved in 40 ml of carbon tetrachloride, triphenylphosphine (1.45 g) was added thereto and refluxed under heating for 20 hours. After cooling, the supernatant liquid was removed by decantation, the black-blue oil separated was distributed between water and ethyl acetate. After the water phase was washed with chloroform five times and decolored with active carbon, it was evaporated to dryness in vacuo and the objective compound was thus obtained (yield: 0.53 g).

N. M. R. δ(DMSO-d6)ppm: 3.2~3.7 (2H; m), 3.77 (3H; s), 3.97 (2H; s), 3.7~4.0 (1H; m), 4.83 (1H; dd; J=5, 13Hz), 5.10 (1H; dd; J=7, 13Hz), 6.92 (2H; d; J=9Hz), 7.32 (2H; d; J=9Hz), 7.8~8.2 (2H; m), 8.54 (1H; dt; J=1, 8Hz), 9.00 (1H; dd; J=1, 7Hz)

(6) 2,3-Dihydro-2-mercapto-1H-indolizinium trifluoromethane sulfonate

The objective compound was obtained by reacting the compound (535mg) obtained in the step (5) and subjecting the product to post-treatment according to the method similar to that disclosed in the step (7) of the reference example 12 (yield: 520mg).

N. M. R. δ(D2O)ppm: 3.2~4.4 (3H; m), 4.7~5.0 (1H; m), 5.1~5.4 (1H; m), 7.7~8.1 (2H; m), 8.52 (1H; dt; J=2, 8Hz), 8.84 (1H; dd; J=2, 8Hz)

REFERENCE EXAMPLE 14

Synthesis of 6,7-dihydro-7-mercapto-5H-pyrrolo [1,2-a]imidazole trifluoromethane sulfonate

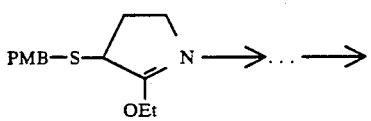

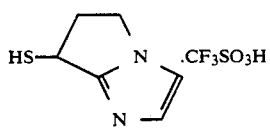

(1) 6,7-Dihydro-7-p-methoxybenzylthio-5H-pyrrolo(1,2-a)-imidazole

2-Ethoxy-3-p-ethoxybenzylthio-1-pyrroline (531mg) (synthesized according to the method disclosed in Japanese Patent Laid-Open No. 56987/1985), aminoacetaldehyde dimethylacetal (315mg) and acetic acid (180mg) were dissolved in 30 ml of ethanol and refluxed under heating for one hour. The reaction solution was evaporated to dryness in vacuo, the residue was distributed between benzene and 40 ml of water containing 4 ml of 1N sodium hydroxide aqueous solution, the benzene phase was washed with water and dried over MgSO4 and thereafter the solvent was distilled off in vacuo to obtain 700mg of colorless and transparent material. The oily material was dissolved in 30 ml of benzene, 1.14 g of p-toluenesulfonic acid (hydrate) was added thereto and refluxed under heating for one hour. The reaction solution was cooled, washed with 5% aqueous solution of sodium bicarbonate and water and dried, then the solvent was distilled off. The residue was purified by column chromatography using a column packed with 20 g of silica gel (eluent: Chloroform/methanol (19:1 v/v)) to obtain the objective compound as a colorless and transparent oil. The compound was crystallized during standing in a refrigerator (m.p.=65°~73° C.; yield: 0.53 g).

I. R. (KBr disc)cm$^{-1}$: 1600,1500,1240

N. M. R. δ(CDCl3)ppm: 2.2~2.5 (1H; m), 2.6~3.0 (1H; m), 3.76 (3H; s), 3.7~4.2 (5H; m), 6.79 (2H; d; J=9Hz), 6.83 (1H; d; J=2Hz), 7.05 (1H; d; J=2Hz), 7.29 (2H; d; J=9Hz)

(2) 6,7-Dihydro-7-mercapto-5H-pyrrolo(1,2-a)imidazole trifluoromethane sulfonate The objective compound was obtained by reacting the compound (0.50 g) obtained in the step (1) and subjecting the product to post-treatment according to the method similar to that in the step (7) of the reference example 12 (yield: 0.56 g).

N. M. R. δ(DMSO-d6+D2O)ppm: 2.0~2.7 (1H; m), 3.0~3.6 (1H; m), 4.24 (2H; m), 4.70 (1H; dd; J=4, 7Hz), 7.65 (2H; brs)

REFERENCE EXAMPLE 15

Synthesis of 6,7-dihydro-6-mercapto-5H-pyrrolo [1,2-a])imidazole trifluoromethane sulfonate

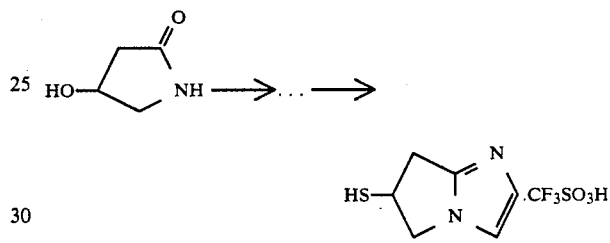

(1) 4-Benzoylthio-2-pyrrolidone

Triphenylphosphine (10.5 g) was dissolved in 50 ml of THF and THF (3 ml) solution of diethyl azodiethylcarboxylate (6.97 g) was added under ice cooling. After 30 minutes, THF 30 ml was added thereto and a suspension of 4-hydroxy-2-pyrrolidone (2.02 g) (synthesized by the method disclosed in Pellegata et al., "Synthesis", 615(1978)) and thiobenzoic acid (4.71 ml) in 80 ml THF was added thereto dropwise over 20 minutes. Further the solution was stirred for 1.5 hours at room temperature and concentrated in vacuo. The concentrate was dissolved in ethyl acetate and washed with 5% aqueous solution of sodium bicarbonate and then saturated aqueous solution of NaCl, dried over Na2SO4 and concentrated in vacuo. The residue was purified by chromatography utilizing 120 g of silica gel [eluted with a mixed solvent composed of benzene and ethyl acetate in which the mixing ratio is gradually changed from 1:1 to 1:4 and to 1:9] and the objective compound, as yellow powder, was obtained (m.p.=110°~112° C.; yield: 3.47 g).

I. R. (KBr disc)cm$^{-1}$: 1690, 1650

N. M. R. δ(CDCl3)ppm: 2.41 (1H; dd; J=6, 18Hz), 2.93 (1H; dd; J=9, 18Hz), 3.43 (1H; dd; J=5, 10Hz), 3.99 (1H; dd; J=8, 10Hz), 4.4 (1H; m), 6.8 (1H; br), 7.4~8.0 (5H; m)

(2) 4-(p-Methoxybenzylthio)-2-pyrrolidone

Sodium metal (0.37 g) was dissolved in 30 ml of methanol with ice cooling, then cooled to −10° C., added a solution of the compound (3.43 g) obtained in the step (1) in methanol (30 ml) and stirred for one hour at that temperature. After p-methoxybenzyl chloride (2.51 g) was added to this reaction solution at the same temperature, the solution was stirred for 1.5 hours at room temperature. The solvent was distilled off in vacuo, ethyl acetate was added and washed with water and further washed with 5% aqueous solution of sodium bicarbonate, 10% aqueous solution of citric acid and saturated aqueous solution of NaCl. The solution was dried over Na₂SO₄ and concentrated in vacuo. The residue was passed through a column packed with 160 g of silica gel to purify. The elution was first effected with benzene-ethyl acetate (1:1 v/v) mixed solvent (the amount of ethyl acetate was gradually increased) and then pure ethyl ace fractions containing the objective compound were combined and concentrated so that the objective compound, as colorless crystalline, was obtained (m.p.=95°~96° C. yield: 2.69 g).

I. R. (KBr disc)cm⁻¹: 3240, 1670, 1610, 1510

N. M. R. δ(CDCl₃)ppm: 2.16 (1H; dd; J=7, 18Hz), 2.64 (1H; dd; J=8, 18Hz), 3.2~3.6 (3H; m), 3.73 (2H; s), 3.80 (3H; s), 6.1 (1H; br), 6.85 and 7.27 (each 2H; each d; J=9Hz)

(3) 2-Ethoxy-4-p-methoxybenzylthio)-1-pyrroline

The Meerwein reagent (see, H. Meerwein, "Organic Synthesis", Coll. Vol. V, p. 1080) prepared from epichlorohydrin (2.75 ml) and BF₃(C₂H₅)₂O (5.89 ml) was dissolved in 30 ml of anhydrous dichloromethane, then the compound (2.37 g) obtained in the step (2) was added thereto with ice cooling and stirred for one hour at room temperature. The solution was made alkaline by the addition of 5% aqueous solution of sodium carbonate and extracted with dichloromethane. After the organic phase was washed with water and dried over Na₂SO₄, the phase was concentrated in vacuo. The residue was purified by column chromatography using a column packed with 50 g of silica gel [eluent: benzene/ethyl acetate (1:1 v/v)]. The fractions containing the objective compound were combined and concentrated in vacuo, so that the objective compound, as pale brown oil, was obtained (yield: 1.97 g).

N. M. R. δ(CDCl₃)ppm: 1.28 (3H; t; J=7Hz), 2.6 (2H; m), 3.4~3.9 (5H; m), 3.77 (3H; s), 4.17 (2H; q; J=7Hz), 6.82 and 7.21 (each 2H; each d; J=9Hz)

(4) 6,7-Dihydro-6-p-methoxybenzylthio-5H-pyrrolo(1,2-a)-imidazole

2-Ethoxy-4-p-methoxybenzylthio-1-pyroline (930mg) and aminoacetaldehyde dimethylacetal (552mg) were dissolved in 50 ml of methanol and refluxed under heating for one hour after the addition of acetic acid (315mg). Ethyl acetate and water were added thereto after cooling and the solution was made alkaline with 1N sodium hydroxide aq. solution before ,subjecting to distribution therebetween. The ethyl acetate phase was washed with water and saturated aqueous solution of NaCl, then the, phase was dried over Na₂SO₄ and concentrated in vacuo. The residue was dissolved in 70 ml of benzene, p-toluenesulfonic acid monohydrate (1 g) was added and refluxed under heating for three hours. The solvent was distilled off in vacuo, then water and ethyl acetate were added to the residue and the solvent was made alkaline with 5% aqueous solution of sodium bicarbonate before carrying out the distribution. After the ethyl acetate phase was washed with water and dried over Na₂SO₄, the phase was concentrated in vacuo. The residue was purified by column chromatography using a column packed with 25 g of silica gel [eluent: chloroform/methanol (19:1 v/v)] and the fractions containing the objective compound were combined and concentrated in vacuo so that the objective compound, as brown oil, was obtained (yield: 731mg).

N. M. R. δ(CDCl₃)ppm: 2.6~3.4 (2H; m), 3.5~4.2 (m), 3.77 (2H; s), 3.80 (3H; s), 6.79 and 7.02 (each 1H; J=1Hz), 6.85 and 7.24 (each 2H; J=9Hz)

(5) 6,7-Dihydro-6-mercapto-5H-pyrrolo(1,2-a)imidazole trifluoromethane sulfonate The compound (354mg) obtained in the preceeding step (4) was dissolved in a mixture of anisole (0.5 ml) and trifluoroacetic acid (4 ml), added 0.12 ml of trifluoromethane sulfonic acid under ice cooling, then brought back to room temperature and stirred for 30 minutes at that temperature. The reaction solution was subjected to post-treatment according to the procedures similar to those disclosed in the reference example 12-(7) to obtain the objective compound as brown oil (yield: 390mg).

N. M. R. δ(D₂O)ppm: 3.1~3.9 (3H; m), 4.1~4.6 (2H; m), 4.80 (HOD), 7.43 (2H; s)

REFERENCE EXAMPLE 16

Synthesis of 6,7-dihydro-6-mercapto-5H-pyrrolo [1,2-c]imidazole trifluoromethane sulfonate

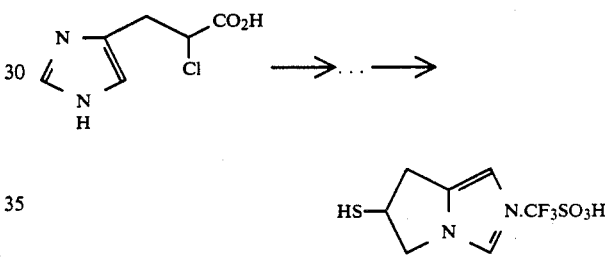

(1) 3-(Imidazol-4-yl)-2-p-methoxybenzylthio-propionic acid

2-Chloro-3-(imidazol-4-yl)propionic acid (6.01 g) prepared from L-histidine according to the method (see, Physiol. Chem., 1942, 276, 126) was dissolved in 50 ml of water containing 3.0 g of NaOH, added 5.3 g of p-methoxybenzylmercaptan and stirred for three days at room temperature. The reaction solution was washed with benzene, then pH of the water phase was adjusted to 3 to 4 by the addition of acetic acid and the water phase was concentrated under reduced pressure. The crystals precipitated were filtered out, washed with ethanol and ether and thus the objective compound was obtained as colorless needles (m.p.=85°~88° C.; yield: 5.8 g).

I. R. (KBr disc)cm⁻¹: 3500~2500, 1580, 1510

N. M. R. δ(NaOD)ppm: 2.92 (2H; m), 3.43 (1H; dd; J=7, 8Hz), 3.70 (2H; s), 3.81 (3H; s), 6.82 (1H; d; J=1Hz), 6.93 (2H; d; J=9Hz) 7.27 (2H; d; J=9Hz), 7.58 (1H; d; J=1Hz)

(2) Methyl 3-(imidazol-4-yl)-2-p-methoxybenzylthiopropionate 30 ml of methanol was cooled −10° C., added dropwise 0.47 ml of thionylchlcride while stirring and further stirred for 10 minutes. To this solution was added 1.46 g of the compound obtained in the above step (1) and stirred for one hour at room temperature. The solution was concentrated under reduced pressure, and after the addition of benzene to the resulting residue and distilling off the solvent under reduced pressure, 5% aqueous solution of sodium bicarbonate was added to the residue, then extracted with chloroform. The extract was dried over Na₂SO₄, distilled off the solvent under reduced pressure to obtain the objective compound (yield: 0.98 g).

N. M. R. δ(CDCl₃)ppm: 3.03 (2H; m), 3.54 (1H; dd; J=6, 8Hz), 3.70 (2H; s), 3.79 (3H; s), 6.82 (3H; m), 7.22 (2H; d; J=9Hz), 7.51 (1H; d; J=1Hz)

(3) 3-(Imidazol-4-yl)-2-(p-methoxybenzylthio)propanol

The compound (720 mg) obtained in the preceeding step (2) was dissolved in 15 ml of isopropanol, added 780 mg of calcium chloride and 180 mg of sodium borohydride and stirred for five hours at room temperature. To the reaction solution was added ethyl acetate and washed with water and saturated NaCl aq. solution, then dried over Na₂SO₄ and subjected to column chromatography using a small amount of silica gel before distilling off solvent under reduced pressure to obtain 566 mg of the objective product.

N. M. R. δ(CDCl₃)ppm: 2.93 (3H; m), 3.64 (2H; m), 3.68 (2H; s), 3.77 (3H; s), 6.76 (1H; d; J=1Hz), 6.81 (2H; d; J=9Hz), 7.20 (2H; d; J=9Hz), 7.50 (1H; d; J=1Hz)

Mass Spectrometric Analysis (m/e): 279 (M⁺+1)

(4) 4-(2-Chloro-3-p-methoxybenzylthiopropyl)imidazole

The compound (560 mg) obtained in the above step (3) was dissolved in a mixed solvent composed of 20 ml of THF and 10 ml of carbon tetrachloride, added 630 mg of triphenylphosphine and refluxed under heating for 2.5 hours. After cooling the solution, there was added triethylamine, distilled off the solvent under reduced pressure and the resulting residue was purified by column chromatography utilizing 15 g of silica gel and chloroform-methanol (9:1 v/v) as eluent to obtain 234 mg of the objective compound.

N. M. R. δ(CDCl₃)ppm: 2.79 (2H; d; J=6Hz), 3.14 (2H; m), 3.72 (2H; s), 3.78 (3H; s), 4.22 (1H; m), 6.82 (2H; d; J=9Hz), 6.87 (1H; d; J=1Hz), 7.21 (2H; d; J=9Hz), 7.56 (1H; d; J=1Hz), 7.80 (1H; brs)

(5) 6,7-Dihydro-6-p-methoxybenzylthio-5H-pyrrolo[1,2-c]imidazole

The compound (2.21 g) obtained in the step (4) was dissolved in 40 ml of acetone, added 11.19 of sodium iodide and refluxed under heating for 24 hours. The solvent was distilled off under reduced pressure, added chloroform to the residue and washed with dilute aqueous solution of NaOH and saturated NaCl aq. solution. The solution was dried over Na₂SO₄, distilled off the solvent under reduced pressure and the residue was purified by passing it through a column packed with 60 g of silica gel and eluting with chloroform-methanol (19:1 v/v) to obtain 0.89 g of the objective compound. 2.6~3.4 (2H; m), 3.77 (2H; s), 3.8 (3H; s), 3.5~4.25 (3H; m), 6.70 (1H; s), 6.86 (2H; d; J=9Hz), 7.25 (2H; d; J=9Hz), 7.42 (1H; s)

Mass Spectrometric Analysis (m/e): 260 (M⁺)

(6) 6,7-Dihydro-6-mercapto-5H-pyrrolo(1,2-c)imidazole trifluoromethane sulfonate The compound (323 mg) obtained in the above step (5) was dissolved in a mixture of anisole (0.4 ml) and trifluoroacetic acid (4 ml), added 0.12 ml of trifluoromethane sulfonic acid under ice cooling and stirred for 30 minutes at room temperature. The solvent was distilled off under reduced pressure. Then, there was added xylene to the residue and distilled off the solvent under reduced pressure, which were repeated a few times. The residue obtained was washed with ether to obtain 360 mg of the objective compound.

TLC: Rf=0.05

[Using silica gel plate (Merck), 0.25 mm in thick; developing solvent: chloroform-methanol (9:1 v/v mixture); colored purple with sodium nitroprusside]

N. M. R. δ(D₂O)ppm: 2.9~3.9 (3H; m), 4.2~4.6 (2H; m), 4.80 (HOD), 7.24 (1H; s), 8.65 (1H; s)

REFERENCE EXAMPLE 17

Synthesis of 6,7-dihydro-1-hydroxy-6-mercapto-5H-pyrrolo[1,2-c]imidazole

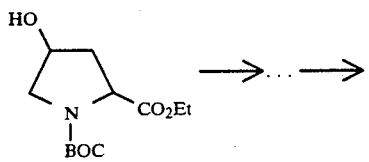

→ ... →

(1) 1-t-Butoxycarbonyl-2-ethoxycarbonyl-4-oxopyrrolidine

Ethyl ester of 1-t-butoxycarbonyl-L-hydroxy-proline (7.77 g) was dissolved in DMSO (30 ml), added dicyclohexylcarbodiimide (18.4 g) and 2.4 ml of pyridine and 1.2 ml of trifluoroacetic acid were added dropwise at room temperature while stirring. The mixture was stirred for two hours at that temperature, then ethyl acetate was added to the reaction mixture and insolubles were filtered off. The filtrate was washed with water, dried over Na₂SO₄ and distilled off the solvent used, under reduced pressure. The residue was passed through a column packed with 120 g of silica gel and eluted with benzene-ethyl acetate (98: 2 v/v) and thus the objective compound was obtained (yield: 7.1 g).

N. M. R. δ(CDCl₃)ppm: 1.28 (3H; t; J=6Hz), 1.48 (9H; s), 2.40~3.13 (2H; m), 3.86 (2H; s), 4.18 (2H; q; J=6Hz), 4.65~4.85 (1H; m)

(2) 1-t-Butoxycarbonyl-2-ethoxycarbonyl-4-hydroxypyrrolidine

The compound (9.4 g) obtained in the preceeding step (1) was dissolved in methanol (100 ml), added 0.7 g of sodium borohydride at a temperature of from 0° to 5° C. and stirred for 30 minutes at that temperature. Then, the solvent was evaporated under reduced pressure, added ethyl acetate, water and ammonium chloride to the residue and the organic phase was isolated. After washing it with water and saturated NaCl aqueous solution and drying over Na₂SO₄, the solvent thereof was distilled off under reduced pressure to obtain the objective compound (yield: 9.4 g).

(3)
1-t-Butoxycarbonyl-2-ethoxycarbonylpyrrolidin-4-yl tosylate

The compound (9.5 g) obtained in the step (2) was dissolved in pyridine (100 ml), cooled to 0 to 5° C, added p-toluenesulfonyl chloride (10.5 g) with stirring and then continuously stirred for 17 hours at room temperature. The solvent was distilled off under reduced pressure. Then, ethyl acetate was added, washed with water, dried over $Na_2SO_4$ and distilled off the solvent under reduced pressure. The resultant residue was passed through a column packed with 150 g of silica gel and eluted with 95:5 mixture of benzene and ethyl acetate as an eluent to obtain the product mentioned above (yield: 13.4 g).

N. M. R. $\delta(CDCl_3)$ppm: 1.23 (3H; t; J=6Hz), 1.43 (9H; s), 2.20~2.53 (5H; m), 3.50~3.65 (2H; m), 3.95~4.45 (3H; m), 4.86~5.10 (1H; m), 7.25 (2H; d; J=9Hz), 7.66 (2H; d; J=9Hz)

(4)
1-t-Butoxycarbonyl-2-ethoxycarbonyl-4-p-methoxybenzylthiopyrrolidine 13 g of the compound obtained in the step (3) was dissolved in 300 ml of benzene, then 9.7 g of p-methoxybenzylmercaptan and 9.6 g of DBU were added to the solution and the mixture was refluxed under heating for 7 hours in the argon atmosphere. After evaporating the solvent under reduced pressure, the residue obtained was purified by column chromatography utilizing 300 g of silica gel and 95:5 mixture of benzene and ethyl acetate as an eluent to obtain the product mentioned above (yield: 10.3 g).

N M. R. $\delta(CDCl_3)$ppm: 1.25 (3H; t; J=6Hz), 1.42 (9H; s), 1.70~2.60 (2H; m), 3.00~3.30 (2H; m), 3.67 (2H; s), 3.77 (3H; s), 4.00~4.30 (3H; m), 6.78 (2H; d; J=9Hz), 7.16 (2H; d; J=9Hz)

(5)
1-t-Butoxycarbonyl-2-carbamoyl-4-p-methoxybenzylthiopyrrolidine 1.76 g of the compound prepared in the preceeding step (4) was dissolved in 30 ml of methanol, added 30 ml of 30% aqueous ammonia and stirred for 40 hours at 40° to 45° C. in a sealed tube. The reaction mixture was extracted with ethyl acetate, washed with 10% aqueous citric acid solution and saturated NaCl aqueous solution, and the solvent was evaporated off under reduced pressure after drying over $Na_2SO_4$. The residue obtained was passed through a column packed with 30 g of silica gel and eluted with 9:1 mixture of chloroform and methanol to purify the product and thus 1.00 g of the objective compound was obtained.

N. M. R. $\delta(CDCl_3)$ppm: 1.45 (9H; s), 1.80~2.80 (2H; m), 3.20~3.70 (3H; m), 3.73 (2H; s), 3.79 (3H; s), 4.30 (1H; m), 6.84 (2H; d; J TM 9Hz), 7.23 (2H; d; J=9Hz)

(6) 2-carbamoyl-4-p-methoxybenzylthiopyrrolidine

To a mixture of the compound = (1.00 g) obtained in the above step (5) and anisole (1.0 ml), was added 7 ml of trifluoroacetic acid and stirred for 40 minutes at room temperature. The solvent was evaporated under reduced pressure, then ether was added to the residue and washed. The residue was dissolved in dilute hydrochloric acid solution and washed with ether. The water phase was made alkaline by the addition of dilute aqueous NaOH solution and extracted with chloroform. After drying over $Na_2SO_4$ and distilling off the solvent under reduced pressure, 0.59 g of the objective compound was obtained as white solid.

I. R. (KBr disc)cm$^{-1}$: 3400, 2800, 1650, 1515

N. M. R. $\delta(CDCl_3)$ppm: 2.20 (2H; m), 2.90 (2H; m), 3.20 (1H; m), 3.69 (2H; s), 3.80 (3H; s), 3.90 (1H; m), 6.84 (2H; d; J=9Hz), 7.22 (2H; d; J=9Hz)

(7)
6,7-Dihydro-1-hydroxy-6-p-methoxybenzylthio-5H-pyrrolo-[1,2-c]imidazole 0.59 g of the compound obtained in the preceeding step (6) was dissolved in 30 ml of ethanol, added 1.96 g of ethyl ester of ortho formic acid and 8 mg of p-toluene sulfonic acid hydrate and refluxed for three hours. After removing the solvent, the residue was purified by passing it through a column packed with 20 g of silica gel and eluting with mixture of chloroform-methanol (49:1 v/v) to obtain the objective compound (yield: 278 mg).

N M. R. $\delta(CDCl_3)$ppm: 2.60~3.35 (2H; m), 3.72 (2H; s), 3.80 (3H; s), 6.85 (2H; d; J=9Hz), 7.23 (2H; d; J=9Hz), 8.16 (1H; s)

(8)
6,7-Dihydro-1-hydroxy-6-mercapto-5H-pyrrolo[1,2,-c]imidazole

To 358 mg of the product in the above step (7) there were added 0.5 ml of anisole and 4 ml of trifluoroacetic acid and further added 0.1 ml of trifluoromethane sulfonic acid and stirred for three hours at room temperature. The solvent was evaporated off under reduced pressure, xylene was then added and distilled off under reduced pressure, these procedures being repeated several times. The product was then washed with petroleum ether and dried under reduced pressure to obtain the objective compound (yield: 390 mg).

TLC: Rf=0.2 [Silica Gel Plate (Merck), 0.25 mm in thick; developing solvent: $CHCl_3$: $CH_3OH$ (9:1 v/v); colored purple with sodium nitroprusside]

N. M. R. $\delta(D_2O+DMSOd_6)$ppm: 2.9~3.35 (2H; m), 4.2~4.5 (2H; m), 7.25 (1H; s), 8.36 (1H; s)

REFERENCE EXAMPLE 18

Synthesis of 6,7-dihydro-6-mercapto-5H-pyrrolo[2,1-c]-1,2,4-triazole trifluoromethane sulfonate

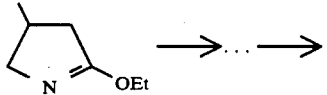 → ... → 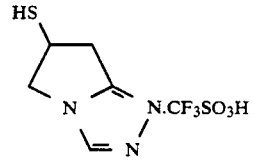

(1)
6,7-Dihydro-6-p-methoxybenzylthio-5H-pyrrolo[2,1-c]-1,2,4-triazole

To a solution of 2-ethoxy-4-p-methoxybenzylthio-1-pyrroline (1.06 g) in ethanol (50 ml) there was added 0.36 g of formylhydrazine and heated to 80° C. under argon atmosphere while stirring. After 1.5 hours, 0.24 g of formylhydrazine was further added and stirred under heating for 30 minutes at the same temperature. Then, 0.6 g of acetic acid was added, stirred for 30 minutes at that temperature and then cooled to room temperature. To the cooled product were added ethyl acetate and 5% aqueous solution of sodium carbonate to distribute the product between these two liquids. The resulting organic phase was washed with saturated NaCl aqueous solution, dried over $Na_2SO_4$ and distilled off the solvent under reduced pressure to obtain the objective product.

Mass Spectrometric Analysis (m/e): 279 (M+)

N. M. R. δ(CDCl$_3$)ppm: 2.3~3.0 (2H; m), 3.3 (2H; m), 3.7 (1H; m), 3.79 (3H; s), 6.83 (2H; d; J=9Hz), 7.21 (2H; d; J=9Hz), 7.85 and 8.34 (each 0.5H; each s)

To the resultant residue was added 20 ml of acetic acid
at 100° C. for four hours. After cooling, the reaction liquid was poured into ice water and subjected to extraction with ethyl acetate after neutralizing it with sodium carbonate. The organic phase was washed, dried over $Na_2SO_4$ and concentrated under reduced pressure. Then, the residue obtained was subjected to column chromatography utilizing 20 g of silica gel and a mixture of CHCl$_3$ and CH$_3$OH (9:1 v/v) as an eluent and 516 mg of the objective compound was obtained as brown solid.

I. R.(KBr disc)cm$^{-1}$: 1600, 1520, 1500

N. M. R. δ(CDCl$_3$)ppm: 2.7~3.4 (2H; ddd), 3.80 (2H; s), 3.81 (3H; s), 3.8~4.2 (3H; m), 6.86 (2H; d; J=9Hz), 7.24 (2H; d; J=9Hz), 8.02 (1H; s)

(2)
6,7-Dihydro-6-mercapto-5H-pyrrolo[2,1-c]-1,2,4-triazole 210 mg of the compound obtained in the preceeding step (1) was dissolved in a mixture of anisole (0.5 ml) and trifluoroacetic acid (4 ml), added 0.09 ml of trifluoromethane sulfonic acid under ice cooling and stirred for 20 minutes at room temperature. The reaction liquid was concentrated under reduced pressure, added 20 ml of xylene and concentrated. Similarly, xylene was added and concentrated, these procedures being repeated two times. The residue was washed with ether under agitation and ether was removed by decantation. The washing procedure with ether was repeated twice and concentrated under reduced pressure to obtain the objective compound as brown oil (yield: 250 mg).

N. M. R. δ(D$_2$O)ppm: 3.1~4.0 (3H; m), 4.2~4.6 (2H; m), 9.23 (1H; s)

REFERENCE EXAMPLE 19

Synthesis of
3-amino-6,7-dihydro-6-mercapto-5H-pyrrolo-[2,1-c]-1,2,4-triazole trifluoromethane sulfonate

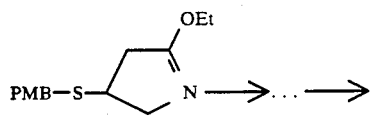

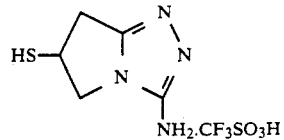

(1) 4-p-Methoxybenzylthio-2-thiosemicarbazono pyrrolidine

A solution of 2-ethoxy-4-p-methoxybenzylthio-1-pyrroline (900 mg) and thiosemicarbazide hydrochloride (433 mg) in ethanol (30 ml) was refluxed under heating for 1.5 hours. The reaction solution was evaporated to dryness under reduced pressure, then the residue was distributed between ethyl acetate and 5% aqueous solution of sodium hydroxide and the organic phase was dried over $Na_2SO_4$ before the solvent was distilled off under reduced pressure. The resultant residue was passed through a column packed with 25 g of silica gel and eluted with ethyl acetate and thus 230 mg of the objective compound was obtained as colorless foam.

N. M. R. δ(CDCl$_3$)ppm: 2.3~3.0 (2H; m), 3.2~3.5 (2H; m), 3.72 (2H; s), 3.80 (3H; s), 3.70~4.0 (1H; m), 6.85 (2H; d; J=9Hz), 7.23 (2H; d; J=9Hz)

Mass Spectrometric Analysis (m/e): 311 (M+ +1)

(2)
4-p-Methoxybenzylthio-2-(3-methylisothiosemicarbazido)-1-pyrroline

The compound (230 mg) prepared in the preceeding step (1) was dissolved in ethanol (20 ml), added 312 mg of methyl iodide and stirred at room temperature for five hours. The reaction solution was evaporated to dryness under reduced pressure, the resultant residue was distributed between ethyl acetate and 30 ml of water containing 2 ml of aqueous solution of 1N NaOH and the organic phase was washed and dried over Na$_2$SO$_4$ before distilling off the solvent. Thus, 195 mg of the product mentioned above as pale yellow oil obtained.

N. M. R. δ(CDCl$_3$)ppm: 2.40 (3H; s), 2.48 (1H; dd; J=8, 16Hz), 2.85 (1H; dd; J=8, 16Hz), 3.2~3.7 (3H; m), 3.75 (2H; s), 3.80 (3H; s), 5.05 (2H; brs), 5.75 (1H; brs), 6.84 (2H; d; J=9Hz), 7.24.(2H; d; J=9Hz)

Mass Spectrometric Analysis (m/e): 324 (M+)

(3)
3-Amino-6,7-dihydro-6-(p-methoxybenzylthio)-5H-pyrrolo [2,1-c]-1,2,4-triazole:

190 mg of the compound obtained in the preceeding step (2) was dissolved in a mixed solvent consisting of ethanol (4 ml) and 1N aqueous solution of NaOH (2 ml) and refluxed under heating for 30 minutes. After cooling, the crystals separated out were filtered off and washed with water, ethanol and ether to obtain 98 mg of the objective compound
m.p.: 245°~248° C. (dec.)

N. M. R. δ(DMSO-d$_6$)ppm: 2.7~4.1 (5H; m), 3,76 (3H; s), 3.81 (2H; s), 5.64 (1H; s), 6.88 (2H; d; J=9Hz), 7.28 (2H; d; J=9Hz), 8.32 (1H; s)

Elemental Analysis (%): (for C$_{13}$H$_{16}$N$_4$OS)

|  | C | H | N |
| --- | --- | --- | --- |
| Calculated: | 56.50 | 5.85 | 20.27 |
| Found: | 56.31 | 5.74 | 20.00 |

(4)

3-Amino-6,7-dihydro-6-mercapto-5H-pyrrolo[2,1-c]-1,2,4-triazole trifluoromethane sulfonate According to the procedures similar to those disclosed in the reference example 12 (step (7)), the compound (94 mg) obtained in the above step (3) was treated and post-treated to obtain 100 mg of the objective product.

N. M. R. δ(D$_2$O)ppm: 2.8~3.1 (1H; m), 3.4~3.6 (1H; m), 3.8~4.0 (1H; m), 4.2~4.6 (2H; m), 4.80 (HOD)

REFERENCE EXAMPLE 20

Synthesis of 2,3-dihydro-2-mercapto-1H-pyrazolo[1,2-a]pyrazolium trifluoromethane sulfonate

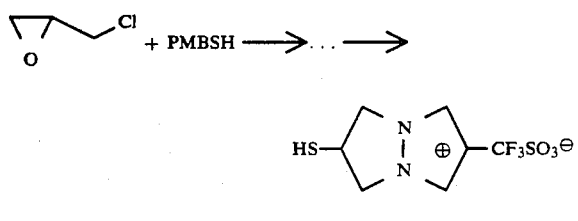

(1)

1-Chloro-2-hydroxy-3-p-methoxybenzylthiopropane 2.78 ml of epichlorohydrin and 2.78 ml of p-methoxybenzylmercaptan were heated with stirring at 120 to 130° C. for three hours. After cooling, the product was purified by column chromatography using 100 g of silica gel and benzene as an eluent to obtain 1.44 g of the objective compound.

N. M. R. δ(CDCl$_3$)ppm: 2.40~2.80 (2H; m), 2.84 (1H; brs), 3.50~3.64 (2H; m), 3.70 (2H; s), 3.78 (3H; s), 6.85 (2H; d; J=9Hz), 7.25 (2H; d; J=9Hz)

(2) 1,2-Epoxy-3-p-methoxybenzylthiopropane

To the compound (1.44 g) obtained in the preceeding step (1) was added a solution of NaOH (0.28 g) in water (1.8 ml) and stirred at room temperature for 17 hours. To the reaction solution was added dichloromethane, washed, dried over Na$_2$SO$_4$ and then the solvent was distilled off under reduced pressure. The residue was purified by passing it through a column packed with 20 g of silica gel and eluting with chloroform to obtain 0.54 g of the objective compound.

N. M. R. δ(CDCl$_3$)ppm: 2.45~2.85 (4H; m), 2.96~3.20 (1H; m), 3.76 (2H; s), 3.79 (3H; s), 6.85 (2H; d; J=9Hz), 7.27 (2H; d; J=9Hz)

(3)

1-(2-Hydroxy-3-p-methoxybenzylthiopropyl)pyrazole

The compound (500 mg) obtained in the preceeding step (2) and pyrazole (190 mg) were dissolved in DMF (2.5 ml), added 655 mg of potassium carbonate and stirred at 90° C for seven hours. The solvent was distilled off under reduced pressure and the residue was purified by passing it through a column packed with 20 g of silica gel and eluting with chloroform-methanol (99:1 v/v) to obtain 660 mg of the objective compound.

N. M. R. δ(CDCl$_3$)ppm: 2.32~2.52 (2H; m), 3.70 (2H; s), 3.78 (3H; s), 3.80~4.28 (3H; m), 6.26 (1H; t; J=3Hz), 6.82 (2H; d; J=9Hz), 7.20 (2H; d; J=9Hz), 7.41 and 7.53 (each 1H; each d; J=3Hz)

(4) 1-(3-Chloro-2-p-methoxybenzylthiopropyl)pyrazole 600 mg of the compound prepared in the preceeding step (3) was dissolved in 6 ml of carbon tetrachloride, added 680 mg of triphenylphosphine and stirred for 17 hours at 50 to 60° C. After removing the solvent by evaporation under reduced pressure, the residue obtained was purified by column chromatography using 15 g of silica gel and chloroform as an eluent to obtain 480 mg of the objective compound.

N. M. R. δ(CDCl$_3$)ppm: 3.10~3.63 (5H; m), 3.79 (3H; s), 4.10~4.60 (2H; m), 6.26 (1H; t; J=3Hz), 6.82 (2H; d; J=9Hz), 7.20 (2H; d; J=9Hz), 7.45 and 7.56 (each 1H; each d; J=3Hz) (5) 2,3-Dihydro-2-p-methoxybenzylthio-1H-pyrazolo[1,2-a]pyrazolium iodide The compound (0.46 g) obtained in the step (4) was dissolved in acetone (40 mg) and 1.3 g of potassium iodide was added, then refluxed under heating for 30 hours. The solvent was removed by distillation under reduced pressure, added ether to the residue, the ether phase was removed and added chloroform to the precipitates formed, thereafter insolubles were removed by filtration. The resulting filtrate was concentrated under reduced pressure and thus, the objective compound was obtained (yield: 0.28 g).

N. M. R. δ(CDCl$_3$)ppm: 3.82 (3H; s), 3.93 (2H; m), 4.35~4.70 (3H; m), 5.00~5.35 (2H; m), 6.70~7.00 (3H; m), 7.33 (2H; m), 8.37 (2H; d; J=3Hz)

(6)

2,3-Dihydro-2-mercapto-1H-pyrazolo(1,2-a)pyrazolium trifluoromethane sulfonate

The compound (0.28 g) obtained in the step (5) was dissolved in a mixture of anisole (0.5 ml) and trifluoroacetic acid (4 ml), added 0.5 ml of trifluoromethane sulfonic acid and stirred at room temperature for one hour. After the solvent was distilled off under reduced pressure, adding xylene to the residue and concentrating the solution under reduced pressure were repeated a few times. The objective compound was obtained after washing the residue with petroleum ether (yield: 0.2 g).

N. M. R. δ(D$_2$O)ppm: 4.40~4.70 (3H; m), 4.80 (HOD), 6.92 (1H; t; J=3Hz), 8.26 (2H; d; J=3Hz)

REFERENCE EXAMPLE 21

Synthesis of 1-mercapto-4-methylpyrrolizidinium trifluoromethane sulfonate

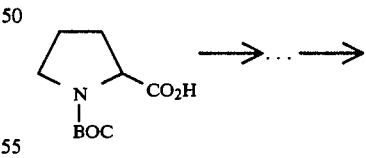

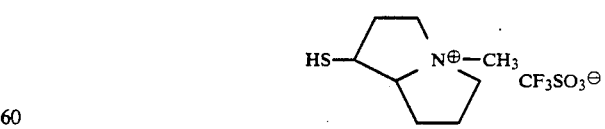

(1) Ethyl 3-(1-t-butoxycarbonylpyrolidin-2-yl)-3-oxopropionate

To 9 ml of ethanol was added 0.57 g of magnesium, further added 1.5 ml of carbon tetrachloride and stirred for two hours at room temperature. To the mixture was added a solution of monoethyl malonate (6.75 g) in THF (30 ml) and the solvent was distilled off under reduced pressure when the reaction solution became transparent. While butoxycarbonylproline (6.45 g) was dissolved in THF (50 ml), added 5.35 g of carbonyldiimidazole with stirring at room temperature and then stirred at that temperature for 30 minutes. To the mixture was added the THF solution of magnesium complex obtained above and stirred at room temperature for two hours. Ethyl acetate was added to the reaction solution, then washed with 1N HCl, saturated aqueous solution of sodium bicarbonate and water in this order, dried over $Na_2SO_4$ and distilled off the solvent under reduced pressure. The resultant residue was passed through a column packed with 100 g of silica gel and then eluted with a mixture of benzene and ethyl acetate (95:5 v/v) to obtain the purified objective product (yield: 6 g).

N. M. R. $\delta(CDCl_3)$ppm: 1.26 (3H; t; J=6Hz), 1.45 (9H; s), 1.70~2.30 (4H; m), 3.30~3.63 (4H; m), 4.16 (2H; q; J=6Hz), 4.10~4.45 (1H; m)

(2) Ethyl 3-(1-t-butoxycarbonylpyrrolidin-2-yl)-3-hydroxypropionate

The compound (3 g) obtained in the preceeding step (1) was dissolved in methanol (30 ml), cooled to 0 to 5° C, added, with stirring, 200 mg of sodium borohydride and stirred at room temperature for one hour. To the mixture there were added 2 g of ammonium chloride and water, extracted with chloroform, washed with saturated NaCl aq. solution, dried over $Na_2SO_4$ and distilled off the solvent under reduced pressure. The resulting residue was passed through a column packed with 50 g of silica gel and eluted with chloroform-methanol (99:1 v/v) to obtain the purified objective product (yield: 3 g).

N. M. R. $\delta(CDCl_3)$ppm: 1.26 (3H; t; J=6Hz), 1.47 (9H; s), 1.60~2.10 (4H; m). 2.33~2.53 (2H; m), 3.10~3.60 (2H; m), 3.75~4.10 (1H; m), 4.13 (2H; q; J=6Hz)

(3) Ethyl β-(1-t-butoxycarbonylpyrrolidin-2-yl)acrylate

The compound (2.87 g) obtained in the preceeding step (2) was dissolved in pyridine (20 ml), added, under ice cooling and stirring, 3.9 g of p-toluenesulfonyl chloride and stirred for 17 hours at room temperature. After further stirring for one hour at 60° to 70° C., the solvent was distilled off, added ethyl acetate to the residue, washed with water, dried over $Na_2SO_4$ and distilled off the solvent under reduced pressure. The resulting residue was purified by column chromatography using 50 g of silica gel and a mixed solvent composed of benzene and ethyl acetate (95:5 v/v) to obtain crude tosyl derivative of the objective compound. The tosyl derivative was dissolved in 50 ml of chloroform and added 1.5 g of DBU before refluxing under heating for 20 minutes. Then, the solvent was distilled off under reduced pressure, added ethyl acetate to the residue, washed with water, 0.5N HCl and saturated NaCl aq. solution in this order and dried over $Na_2SO_4$. The objective compound (2 g) was thus obtained after the removal of solvent by distillation under reduced pressure.

N. M. R. $\delta(CDCl_3)$ppm: 1.26 (3H; t; J=6Hz), 1.43 (9H; s), 1.60~2.20 (4H; m), 3.30~3.55 (2H; m), 4.16 (2H; q; J=6Hz), 5.77 (1H; d; J=15Hz), 6.77 (1H; dd; J=6, 15Hz)

(4) Ethyl 3-(1-t-butoxycarbonylpyrrolidin-2-yl)-3-p-methoxybenzylthiopropionate The compound (2 g) obtained in the preceeding step (3) was dissolved in chloroform (30 ml), added 1.6 g of p-methoxybenzylmercaptan and 1.6 g of DBU and stirred for 17 hours at room temperature. The residue, obtained after removing the solvent by distillation effected under reduced pressure, was purified by passing it through a column packed with 50 g of silica gel and eluting with benzene-ethyl acetate (98:2 v/v) to obtain the objective product (yield: 2.52 g).

N. M. R. $\delta(CDCl_3)$ppm: 1.23 (3H; t; J=6Hz), 1.46 (9H; s), 1.65~2.10 (4H; m), 2.42~2.66 (2H; m), 3.10~3.70 (3H; m), 3.74 (5H; s), 3.96~4.30 (3H; m), 6.75 (2H; d; J=9Hz), 7.10~7.30 (2H; m)

(5) 3-(1-t-Butoxycarbonylpyrrolidin-2-yl)-3-p-methoxybenzylthiopropanol

The compound (2.52 g) obtained in the step (4) was dissolved in THF (40 ml), added 0.2 g of sodium borohydride under ice cooling and stirred for 17 hours at room temperature. To the reaction mixture there were added ammonium chloride and water under stirring and ice cooling and then extracted with ethyl acetate. The organic phase was isolated, washed with saturated NaCl aq solution, dried over $Na_2SO_4$ and distilled off the solvent under reduced pressure. The residue was purified by column chromatography using 20 g of silica gel and chloroform as an eluent to obtain 2.14 g of the objective compound.

N. M. R. $\delta(CDCl_3)$ppm: 1.47 (9H; s), 1.50~2.20 (7H; m), 3.10~3.80 (6H; m), 3.74 (3H; s), 3.80~4.20 (1H; m), 6.76 (2H; d; J=9Hz), 7.10~7.30 (2H; m)

(6) 3-(1-t-Butoxycarbonylpyrrolidin-2-yl)-3-p-methoxybenzylthiopropyl tosylate The compound (2.64 g) obtained in the step (5) was dissolved in 30 ml of pyridine, added 1.98 g of p-toluenesulfonyl chloride under ice cooling, and stirred for 17 hours at the same temperature. The solvent was distilled off under reduced pressure, added ethyl acetate to the residue, washed with water, dried over $Na_2SO_4$ and the solvent was distilled off under reduced pressure. The residue thus obtained was purified by passing it through a column packed with 40 g of silica gel and eluting the product with a mixed solvent composed of benzene-ethyl acetate (98:2 v/v) and thus 2.68 g of the objective compound was obtained.

N. M. R. $\delta(CDCl_3)$ppm: 1.47 (9H; s), 1.50~2.20 (6H; m), 2.43 (3H; s), 3.10~3.73 (5H; m), 3.77 (3H; s), 3.80~4.30 (3H; m), 6.75 (2H; d; J=9Hz), 7.03~7.40 (4H; m), 7.72 (2H; d; J=9Hz)

(7) 3-p-Methoxybenzylthio-3-(pyrrolidin-2-yl)-propyl tosylate trifluoroacetate To 2.68 g of the compound prepared in the preceeding step (6) was added 3 ml of anisole and further added 10 ml of trifluoroacetic acid under ice cooling and stirring and further stirred for 30 minutes at that temperature. To the residue, obtained after distilling off the solvent under reduced pressure, was added toluene and distilled off the solvent under reduced pressure. After washing the residue with petroleum ether and removing the solvent, the objective compound (yield: 2.7 g) was obtained.

N. M. R. δ(CDCl₃)ppm: 1.45~2.30 (6H; m), 2.42 (3H; s), 2.70~3.60 (4H; m), 3.63 (2H; s), 3.77 (3H; s), 4.00~4.25 (2H; m), 6.75 (2H; d; J=9Hz), 7.02~7.40 (4H; m), 7.73 (2H; d; J=9Hz)

(8) 1-p-Methoxybenzylthiopyrrolizidine

The compound (2.7 g) obtained in the step (7) was dissolved in DMF (20 ml), added 1.73 g of .potassium carbonate and stirred for 17 hours at room temperature. The solvent was distilled off under reduced pressure after stirring two hours at 80° C. To the residue was added chloroform, washed with water, dried over Na₂SO₄ and then the solvent was evaporated under reduced pressure. The residue was purified by column chromatography using 15 g of silica gel and a mixed solvent composed of chloroform-methanol (95:5 v/v) to obtain the objective product (yield: 0.9 g).

N. M. R. δ(CDCl₃)ppm: 1.50~2.30 (6H; m), 2.30~3.60 (6H; m), 3.64 (2H; s), 3.74. (3H; s), 6.75 (2H; d; J=9Hz), 7.15 (2H; d; J=9Hz)

(9) 1-p-Methoxybenzylthio-4-methylpyrrolizidinium iodide

The compound (260 mg) obtain®d in the step (8) was dissolved in 5 ml of acetone, added 710 mg of methyl iodide and kept standing at room temperature for 48 hours. The reaction mixture was concentrated under reduced pressure and the residue was washed with ether to obtain the objective compound (yield: 400 mg)

(10) 1-Mercapto-4-methylpyrrolizidinium trifluoromethane sulfonate

To the compound (400 mg) obtained in the preceeding step (9) was added 0.7 ml of anisole and 4 ml of trifluoroacetic acid, added dropwise 0.5 ml of trifluoromethane sulfonic acid at room temperature under stirring and further stirred for 30 minutes at the same temperature. After removing the solvent by evaporation, the resultant residue was dispersed in xylene and distilled under reduced pressure (these operation being repeated three times). The residue was washed with ether and dried to obtain 300 mg of the objective compound.

N. M. R. δ(D₂O)ppm: 1.90~2.80 (6H; m), 3.23 and 3.28 (each 3H; each s), 3.30~4.15 (6H; m), 4.80 (HOD)

REFERENCE EXAMPLE 22

Synthesis of 4-(2-fluoroethyl)-1-mercaptopyrrolizidinium trifluoromethane sulfonate:

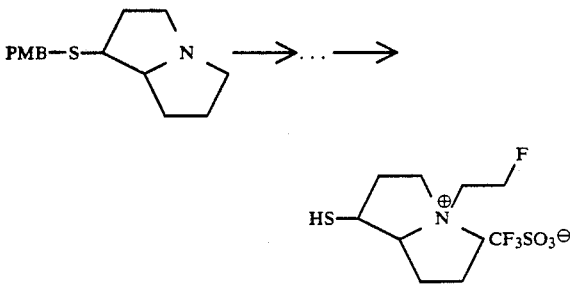

(1)
4-(2-Fluoroethyl)-1-p-methoxybenzylthiopyrrolizidinium bromide

The product (1-p-methoxybenzylthiopyrrolizidine (263 mg) obtained in the step (8) of the reference example 21 was dissolved in 5 ml of acetone, added 640 mg of 1-bromo-2-fluoroethane and kept standing for four days. The solvent was distilled off under reduced pressure, the resultant residue was washed with ether and dried to obtain the objective compound (yield: 390 mg).

N. M. R. δ(CDCl₃)ppm: 1.60~2.40 (6H; m), 2.80~4.20 (13H; m), 4.60~4.80 (1H; m), 5.15~5.35 (1H; m), 6.84 (2H; d; J=9Hz), 7.20~7.40 (2H; m)

(2) 4-(2-Fluoroethyl)-1-mercaptopyrrolizidinium trifluoromethane sulfonate

To the compound (390 mg) obtained in the preceeding step (1) was added 0.7 ml of anisole and 4 ml of trifluoroacetic acid, added dropwise 0.5 ml of trifluoromethane sulfonic acid at room temperature under stirring and further stirred for 30 minutes at that temperature. The solvent was distilled off under reduced pressure, added xylene to the resulting residue and the solvent was again distilled off in vacuo. The residue was washed with ether and dried to obtain 330 mg of the objective compound.

N. M. R. δ(D₂O)ppm: 1.80~2.80 (6H; m), 3.20~4.20 (8H; m), 4.80 (HOD), 5.10~5.30 (1H; m)

REFERENCE EXAMPLE 23

Synthesis of 2-mercapto-4-methyl-pyrrolizidinium trifluoromethane sulfonate

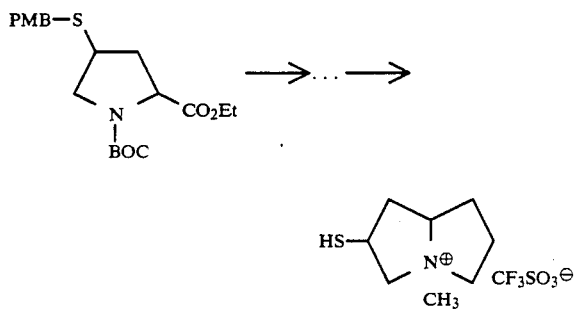

(1)
1-t-Butoxycarbonyl-4-p-methoxybenzylthiopyrrolidin-2-yl-methanol

The compound (4.3 g) obtained in the step (4) of the reference example 17 was dissolved in 50 ml of THF, added 0.2 g of sodium borohydride and stirred at room temperature for 17 hours. There were added water and ammonium chloride and extraction was effected with ethyl acetate. The solvent was distilled off under reduced pressure after drying over Na₂SO₄. The residue was purified by passing it through a column packed with 60 g of silica gel and eluting the product with chloroform to obtain the objective compound (yield: 3.8 g).

N. M. R. δ(CDCl₃)ppm: 1.46 (9H; s), 1.80~2.10 (2H; m), 3.06~3.65 (5H; m), 3.68 (2H; s), 3.78 (3H; s), 3.90~4.30 (1H; m), 6.78 (2H; d; J=9Hz), 7.18 (2H; d; J=9Hz)

(2) 2-Ethoxycarbonyl-3-(1-t-butoxycarbonyl-4-p-methoxybenzylthiopyrrolidin-2-yl)propionitrile Triphenylphosphine (1.2 g) was dissolved in THF (9 ml), added 0.78 g of diethyl azodicarboxylate under ice cooling and stirring and further stirred for 30 minutes at that temperature. To the reaction solution there were added the compound (1.06 g) obtained in the step (1), ethyl cyanoacetate (0.34 g) and 2,6-di-t-butylphenol (0.63 g) in THF (6 ml) and stirred for two hours at room temperature. The residue, obtained after distilling off the solvent under reduced pressure, was purified by column chromatography using 40 g of silica gel and benzene-ethyl acetate (95:5 v/v) as an eluent to obtain 0.65 g of the compound mentioned above.

N. M. R. $\delta$(CDCl$_3$)ppm: 1.32 (3H; t; J=6Hz), 1.45 (9H; s), 1.80~2.23 (4H; m), 3.00~3.60 (4H; m), 3.72 (2H; s), 3.80 (3H; s), 3.93~4.40 (3H; m), 6.84 (2H; d; J=9Hz), 7.23 (2H; d; J=9Hz)

(3) 3-(1-t-Butoxycarbonyl-4-p-methoxybenzylthiopyrrolidin-2-yl)-propionitrile The compound (4.55 g) obtained in the step (2) was dissolved in 11 ml of ethanol, added 15 ml of 1N NaOH at 0° to 5° C. and stirred for one hour at room temperature. To the solution was added water, washed with ether, the water phase was acidified with HCl and the extraction with ethyl acetate was effected. The extract was dried over Na$_2$SO$_4$ and then the solvent was distilled off under reduced pressure. The residue obtained was dissolved in 50 ml of xylene and refluxed under heating for two hours. The residue, obtained after the distillation of the solvent under reduced pressure, was purified by passing it through a column packed with 50 g silica gel and eluting the product with benzene-ethyl acetate (95:5 v/v) to obtain the objective compound (yield: 3.4 g).

N. M. R. $\delta$(CDCl$_3$)ppm: 1.46 (9H; s), 1.50~2.50 (6H; m), 2.90~3.60 (3H; m), 3.68 (2H; s), 3.76 (3H; s), 3.80~4.30 (1H; m), 6.78 (2H; d; J=9Hz), 7.18 (2H; d; J=9Hz)

(4) 3-(1-t-Butoxycarbonyl-4-methoxybenzylthiopyrrolidin-2-yl) propionic acid

To the compound (3.4 g) obtained in the preceeding step (3) was added a mixed solution of 50% ethanol aq. solution (30 ml) and KOH (4.5 g) and refluxed under heating for 6 hours. The solvent was distilled off under reduced pressure, added water to the residue, acidified with HCl and extracted with ethyl acetate. The solvent of the extract was distilled off under reduced pressure after drying over Na$_2$SO$_4$. The residue was purified by column chromatography utilizing 25 g of silica gel and chloroform-methanol (99:1 v/v) as an eluent to obtain 2.9 g of the objective compound.

N. M. R. $\delta$(CDCl$_3$)ppm: 1.46 (9H; s), 1.50~2.15 (4H; m), 2.15~2.45 (2H; m), 3.00~3.60 (3H; m), 3.68 (2H; s), 3.78 (3H; s), 6.75 (2H; d; J=9Hz), 7.15 (2H; d; J=9Hz), 9.30 (1H; brs)

(5) 3-(1-t-Butoxycarbonyl-4-p-methoxybenzylthiopyrrolidin-2-yl)propanol

The compound (2.9 g) obtained in the preceeding step (4) was dissolved in THF (30 ml), added 1.13 ml of triethylamine, cooled to −10° C. and added dropwise 0.77 g of methyl chlorocarbonate while stirring. The mixture was stirred for 30 minutes at 0° to 5° C. and for further 30 minutes at 50° C. and then precipitates were filtered off. To the filtrate was added 0.15 g of lithium borohydride and stirred for two hours at room temperature. The reaction liquid was concentrated under reduced pressure, added ethyl acetate, water and ammonium chloride, then the organic phase was separated, washed with saturated NaCl aq. solution, dried over Na$_2$SO$_4$ and distilled off the solvent to obtain 2.6 g of the objective compound.

N. M. R. $\delta$(CDCl$_3$)ppm: 1.46 (9H; s), 1.50~2.20 (6H; m), 3.00~3.70 (5H; m), 3.70 (2H; s), 3.78 (3H; s), 6.79 (2H; d; J=9Hz), 7.16 (2H; d; J=9Hz)

(6) 3-(1-t-Butoxycarbonyl-4-p-methoxybenzylthiopyrrolidin-2-yl)propyl tosylate The compound (2.6 g) obtained in the above step (5) was dissolved in 20 ml of pyridine, added 2.8 g of p-toluenesulfonyl chloride and stirred for 17 hours at 0° to 5° C. The solvent was distilled off under reduced pressure, then added ethyl acetate to the residue and washed with water. The solvent in the organic phase was distilled off under reduced pressure after drying the phase over Na$_2$SO$_4$. The resulting residue was purified by column chromatography utilizing 50 g of silica gel and benzene-ethyl acetate (98:2 v/v) as an eluent to obtain 1.4 g of the objective compound.

N. M. R. $\delta$(CDCl$_3$)ppm: 1.42 (9H; s), 1.40~2.00 (6H; m), 2.42 (3H; s), 2.80~3.60 (3H; m), 3.67 (2H; s), 3.76 (3H; s), 3.85~4.23 (3H; m), 6.78 (2H; d; J=9Hz), 7.10~7.35 (4H; m), 7 72 (2H; d; J=9Hz)

(7) 2-p-Methoxybenzylthiopyrrolizidine

To a mixture of the compound (1.4 g) obtained in the above step (6) and anisole (1.5 ml) was added 5 ml of trifluoroacetic acid under ice cooling and stirring and further stirred for 30 minutes at that temperature. The solvent was distilled off under reduced pressure and the residue was washed with ether. The residue was dissolved in DMF (10 ml), added 0.95 g of potassium carbonate and stirred for 17 hours at room temperature. The solvent was distilled off under reduced pressure, added chloroform, washed with water, dried over Na$_2$SO$_4$ and distilled off the solvent under reduced pressure. The residue was passed through a column packed with 15 g of silica gel and eluted with chloroform-methanol (95:5 v/v) to obtain the purified objective compound (yield: 0.47 g).

N. M. R. $\delta$(CDCl$_3$)ppm: 1.50~2.20 (6H; m), 2.26~2.60 (1H; m), 2.80~3.30 (4H; m), 3.69 (2H; s), 3.78 (3H; s), 6.78 (2H; d; J=9Hz), 7.18 (2H; d; J=9Hz)

(8) 2-p-Methoxybenzylthio-4-methylpyrrolizidinium iodide 400 mg of the compound obtained in the step (7) was dissolved in 7 ml of acetone, added 0.47 ml of methyl iodide and kept standing for two days at room temperature. The solvent was distilled off under reduced pressure, the residue was washed with ether several times and dried to obtain the objective compound (yield: 600 mg).

(9) 2-Mercapto-4-methylpyrrolizidinium trifluoromethane sulfonate

To a mixture of the compound (600 mg) obtained in the above step (8), anisole (1 ml) and trifluoroacetic acid (6 ml) was added 0.7 ml of trifluoromethane sulfonic acid at room temperature while stirring and further stirred for one hour at that temperature. The solvent was distilled off under reduced pressure, the residue was repeatedly washed with petroleum ether and thus the objective compound was obtained as oily material (yield: 450 mg).

N. M. R. δ(D$_2$O)ppm: 1.70~2.60 (6H; m), 3.23 (3H; s), 3.25~4.40 (6H; m), 4.80 (HOD)

What is claimed is:

1. A derivative of penem represented by the following formula (I):

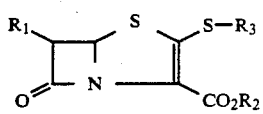  (I)

wherein substituent R$_1$ represents a hydrogen, a C$_1$–C$_6$ alkyl or a hydroxy C$_1$–C$_6$ alkyl group; COOR$_2$ represents carboxyl group or carboxylate anion and R$_2$ may be a removable protective group; and R$_3$ represents a bicyclo-heterocyclic group selected from the group consisting of:

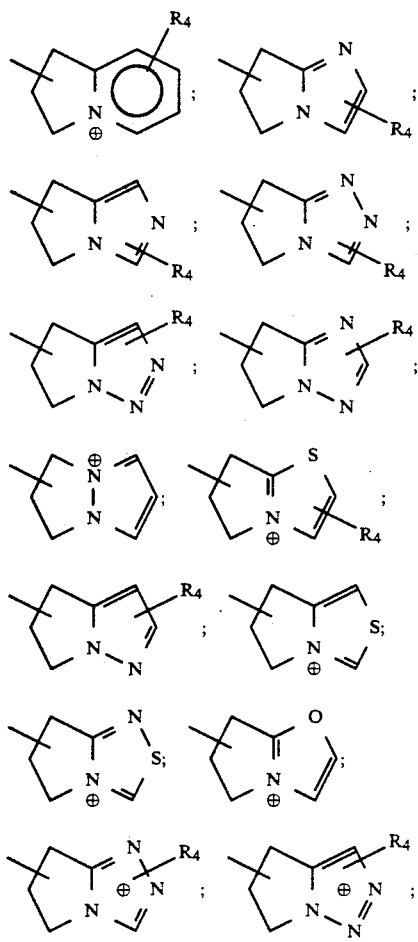

-continued

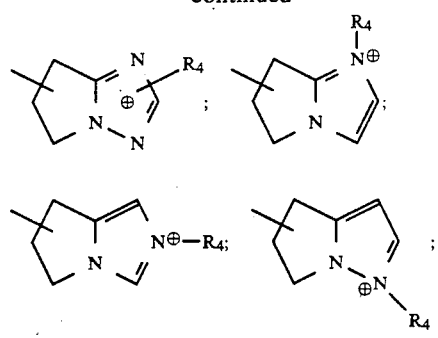

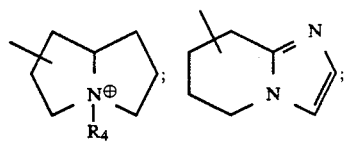

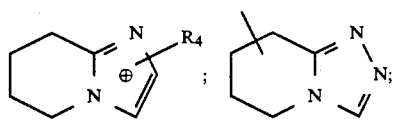

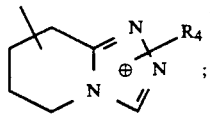

R$_4$ represents a C$_1$–C$_6$ alkyl group, a C$_1$–C$_6$ alkyl- carbonyl- C$_1$–C$_6$ alkyl group, a C$_3$–C$_6$ cycloalkyl group, a C$_3$–C$_6$ cycloalkyl- C$_1$–C$_6$ alkyl group, a cyano group, a cyano- C$_1$–C$_6$ alkyl group, a carboxy- C$_1$–C$_6$ alkyl group, a formyl- C$_1$–C$_6$ alkyl group, a formylamino- C$_1$–C$_6$ alkyl group, a C$_2$–C$_6$ alkenyl group, a C$_2$–C$_6$ alkynyl group, a C$_1$–C$_6$ alkoxy- carbonyl- C$_1$–C$_6$ alkyl group, a carbamoyl group, a carbamoyl- C$_1$–C$_6$ alkyl group, a (mono- C$_1$–C$_6$ alkyl)- carbamoyl group, a (mono-C$_1$–C$_6$ alkyl- carbamoyl)- C$_1$–C$_6$ alkyl group, a (di- C$_1$–C$_6$ alkyl)- carbamoyl group, a (di- C$_1$–C$_6$ alkyl-carbamoyl)-C$_1$–C$_6$ alkyl group, an aryl group, an aryl- C$_1$–C$_6$ alkyl group, a halogeno-aryl group, a halogeno-aryl- C$_1$–C$_6$ alkyl group, a halogen atom, a halogeno- C$_1$–C$_6$ alkyl group, an amino group, an amino- C$_1$–C$_6$ alkyl group, a (mono-C$_1$–C$_6$ alkylamino)- C$_1$–C$_6$ alkyl group, a (di- C$_1$–C$_6$ alkylamino)- C$_1$–C$_6$ alkyl group, a hydroxy group, a hydroxy- C$_1$–C$_6$ alkyl group, a C$_1$–C$_6$ alkoxy- C$_1$–C$_6$ alkyl group, a C$_1$–C$_6$ alkyl- sulfo- C$_1$–C$_6$ alkyl group, an aryl-carbonyl- C$_1$–C$_6$ alkyl group, a halogeno-aryl-carbonyl- C$_1$–C$_6$ alkyl group or an (N-methyl-tetrazoryl-5-yl)thiomethyl group; and pharaceutically acceptable salts thereof.

2. A derivative of penem as set forth in claim 1 wherein it is a (5R, 6S, 8R)-6-(1-hydroxyethyl)-derivative of penem.

3. A derivative of penem as set forth in claim 1 wherein it is represented by the following formula (Ia):

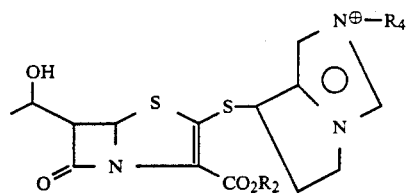

or

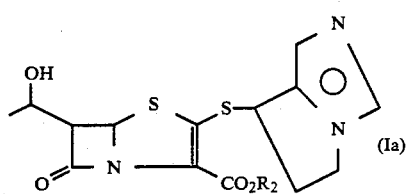

wherein $R_2$ is H or $COOR_2$ means carboxylate anion, $R_4$ is $-CH_3$, $-CH_2CN$, $-CH_2-C\equiv CH$, $-CH_2-CO-CH_3$ or $-CH_2CONH_2$, $-CH_2CH_3$.

4. A derivative of penem as set forth in claim 1 wherein it is represented by the following formula (Ib):

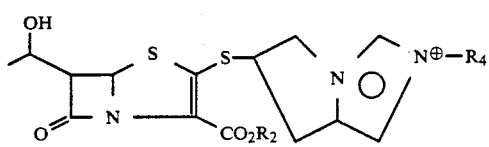

or

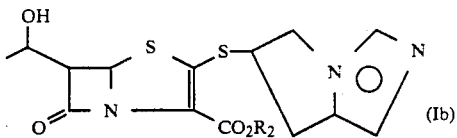

wherein $R_2$ is H or $COOR_2$ represents carboxylate anion and $R_4$ is methyl.

5. A derivative of penem as set forth in claim 1 wherein it is represented by the following formula (Ic):

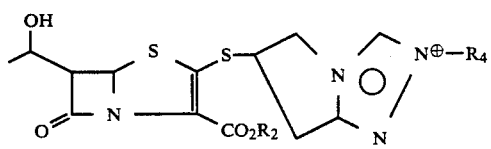

or

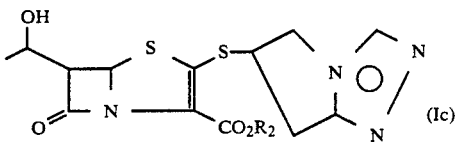

wherein $R_2$ is H or represents carboxylate anion as $COOR_2$ and $R_4$ is methyl.

* * * * *

UNITED STATES PATENT AND TRADEMARK OFFICE
CERTIFICATE OF CORRECTION

PATENT NO. :   5,079,357
DATED      :   January 7, 1992
INVENTOR(S) :  Makoto SATO, ET AL It is certified that error appears in the above-identified patent and that said Letters Patent is hereby corrected as shown below:

On the title page: under the heading "OTHER PUBLICATIONS" in the second column: delete "Derwent Publication 85-2463531/24" and insert -- Derwent Publication 85-246531/24 --

In the Abstract, line 1 thereof: delete "pharmacutically" and insert -- pharmaceutically --

Signed and Sealed this

Twenty-seventh Day of April, 1993

Attest:

MICHAEL K. KIRK

*Attesting Officer*   Acting Commissioner of Patents and Trademarks